(12) United States Patent
Hariri et al.

(10) Patent No.: US 8,889,411 B2
(45) Date of Patent: *Nov. 18, 2014

(54) MODULATION OF STEM AND PROGENITOR CELL DIFFERENTIATION, ASSAYS, AND USES THEREOF

(75) Inventors: Robert J. Hariri, Florham Park, NJ (US); David I. Stirling, Warren, NJ (US); Laure A. Moutouh-De Parseval, San Diego, CA (US); Kyle W. H. Chan, San Diego, CA (US)

(73) Assignee: Anthrogenesis Corporation, Warren, NJ (US)

( * ) Notice: Subject to any disclaimer, the term of this patent is extended or adjusted under 35 U.S.C. 154(b) by 836 days.

This patent is subject to a terminal disclaimer.

(21) Appl. No.: 12/396,397

(22) Filed: Mar. 2, 2009

(65) Prior Publication Data

US 2009/0226406 A1    Sep. 10, 2009

Related U.S. Application Data

(62) Division of application No. 10/411,655, filed on Apr. 11, 2003, now Pat. No. 7,498,171.

(60) Provisional application No. 60/372,348, filed on Apr. 12, 2002, provisional application No. 60/437,348, filed on Dec. 31, 2002, provisional application No. 60/437,350, filed on Dec. 31, 2002.

(51) Int. Cl.
  *C12N 5/00*     (2006.01)
  *C12N 5/0789*   (2010.01)
  *C12N 5/0784*   (2010.01)
  *C12N 5/0787*   (2010.01)
  *A61K 35/12*    (2006.01)

(52) U.S. Cl.
  CPC ........ *C12N 5/0642* (2013.01); *C12N 2501/385* (2013.01); *C12N 5/0647* (2013.01); *C12N 5/0639* (2013.01); *C12N 2501/70* (2013.01); *C12N 2501/22* (2013.01); *C12N 2506/02* (2013.01); *C12N 2501/23* (2013.01); *C12N 2501/25* (2013.01); *C12N 2501/14* (2013.01); *C12N 2501/125* (2013.01); *A61K 2035/124* (2013.01)
  USPC ............................ 435/377; 435/325; 435/375

(58) Field of Classification Search
  CPC ... A61K 2300/00; A61K 35/28; A61K 35/14; C12N 5/0647; C12N 5/0634; C12N 5/0694
  See application file for complete search history.

(56) References Cited

U.S. PATENT DOCUMENTS

| | | | |
|---|---|---|---|
| 5,004,681 A * | 4/1991 | Boyse et al. ............... 435/2 |
| 5,367,057 A * | 11/1994 | Lemischka ............... 530/350 |
| 5,385,901 A | 1/1995 | Kaplan | |
| 5,399,493 A * | 3/1995 | Emerson et al. .......... 435/456 |
| 5,463,063 A | 10/1995 | Muller | |
| 5,599,703 A * | 2/1997 | Davis et al. ............... 435/373 |
| 5,605,914 A | 2/1997 | Muller et al. | |
| 5,635,365 A | 6/1997 | Ansari et al. | |
| 5,635,517 A | 6/1997 | Muller et al. | |
| 5,643,915 A | 7/1997 | Andrulis, Jr. et al. | |
| 5,654,312 A | 8/1997 | Andrulis, Jr. et al. | |
| 5,658,940 A | 8/1997 | Muller | |
| 5,665,754 A | 9/1997 | Feldman et al. | |
| 5,672,346 A | 9/1997 | Srour et al. | |
| 5,698,579 A | 12/1997 | Muller | |
| 5,703,098 A | 12/1997 | Muller | |
| 5,728,844 A | 3/1998 | Muller | |
| 5,728,845 A | 3/1998 | Muller | |
| 5,731,325 A | 3/1998 | Andrulis, Jr. et al. | |
| 5,736,570 A | 4/1998 | Muller | |
| 5,801,195 A | 9/1998 | Muller | |
| 5,806,529 A * | 9/1998 | Reisner et al. ............. 128/898 |
| 5,851,984 A | 12/1998 | Matthews et al. | |
| 5,874,448 A | 2/1999 | Muller | |
| 5,877,200 A | 3/1999 | Muller | |
| 5,925,567 A | 7/1999 | Kraus et al. | |
| 5,929,117 A | 7/1999 | Muller | |
| 5,968,945 A | 10/1999 | Muller | |
| 6,011,050 A | 1/2000 | Muller | |
| 6,020,358 A | 2/2000 | Muller | |
| 6,022,848 A | 2/2000 | Kozlov et al. | |
| 6,046,019 A * | 4/2000 | Goumeniouk et al. ....... 435/28 |
| 6,046,221 A | 4/2000 | Muller | |

(Continued)

FOREIGN PATENT DOCUMENTS

| | | |
|---|---|---|
| WO | WO 92/14455 | 9/1992 |
| WO | WO 95/01348 | 1/1995 |

(Continued)

OTHER PUBLICATIONS

Weinreb S et al. 1998. Transplantation of unrelated cord blood cells. Bone Marrow Transplantation 22: 193-96.*

(Continued)

*Primary Examiner* — Lora E Barnhart Driscoll
(74) *Attorney, Agent, or Firm* — Jones Day

(57) ABSTRACT

The present invention relates to methods of modulating mammalian stem cell and progenitor cell differentiation. The methods of the invention can be employed to regulate and control the differentiation and maturation of mammalian, particularly human stem cells along specific cell and tissue lineages. The methods of the invention relate to the use of certain small organic molecules to modulate the differentiation of stem or progenitor cell populations along specific cell and tissue lineages, and in particular, to the differentiation of embryonic-like stem cells originating from a postpartum placenta or for the differentiation of early progenitor cells to a granulocytic lineage. Finally, the invention relates to the use of such differentiated stem or progenitor cells in transplantation and other medical treatments.

11 Claims, 34 Drawing Sheets

(56) References Cited

U.S. PATENT DOCUMENTS

Figure 1:
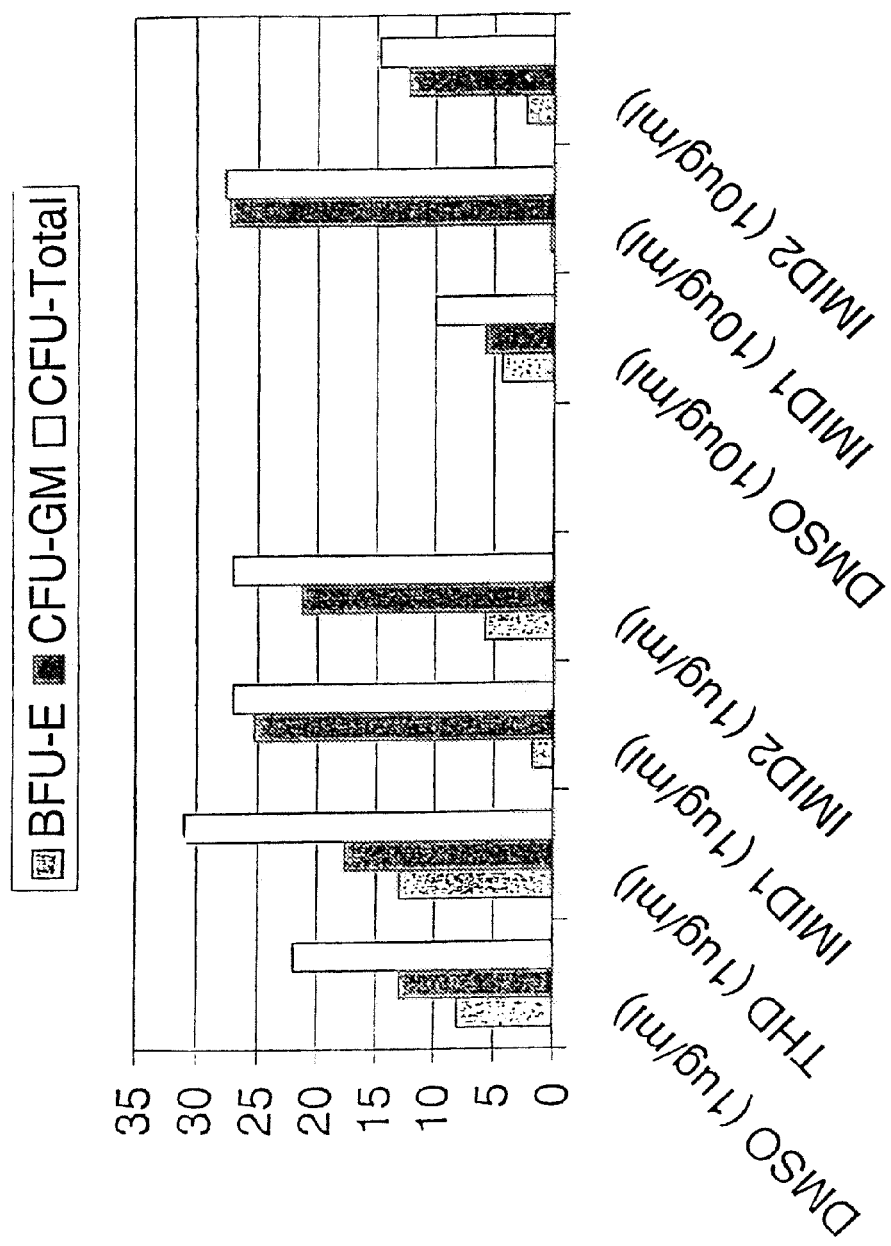

| | | | |
|---|---|---|---|
| 6,057,123 A | 5/2000 | Craig et al. |
| 6,093,531 A | 7/2000 | Bjornson et al. |
| 6,110,739 A | 8/2000 | Keller et al. |
| 6,127,135 A | 10/2000 | Hill et al. |
| 6,130,226 A | 10/2000 | Muller |
| 6,140,346 A | 10/2000 | Andrulis, Jr. et al. |
| 6,146,888 A | 11/2000 | Smith et al. |
| 6,180,644 B1 | 1/2001 | Muller |
| 6,200,987 B1 | 3/2001 | Muller |
| 6,214,857 B1 | 4/2001 | Muller |
| 6,224,860 B1 | 5/2001 | Brown |
| 6,251,383 B1 | 6/2001 | Upadhyay et al. |
| 6,255,112 B1 | 7/2001 | Thiede et al. |
| 6,280,718 B1 | 8/2001 | Kaufman et al. |
| 6,281,230 B1 | 8/2001 | Muller |
| 6,306,575 B1 | 10/2001 | Thomas et al. |
| 6,316,471 B1 | 11/2001 | Muller |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,476,052 B1 | 11/2002 | Muller |
| 6,576,464 B2 | 6/2003 | Gold et al. |
| 7,045,148 B2 | 5/2006 | Hariri |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,682,803 B2 | 3/2010 | Paludan et al. |
| 7,700,090 B2 | 4/2010 | Heidaran et al. |
| 7,909,806 B2 | 3/2011 | Goodman |
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 2002/0123141 A1 | 9/2002 | Hariri |
| 2002/0160510 A1 | 10/2002 | Hariri |
| 2003/0032179 A1 | 2/2003 | Hariri |
| 2003/0180269 A1 | 9/2003 | Hariri |
| 2003/0235909 A1 | 12/2003 | Hariri |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0171147 A1 | 9/2004 | Hariri |
| 2004/0219136 A1 | 11/2004 | Hariri |
| 2005/0019908 A1 | 1/2005 | Hariri |
| 2005/0118715 A1 | 6/2005 | Hariri |
| 2005/0143420 A1 | 6/2005 | Moutouh-de Parseval |
| 2005/0148034 A1 | 7/2005 | Payvandi |
| 2005/0266391 A1 | 12/2005 | Bennett et al. |
| 2005/0272148 A1 | 12/2005 | Hariri |
| 2005/0276792 A1 | 12/2005 | Kaminski |
| 2006/0060494 A1 | 3/2006 | Goodman et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0038298 A1 | 2/2007 | Sulner et al. |
| 2007/0043328 A1 | 2/2007 | Goodman et al. |
| 2007/0053888 A1 | 3/2007 | Hariri |
| 2007/0092497 A1 | 4/2007 | Hariri |
| 2007/0134210 A1 | 6/2007 | Heidaran |
| 2007/0190034 A1 | 8/2007 | Paludan et al. |
| 2007/0190042 A1 | 8/2007 | Edinger et al. |
| 2007/0275362 A1 | 11/2007 | Edinger et al. |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0172830 A1 | 7/2010 | Heidaran |
| 2010/0183571 A1 | 7/2010 | Paludan et al. |
| 2010/0260847 A1 | 10/2010 | Hariri |
| 2010/0291679 A1 | 11/2010 | Edinger et al. |
| 2010/0297689 A1 | 11/2010 | Edinger et al. |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot et al. |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |

FOREIGN PATENT DOCUMENTS

| | | |
|---|---|---|
| WO | WO 96/20705 | 7/1996 |
| WO | WO 96/20926 | 7/1996 |
| WO | WO 97/08143 | 3/1997 |
| WO | WO 97/12859 | 4/1997 |
| WO | WO 97/23457 | 7/1997 |
| WO | WO 97/29182 | 8/1997 |
| WO | WO 98/03502 | 1/1998 |
| WO | WO 98/06692 | 2/1998 |
| WO | WO 98/24763 | 6/1998 |
| WO | WO 98/54170 | 12/1998 |
| WO | WO 99/06041 | 2/1999 |
| WO | WO 99/46258 | 9/1999 |
| WO | WO 99/47512 | 9/1999 |
| WO | WO 00/25777 | 5/2000 |
| WO | WO 00/55134 | 9/2000 |
| WO | WO 01/87307 | 11/2001 |
| WO | WO 01/87307 A2 | 11/2001 |
| WO | WO 02/46373 | 6/2002 |
| WO | WO 02/063962 | 8/2002 |
| WO | WO 02/064755 | 8/2002 |
| WO | WO 03/044164 | 5/2003 |
| WO | WO 97/29182 | 5/2003 |
| WO | WO 03/068937 | 8/2003 |
| WO | WO 03/086373 | 10/2003 |
| WO | WO 03/087333 | 10/2003 |
| WO | WO 03/087392 | 10/2003 |
| WO | WO 03/102151 | 12/2003 |
| WO | WO 2004/035064 | 4/2004 |
| WO | WO 2004/047770 | 6/2004 |

(56) References Cited

FOREIGN PATENT DOCUMENTS

| WO | WO 2004/071283 | 8/2004 |
|---|---|---|
| WO | WO 2005/055929 | 6/2005 |
| WO | WO 2005/097190 | 10/2005 |
| WO | WO 2007/047465 | 4/2007 |
| WO | WO 2007/047468 | 4/2007 |
| WO | WO 2007/079183 | 7/2007 |
| WO | WO 2008/019148 | 2/2008 |
| WO | WO 2008/051568 | 5/2008 |
| WO | WO 2008/100497 | 8/2008 |
| WO | WO 2012/009422 | 1/2012 |

OTHER PUBLICATIONS

Nagayama H et al. 1999. Immunological reconstitution after cord blood transplantation for an adult patient. Bone Marrow Transplantation 24: 211-13.*
Bender JG et al. 1992. Defining a therapeutic dose of peripheral blood stem cells. J Hematotherapy 1: 329-341.*
Bogomolski-Yahalom V et al. 1995. Disorders of neutrophil function. Blood Rev 9: 183-190.*
U.S. Appl. No. 60/454,155, filed Mar. 12, 2003, Muller, G. et al.
U.S. Appl. No. 60/454,149, filed Mar. 12, 2003, Muller, G. et al.
U.S. Appl. No. 60/438,448, filed Jan. 7, 2003, Muller, G. et al.
U.S. Appl. No. 60/436,975, filed Dec. 30, 2002, Muller, G. et al.
U.S. Appl. No. 60/366,515, filed Mar. 20, 2002, Muller, G. et al.
Bauer et al., 1998, "Inhibition of Angiogenesis by Thalidomide Requires Metabolic Activation, Which is Species-Dependent," Biochem. Pharmacol. 55(11):1827-1834.
Buelens, 1967, "Treatment of a Grade II Astrocytoma with Thalidomide," Arzneimittel-Forschung 17:646-648.
Corral et al., 1999, "Differential Cytokine Modulation and T cell Activation by Two Distinct Classes of Thalidomide Analogoues That are Potent Inhibitor of TNF-alpha," J Immunol. 163(1):380-6.
Costa et al., 1998, "Thalidomide (TLD) and Pentooxifyline (PTX) Prevent the Development f Chronic Cardiomyopathy Provoked by Doxorubicin (DXR) in Rats Without its Anti-Tumoral Effect," Blood 92(10:suppl. 1):235b.
Craig et al., 1967, "Potential Anticancer Agents. III. 2-phthalimidoaldehydes and Derivatives," J. Med. Chem 10(6):1071-1073.
D'Amato et al., 2001, "Mechanism of Action of Thalidomide and 3-aminothalidomide in Multiple Myeloma," Semin. Oncol. 28:597-601.
D'Amato et al., 1994, "Thalidomide is an Inhibitor of Angiogenesis," Proc. Natl. Acad. Sci. 91:4082-4085.
Damjanov et al., 1993, "Retinoic Acid-Induced Differentiation of the Developmentally Pluripotent Human Germ Cell Tumor-Derived Cell Line, NCCIT," Lab Invest. 68(2):220-32.
DeLoia et al., 1998, "Effects of Methotrexate on Trophoblast Proliferation and Local Immune Responses," Human Reproduction 13(4):1063-1069.
Douay et al., 1995, "Characterization of Late and Early Hematopoietic Progenitor/Stem Cell Sensitivity to Mafosfamide," Bone Marrow Transplant. 15(5):769-75.
Dushnik-Levinson et al., 1995, "Embryogenesis in vitro: Study of Differentiation of Embryonic Stem Cells," Biol. Neonate. 67(2):77-83.
Friedman et al., 2000, "Temozolomide and Treatment of Malignant Glioma," Clinical Cancer Research, 6:2585-2597.
Grabstald et al., 1965, "Clincial Experiences with Thalidomide in Patients with Cancer," Clinical Pharmacology and Therapeutics 6:298-302.
Hatzopoulos et al., 1998, "Isolation and Characterization of Endothelial Progenitor Cells From Mouse Embryos," Development 125(8):1457-1468.
Himori et al., 1984, "Chemotherapeutic Susceptibility of Human Bone Marrow Progenitor Cells and Human Myelogenous Leukemia Cells (HL-60) in Co-Culture: Prelminary Report," Int. J. Cell Cloning 2(4):254-62.

Hwu et al., 2000, "New Approaches in the Treatment of Metastatic Melanoma: Thalidomide and Temozolomide," Oncology Supp. 13:25-28.
Kobari et al., 2001, "CD133+ Cell Selection is an Alternative to CD34+ Cell Selection for ex vivo Expansion of Hematopoietic Stem Cells," J Hematother Stem Cell Res.10(2):273-81.
Koch et al., 1985, "Thalidomide and Congeners and Anti-Inflammatory Agents," Prog. Med. Chem. 22:165-242.
Lentzsch et al., 2002, "S-3-amino-phthalimido-glutarimide Inhibits Angiogenesis and Growth of B-cell Neoplasias in Mice," Cancer Research 62:2300-2305.
Miyachi et al., 1997. "Novel Biological Response Modifiers: Phthalimides with Tumor Necrosis Factor-alpha Production-Regulating Activity," J. Med. Chem. 40:2858-2865.
Moreira et al., 1993, "Thalidomide Exerts its Inhibitory Action on Tumor Necrosis Factor a by Enhancing mRNA Degradation," J. Expr. Med. 177:1675-1680.
Muller, George, et al., 1999, "Amino-substituted thalidomide analogs: potent inhibitors of TNF-alpha production," *Bioorganic & Medicinal Chemistry Letters* 9; pp. 1625-1630.
Muller et al., 1998, "Thalidomide analogs and PDE4 inhibition," *Bioorg. & Med Chem Lett.* 8:2669-2674.
Muller, et al., 1996, "Structural modifications of thalidomide produce analogs with enhanced tumor necrosis factor inhibitory activity," *J. Med. Chem.* 39(17):3238.
Nadkarni et al., 1984, "Effect of Retinoic Acid on Bone Marrow Committed Stem Cells (CFU-c) from Chronic Myeloid Leukemia Patients," Tumori. 70(6):503-5.
Shimazawa et al., 1999, "Antiangiogenic Activity of Tumor Necrosis Factor-alpha Production Regulators Derived from Thalidomide," Biol. Pharm. Bull. 22(2):224-226.
Tremblay et al., 2001, "Diethylstilbestrol Regulates Trophoblast Stem Cell Differentiation as a Ligand of Orphan Nuclear Receptor ERR Beta," Genes Dev. 15(7):833-8.
Uchida et al., 2000, "Direct isolation of human central nervous system stem cells," Proc Natl Acad Sci USA 97(26):14720-5.
Von Melchner et al., 1985, "Human Placental Conditioned Medium Reverses Apparent Commitment to Differentiation of Human Promyelocytic Leukemia Cells (HL60)," Blood 66(6):1469-1472.
Yan et al., 2001 "Retinoic Acid Promotes Differentiation of Trophoblast Stem Cells to a Giant Cell Fate," Devel. Biol. 235(2):422-432.
Ye et al., 2002, "Novel IMiD Drugs Enhance Expansion and Regulate Differentiation of Human Cord Blood CD34+ Cells with Cytokines." Blood vol. 100, Abstract No. 4099.
Masellis et al., "Changes in gene Expression in Bone Marrow Mesenchymal Progenitor Cells as a Consequence of Imid Therapy in Multiple Myeloma Patients," American Society of Hematology, 43$^d$ Annual Meeting, Dec. 7-11, 2001, Orlando, Florida, Abstract # 1548.
Mitsiades et al., "Apoptotoc Signalling Induced by Immunomodulatory Thalidomide Analogs (Imids) in Human Multiple Myeloma Cells: Therapeutic Implications," American Society of Hematology, 43$^d$ Annual Meeting, Dec. 7-11, 2001, Orlando, Florida, Abstract # 3224.
Payvandi et al., "Novel Imid Drugs Enhance Expansion and Regulate Differentiation of Human Cord Blood CD34+ Cells with Cytokines," American Society of Hematology, 44$^{th}$ Annual Meeting, Dec. 6-10, 2002, Philadelphia, Pennsylvania, Abstract # 4099.
U.S. Appl. No. 11/580,588, filed Oct. 13, 2006, Paludan.
U.S. Appl. No. 11/580,625, filed Oct. 13, 2006, Heidaran.
U.S. Appl. No. 11/648,802, filed Dec. 28, 2006, Heidaran.
U.S. Appl. No. 11/648,804, filed Dec. 28, 2006, Edinger.
U.S. Appl. No. 11/648,812, filed Dec. 28, 2006, Heidaran.
U.S. Appl. No. 11/648,813, filed Dec. 28, 2006, Edinger.
U.S. Appl. No. 11/648,824, filed Dec. 28, 2006, Heidaran.
Dredge, et al., "Protective Antitumor Immunity Induced by a Costimulatory Thalidomide Analog in Conjunction with Whole Tumor Cell Vaccination is Mediated by Increased Th1-Type Immunity." *The Journal of Immunology*, vol. 168, No. 10, May 15, 2002, pp. 4914-4919.
Govindarajan, et al., "Effect of Thalidomide on Gastrointestinal Toxic Effects of Irinotecan." *The Lancet*, vol. 356, No. 9229, Aug. 12, 2000, pp. 566-567.

(56) References Cited

OTHER PUBLICATIONS

Raza, et al., "Thalidomide Produces Transfusion Independence in Long-Standing Refractory Anemias of Patients with Myelodysplatic Syndromes." *Blood*, vol. 98, No. 4, Aug. 15, 2001, pp. 958-965.
Sauer, et al., "Thalidomide Inhibits Angiogenesis in Embryoid Bodies by the Generation of Hydroxyl Radicals." *American Journal of Pathology*, vo. 156, No. 1, Jan. 2000, pp. 151-158.
Broxmeyer et al., "Human Umbilical Cord Blood as a Potential Source of Transplantable Hematopoietic Stem/Progenitor Cells," Proc Natl Acad Sci U S A. 86(10):3828-32 (1989).
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth," 15 pages, stamped received by OIPE on May 28, 1999, paper dated May 13, 1999.
Lee et al., "Clinical Efficacy of Granulocyte Transfusion Therapy in Patients With Neutropenia-Related Infections," Leukemia 15(2):203-7 (2001).
Szabolcs et al., J. Immunol. 154:5851-5861 (1995).
Yin et al., "AC133, A Novel Marker for Human Hematopoietic Stem and Progenitor Cells," Blood 90(12):5002-5012 (1997).
U.S. Appl. No. 13/013,721, filed Jan. 25, 2011, Zhang et al.
U.S. Appl. No. 13/071,437, filed Mar. 24, 2011, Zhang et al.
U.S. Appl. No. 13/081,415, filed Apr. 6, 2011, Abbot.
U.S. Appl. No. 13/081,422, filed Apr. 6, 2011, Edinger.
U.S. Appl. No. 13/089,029, filed Apr. 18, 2011, Hariri et al.
U.S. Appl. No. 13/107,727, filed May 13, 2011, Edinger et al.
U.S. Appl. No. 13/107,778, filed May 13, 2011, Edinger et al.
U.S. Appl. No. 13/108,871, filed May 16, 2011, Hariri.
U.S. Appl. No. 13/108,891, filed May 16, 2011, Hariri.
U.S. Appl. No. 13/108,901, filed May 16, 2011, Hariri.
Bauer et al., "Inhibition of Angiogenesis by Thalidomide Requires Metabolic Activation, Which is Species-Dependent," Biochem. Pharmacol. 55(11):1827-1834 (1998).
Buelens, "Treatment of a Grade 11 Astrocytoma with Thalidomide," Arzneimittel-Forschung 17:646-648 (1967).
Corral et al., "Differential cytokine modulation and T cell activation by two distinct classes of thalidomide analogues that are potent inhibitors of TNF-alpha," J. Immunol. 163(1):380-386 (1999).
Costa et al., "Thalidomide (TLD) and Pentooxifyline (PTX) Prevent-the Development of Chronic Cardiomyopathy Provoked by Doxorubicin (DXR) in Rats Without its Anti-Tumoral Effect," Blood 92 (1O):suppl.1:235b (1998).
Craig et al., "Potential anticancer agents. IIUI. 2-phthalimidoaldehydes and derivatives," Potential Anticancer Agents III 10:1071-1073 (1967).
D'Amato et al., 1994, "Thalidomide is an Inhibitor of Angiogenesis", Proc. Natl. Acad. Sci. 91:4082-4085.
Dredge et al., "Protective antitumor immunity induced by a costimulatory thalidomide analog in conjunction with whole tumor cell vaccination is mediated by increased Th1-type immunity[1]," *The Journal of Immunology*, 2002, 168(10):4914-4919.
Dushnik-Levinson, et al. "Embryogenesis in vitro: study of differentiation of embryonic stem cells." Biol Neonate. 67(2):77-83 (1995).
Friedman et al., "Temozolomide and Treatment of Malignant Glioma," Clinical Cancer Research 6:2585-2597 (2000).
Govindarajan, et al., "Effect of Thalidomide on Gastrointestinal Toxic Effects of Irinotecan," The Lancet, vol. 356, No. 9229, pp. 566-567 (Aug. 12, 2000).
Grabstald et al., "Clinical experiences with thalidomide in patients with cancer," Clinical Pharmacology and Therapeutics 6:298-302 (1965).
Hansen et al., "Differential Alteration by Thalidomide of the Glutathione Content of Rat vs. Rabbit Conceptuses in Vitro," Reprod Toxicol13: 547-554 (1999).
Hatzopoulos, et al. "Isolation and characterization of endothelial progenitor cells from mouse embryos," Development. 125(8):1457-68 (1998).
He, W., et al., 1993, Abstract of papers, 206th American Chemical Society, Chicago, IL; Med. Chem., paper 216.
Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hwu et al., "New Approach in the Treatment of Metastatic Melanoma: Thalidomide and Temozolomide," Oncology Suppl. 13:25-28 (2000).
Kalka et al., "Transplantation of Ex Vivo Expanded Endothelial Progenitor Cells for Therapeutic Neovascularization," Proc. Natl. Acad. Sci. USA 97: 3422-3427 (2000).
Kobari et al., "CDI33 + Cell Selection is an Alternative to CD34 + Cell Selection for ex vivo Expansion of Hematopoietic Stem Cells," J. Hematother. Stem Cell Res. 10(2):273-81 (2001).
Koch et al., "Thalidomide and Congeners and Anti-Inflammatory Agents," Prog. Med. Chern. 22:165-242 (1985).
Koizumi et al., "Large scale purification of human blood CD34+ cells from Cryopreserved Peripheral Blood Stem Cells Using a Nylon-Fiber Syringe System and Immunomagnetic Microspheres," Bone Marrow Transplant 26: 787-793 (2000).
Lentsch, S., Rogers, M., Leblanc, R., Birsner, A., Shah, J., Anderson K., D'Amato R., 3-Amino-Phthalimido-Glutarimide (S-3APG) Inhibits Angiogenesis and Growth in Drug Resistant Multiple Myeloma (MM) in vivo. Abstract #1976, American Society of Hematology, Dec. 7-11, 2001.
Masellis et al., "Changes in gene expression in bone marrow mesenchymal progenitor cells as a consequence of IMiD therapy in multiple myeloma patients," *Blood*, Abstract # 1548, Dec. 7-11, *American Society of Hematology* (2001).
Mayani et al., "Differential Effects of the Hematopoietic Inhibitors MIP-1 Alpha, TGF-Beta, and TNF-Alpha on Cytokine-Induced Proliferation of Subpopulations of CD34+ Cells Purified From Cord Blood and Fetal Liver," Exp. Hematol. 23: 422-427 (1995).
Melchner, et al., "Human Placental Conditioned Medium Reverses Apparent Commitment to Differentiation of Human Promyelocytic Leukemia Cells (HL60)," Blood 66(6):1469-1472 (1985).
Mitsiades et al., "Apoptic signaling induced by immunomodulatory thalidomide analogs (Imids) in human multiple myeloma cells: therapeutic implications," Abstract # 3224, Dec. 7-11, 2001, *American Society of Hematology*.
Miyachi et al., 1997, "Novel biological response modifiers: phthalimides with tumor necrosis factor-alpha production-regulating activity," J. Med. Chem. 40:2858-2865.
Moreira et al., "Thalidomide Exerts its Inhibitory Action on Tumor Necrosis Factoraby Enhancing mRNA Degradation," J. Expr. Med. 177: 1675-1680 (1993).
Morse, et al., "Generation of Dendritic Cells in vitro from Peripheral Blood Mononuclear Cells with Granulocyte-Macrophage-Colony-Stimulating Factor, Interleukin-4, and Tumor Necrosis Factor-alpha for Use in Cancer Immunotherapy," Ann. Surg. 226(1):6-16 (1997).
Muller et al., 1996, "Structural modifications of thalidomide produce analogs with enhanced tumor necrosis factor inhibitory activity," J. Med. Chem. 39(17):3238-3240.
Muller et al., 1998, "Thalidomide analogs and PDE4 inhibition," Bioorg. Med. Chem. Lett. 8(19):2669-2674.
Nadkarni, et al., "Effect of Retinoic Acid on Bone-Marrow Committed Stem Cells (CFU-c) from Chronic myeloid Leukemia Patients," Tumori. 70(6):503-505 (1984).
Raza et al., "Thalidomide produces transfusion independence in long-standing refractory anemias of patients with myelodysplatic syndromes," Blood 98(4):958-965 (2001).
Sauer, et al., "Thalidomide Inhibits Angiogenesis in Embryoid Bodies by the Generation of Hydroxyl Radicals." American Journal of Pathology, vo. 156, No. 1, pp. 151-158 (Jan. 2000).
Shalhoub et al., "Osteoprotegrin and Osteoprotegerin Ligand Effects on Osteoclast Formation from Human Peripheral Blood Mononuclear Cell Precursors," J. Cell Biochem. 72:251-261 (1999).
Shimazawa et al., "Antiangiogenic activity of tumor necrosis factor-alpha production regulators derived from thalidomide," Biol. Pharm. Bull. 22(2): 224-226 (1999).
Skobin et al., "Tumor Necrosis Factor-.alpha. and TNF-.beta. Inhibit Clonogenicity of Mobilized Human Hematopoietic Progenitors," Journal of Interferon and Cytokine Research 20:507-510 (2000).

(56) References Cited

OTHER PUBLICATIONS

Uchida et al., Direct Isolation of Human Central Nervous System Stem Cells, Proc. Natl. Acad. Sci. USA 97(26): 14720-5 (2000).

Wood et al., "CD34 Expression Patterns During Early Mouse Development are Related to Modes of Blood Vessel Formation and Reveal Additional Sites of Hematopoiesis," Blood 90: 2300-2311 (1997).

Yan et al., Retinoic acid promotes differentiation of trophoblast stem cells to a giant cell fate.Dev Biol. 235(2): 422-32 (2001).

Ye et al., "Novel IMiD drugs enhance expansion and regulate differentiation of human cord blood CD34+ cells with cytokines," *Blood, Abstract #4099, American Society of Hematology* (Dec. 6-10, 2002).

Notice of Allowance dated Oct. 30, 2008 in U.S. Appl. No. 10/411,655, now US Patent No. 7,498,171.

Office Action dated Feb. 28, 2008 in U.S. Appl. No. 10/411,655, now US Patent No. 7,498,171.

Office Action dated Jul. 11, 2007 in U.S. Appl. No. 10/411,655, now US Patent No. 7,498,171.

Office Action dated May 18, 2006 in U.S. Appl. No. 10/411,655, now US Patent No. 7,498,171.

Office Action dated Nov. 20, 2006 in U.S. Appl. No. 10/411,655, now US Patent No. 7,498,171.

Nagayama et al., "Immunological reconstitution after cord blood transplantation for an adult patient", Bone Marrow Transplantation 24: 211-213 (1999).

U.S. Appl. No. 13/251,059, filed Sep. 30, 2011, Hariri.

U.S. Appl. No. 13/293,037, filed Nov. 9, 2011, Heidaran.

\* cited by examiner

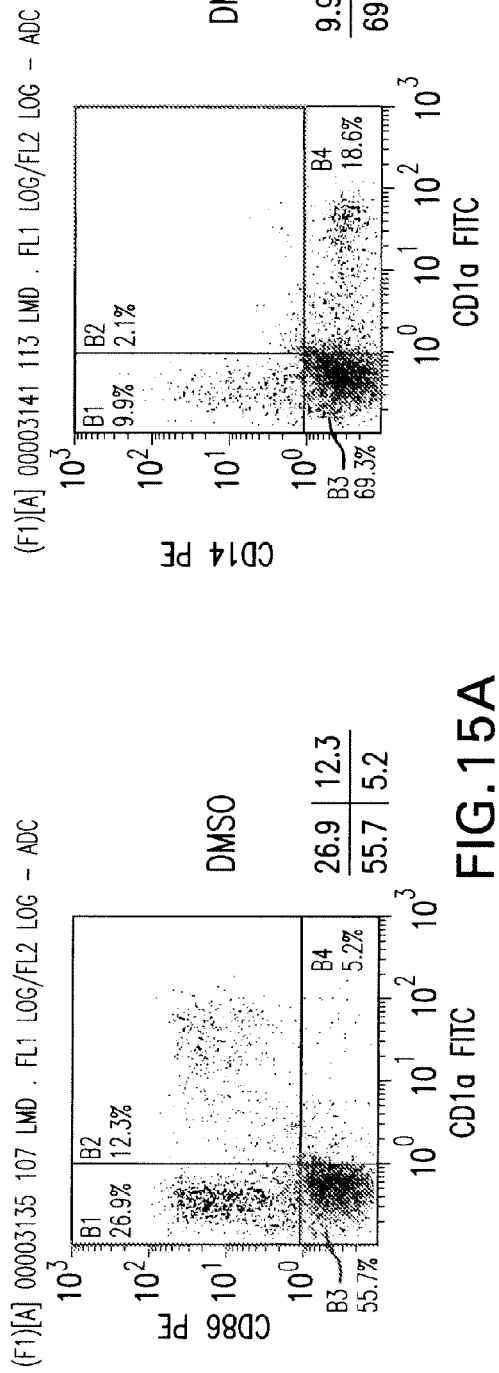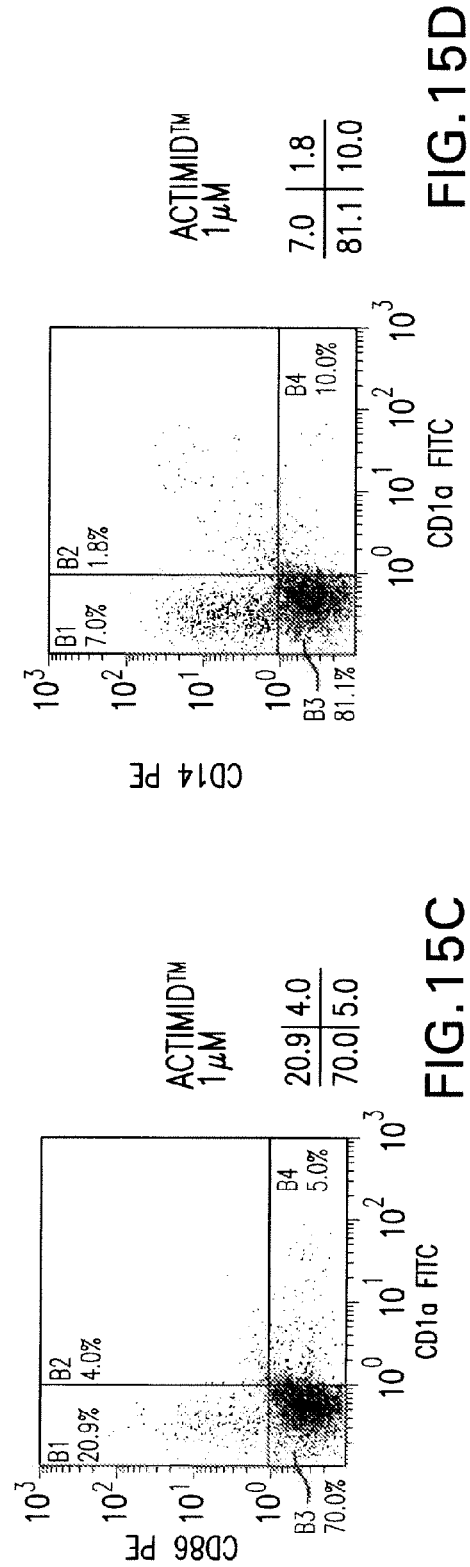

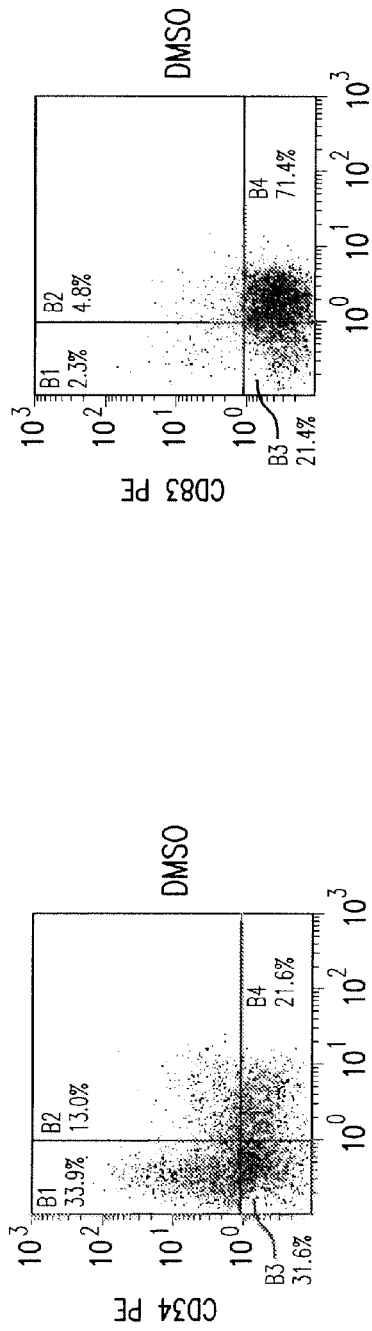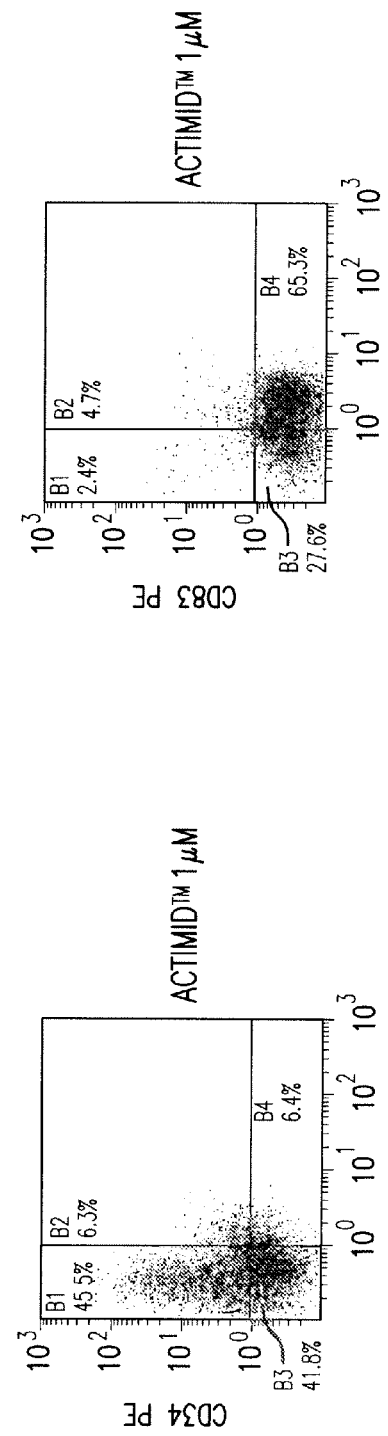

Figure 20D:
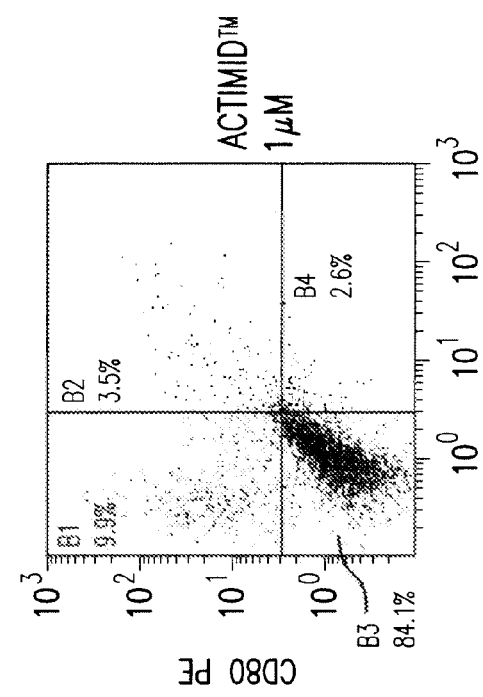

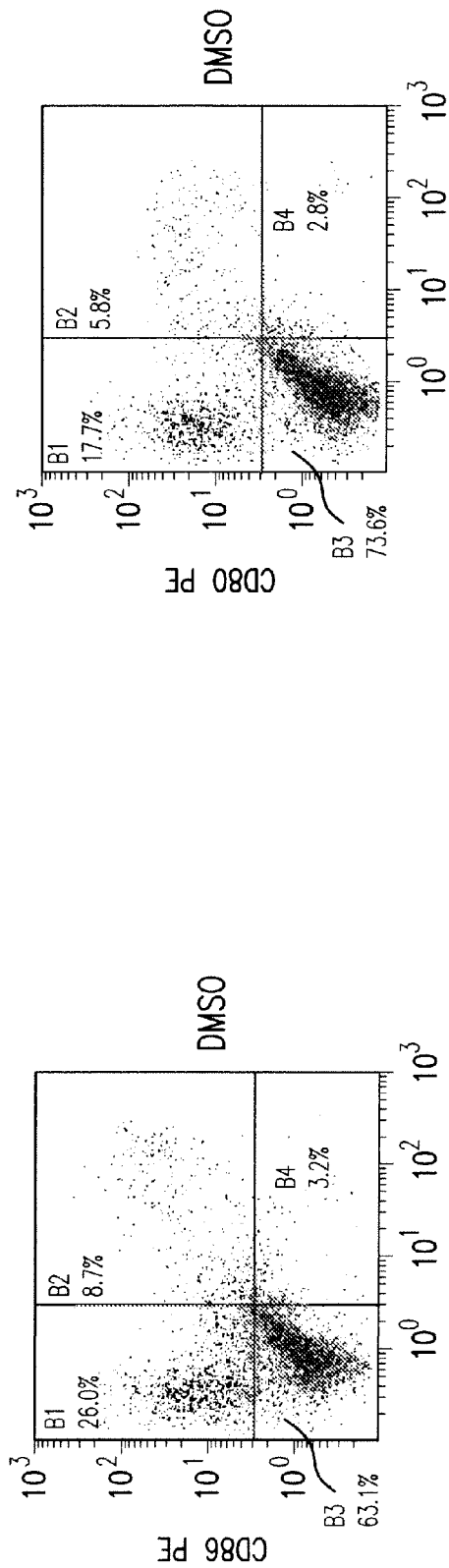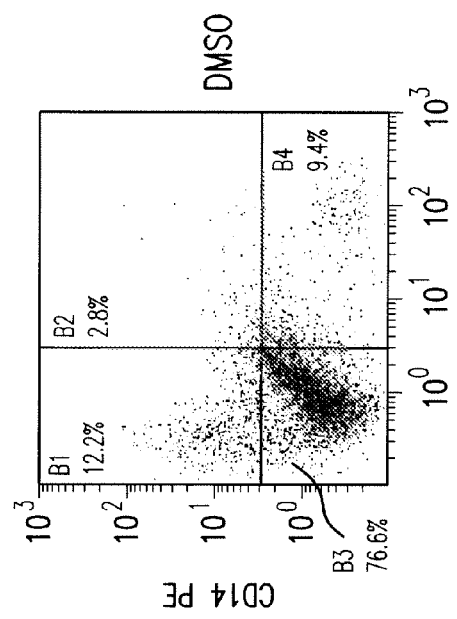
FIG.20A
FIG.20B
FIG.20C

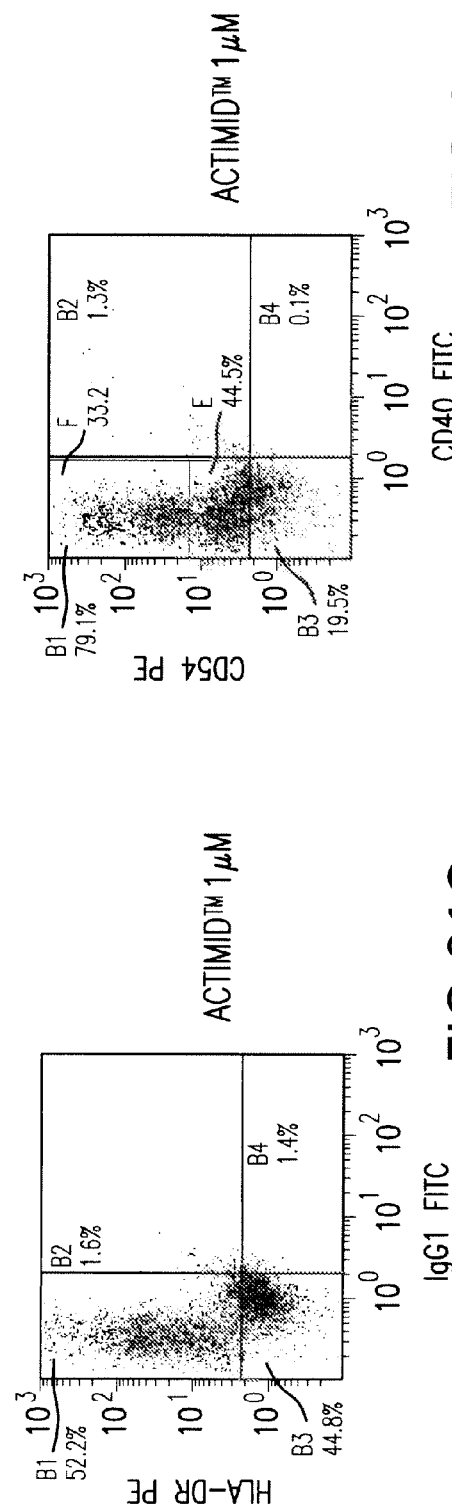

MODULATION OF STEM AND PROGENITOR CELL DIFFERENTIATION, ASSAYS, AND USES THEREOF

CROSS REFERENCE TO RELATED APPLICATIONS

This application is a divisional application of U.S. application Ser. No. 10/411,655, filed Apr. 11, 2003 now U.S. Pat. No. 7,498,171, which claims benefit of U.S. Provisional Application Nos. 60/372,348, filed Apr. 12, 2002; 60/437,348, filed Dec. 31, 2002; and 60/437,350, filed Dec. 31, 2002, each of which is incorporated herein by reference in its entirety.

1. INTRODUCTION

The present invention relates to methods of modulating mammalian stem and/or progenitor cell differentiation. The methods of the invention can be employed to regulate and control the differentiation and maturation of mammalian, particularly human, stem and progenitor cells along specific cell and tissue lineages. The methods of the invention relate to the use of certain small organic molecules to modulate the differentiation of stem cell populations along specific cell and tissue lineages, and in particular, to the differentiation of embryonic-like stem cells originating from a postpartum placenta or the modulation of early hematopoietic progenitor cells along a specific differentiation pathway, particularly a granulocytic differentiation pathway. The invention also relates to the use of these organic molecules to modulate the differentiation of particular lineages of progenitor cells, such as CD34+, CD45+ and CD133+ progenitor cells. The invention also relates to the temporal aspects of progenitor cell development, and in vitro models based upon these temporal aspects. The invention further relates to the use of these modulated cells in prophylactic and therapeutic methods, including in pharmaceutical compositions of such cells and/or small organic compounds. Finally, the invention relates to the use of such differentiated cells in transplantation and other medical treatments.

2. BACKGROUND OF THE INVENTION

There is considerable interest in the identification, isolation and generation of human stem and progenitor cells. Stem cells are totipotential or pluripotential precursor cells capable of generating a variety of mature cell lineages, and precursor cells are cells capable of generating cells of specific cell lineages. These abilities serve as the basis for the cellular differentiation and specialization necessary for organ and tissue development.

Recent success at transplanting stem and progenitor cells have provided new clinical tools to reconstitute and/or supplement bone marrow after myeloablation due to disease, exposure to toxic chemical and/or radiation. Further evidence exists that demonstrates that stem cells can be employed to repopulate many, if not all, tissues and restore physiologic and anatomic functionality. The application of stem cells in tissue engineering, gene therapy delivery and cell therapeutics is also advancing rapidly.

Many different types of mammalian and progenitor stem cells have been characterized. For example, embryonic stem cells, embryonic germ cells, adult stem cells or committed stem cells or progenitor cells are known. Certain stem cells have not only been isolated and characterized but have also been cultured under conditions to allow differentiation to a limited extent. However, a basic problem remains; that is, it has been difficult to control or regulate the differentiation of stem cells and progenitor cells, such as hematopoietic progenitor cells. Presently, existing methods of modulating the differentiation of these cells are crude and unregulatable, such that the cells differentiate into unwanted cell types, at unwanted times. Moreover, the yield of the product cells is typically low.

Furthermore, obtaining sufficient numbers of human stem cells for therapeutic or research purposes is problematic. Isolation of normally occurring populations of stem or progenitor cells in adult tissues has been technically difficult and costly, due, in part, to the limited quantity of stem or progenitor cells found in blood or tissue, and the significant discomfort involved in obtaining bone marrow aspirates. In general, harvesting of stem or progenitor cells from alternative sources in adequate amounts for therapeutic and research purposes is generally laborious, involving, e.g., harvesting of cells or tissues from a donor subject or patient, culturing and/or propagation of cells in vitro, dissection, etc. With respect to stem cells in particular, procurement of these cells from embryos or fetal tissue, including abortuses, has raised religious and ethical concerns. The widely held belief that the human embryo and fetus constitute independent life has prompted governmental restrictions on the use of such sources for all purposes, including medical research. Alternative sources that do not require the use of cells procured from embryonic or fetal tissue are therefore desired for further progress in the use of stem cells clinically. There are, however, few viable alternative sources of stem or progenitor cells, particularly human stem or progenitor cells, and thus the supply is limited.

Hu et at (WO 00/73421 entitled "Methods of isolation, cryopreservation, and therapeutic use of human amniotic epithelial cells," published Dec. 7, 2000) discloses human amniotic epithelial cells derived from placenta at delivery that are isolated, cultured, cryopreserved for future use, or induced to differentiate. According to Hu et al., a placenta is harvested immediately after delivery and the amniotic membrane separated from the chorion, e.g., by dissection. Amniotic epithelial cells are isolated from the amniotic membrane according to standard cell isolation techniques. The disclosed cells can be cultured in various media, expanded in culture, cryopreserved, or induced to differentiate. Hu et al. discloses that amniotic epithelial cells are multipotential (and possibly pluripotential), and can differentiate into epithelial tissues such as corneal surface epithelium or vaginal epithelium. The drawback of such methods, however, is that they are labor-intensive and the yield of stem cells is very low.

Currently available methods for the ex vivo expansion of cell populations are also labor-intensive. For example, Emerson et al. (Emerson et al., U.S. Pat. No. 6,326,198 entitled "Methods and compositions for the ex vivo replication of stem cells, for the optimization of hematopoietic progenitor cell cultures, and for increasing the metabolism, GM-CSF secretion and/or IL-6 secretion of human stromal cells", issued Dec. 4, 2001); discloses methods, and culture media conditions for ex vivo culturing of human stem cell division and/or the optimization of human hematopoietic progenitor stem cells. According to the disclosed methods, human stem cells or progenitor cells derived from bone marrow are cultured in a liquid culture medium that is replaced, preferably perfused, either continuously or periodically, at a rate of 1 ml of medium per ml of culture per about 24 to about 48 hour period. Metabolic products are removed and depleted nutrients replenished while maintaining the culture under physiologically acceptable conditions.

Kraus et al. (Kraus et al, U.S. Pat. No. 6,338,942, entitled "Selective expansion of target cell populations," issued Jan. 15, 2002) discloses that a predetermined target population of cells may be selectively expanded by introducing a starting sample of cells from cord blood or peripheral blood into a growth medium, causing cells of the target cell population to divide, and contacting the cells in the growth medium with a selection element comprising binding molecules with specific affinity (such as a monoclonal antibody for CD34) for a predetermined population of cells (such as CD34 cells), so as to select cells of the predetermined target population from other cells in the growth medium.

Rodgers et al. (U.S. Pat. No. 6,335,195 entitled "Method for promoting hematopoietic and mesenchymal cell proliferation and differentiation," issued Jan. 1, 2002) discloses methods for ex vivo culture of hematopoietic and mesenchymal stem cells and the induction of lineage-specific cell proliferation and differentiation by growth in the presence of angiotensinogen, angiotensin I (AI), AI analogues, AI fragments and analogues thereof, angiotensin II (AII), All analogues, All fragments or analogues thereof or All $AT_2$ type 2 receptor agonists, either alone or in combination with other growth factors and cytokines. The stem cells are derived from bone marrow, peripheral blood or umbilical cord blood. The drawback of such methods, however, is that such ex vivo methods for inducing proliferation and differentiation of stem cells are time-consuming, as discussed above, and also result in low yields of stem cells.

Stem and progenitor cells have the potential to be used in the treatment of a variety of disorders, including malignancies, inborn errors of metabolism, hemoglobinopathies, and immunodeficiencies. One major area of use and research involving stem cells from cord blood or placenta has been the use of such cells to generate small quantities of cells for bone marrow and other related transplantations. However, to date, no one has described a method of producing substantial numbers of stem or progenitor cells, such as human $CD34^+$ or $CD133^+$ progenitor cells. Large numbers of the latter cells, in particular, would facilitate treatment methods using progenitor cells. The methods of the invention disclosed herein addresses this need.

Retinoids, such as vitamin A and retinoic acid (RA), have been known to affect differentiation of stem cells. For example, retinoic acid has been shown to inhibit proliferation of abnormally committed (chronic myelogenous leukemia) hematopoietic stem cells (Nadkarni et al. 1984, Tumori 70:503-505) and to induce differentiation and loss of self-renewal potential in promyelocytic leukemia cells (Melchner et al., 1985, Blood 66(6): 1469-1472). Retinoic acid has also been shown to induce differentiation of neurons from embryonic stem cells and to repress spontaneous mesodermal differentiation (Slager et al., Dev. Genet. 1993; 14(3):212-24, Ray et al., 1997, J. Biol. Chem. 272(30): 18702-18708). Retinoic acid has further been shown to induce differentiation of transformed germ cell precursors (Damjanov et al., 1993, Labor. Investig. 68(2):220-232), placental cell precursors (Yan et al., 2001, Devel. Biol. 235: 422-432), and endothelial cell precursors (Hatzopoulos et al., 1998, Development 125: 1457-1468). The effect of retinoids on differentiation, however, has yet to be completely understood such that it could be used as a regulatable means of controlling differentiation of stem cells.

The effects of folic acid analogues, such as aminopterin and amethopterin (methotrexate), on the differentiation of hematopoietic stem cells has been studied. Folic acid analogues are used as chemotherapeutic agents in acute lymphoblastic anemias and other blood proliferation disorders and cancers, and have been shown to effect differentiation of stem cells by killing off certain populations of stem cells (DeLoia et al., 1998, Human Reproduction 13(4): 1063-1069), and thus, would not be an effective tool for regulating differentiation of large quantities of stem cells for administration to a patient.

Several cytokines, such as IL-1, IL-2, IL-3, IL-6, IL-7, IL-11, as well as proteins such as erythropoietin, Kit ligand, M-CSF and GM-CSF have also been shown to direct differentiation of stem cells into specific cell types in the hematopoietic lineage (Dushnik-Levinson et al., 1995, Biol. Neonate 67:77-83), however, these processes are not well understood and still remain too crude and imprecise to allow for a regulatable means of controlling differentiation of stem cells.

To date, no one has described the use of compounds, such as the immunomodulatory compounds discussed below, in the differentiation of stem cells or precursor cells. In particular, no one has demonstrated the use of such compounds to modulate the differentiation of progenitor cells, such as $CD34^+$ progenitor cells, away from a dendritic cell lineage, a capability useful in encouraging transplant immune tolerance. Likewise, no one has described the use of the compounds described herein to expand the progenitor cell populations so as to produce a pharmaceutical composition containing such cells. Such expanded progenitor cell cultures would be useful in the treatment of graft-versus-host disease and the development of immune tolerance. Because control over stem and precursor cell differentiation can produce cell populations that are therapeutically useful, there is a need for the ability to control and regulate the differentiation of cells of myeloid dendritic cell lineage, or early progenitor cells, such as human $CD34^+$ or $CD133^+$ progenitor cells, for the controlled production of dendritic cells and/or granulocytes.

3. SUMMARY OF THE INVENTION

The present invention provides methods of modulating mammalian, particularly human stem cell or progenitor cell differentiation. In particular, the methods of the invention may be employed to regulate and control the differentiation and maturation of human stem cells along specific cell and tissue lineages. The invention encompasses the use of immunomodulatory small organic compounds, more preferably amino-substituted isoindolines, particularly the compounds ACTIMID™ or REVIMID™, to effect such regulation and control. The invention further contemplated administration of these compounds to progenitor cells at specific times to modulate their differentiation in specific ways.

The methods of the invention encompass the regulation of differentiation of a stem cell or progenitor cell into a specific cell lineage, including, but not limited to, a mesenchymal, hematopoietic, adipogenic, hepatogenic, neurogenic, gliogenic, chondrogenic, vasogenic, myogenic, chondrogenic, or osteogenic lineage. In particular embodiment, the methods of the invention encompass the regulation of stem cell differentiation to a cell of a hematopoietic lineage.

The invention also encompasses the modulation of a committed cell to a specific cell type, e.g., mesenchymal cell, hematopoietic cell, adipocyte, hepatocyte, neuroblast, glioblast, chondrocyte, endothelial cell (EC) progenitor, myocyte, chondrocyte, or osteoblast. In specific embodiments, the invention encompasses the modulation of a committed hematopoietic progenitor cell to an erythrocyte, a thrombocyte, or a leukocyte (white blood cell) such as a neutrophil, monocyte, macrophage, eosinophil, basophil, mast cell, B-cell, T-cell, or plasma cell.

In another embodiment, the methods of the invention relate to modulating the differentiation of stem cells to cells of a hematopoietic lineage, in particular, CD34+, CD 133+, and CD45+ hematopoietic lineages, and methods of producing prophylactically or therapeutically beneficial pharmaceutical compositions containing such cells. In another specific embodiment, the methods of the invention relate to modulating the differentiation of early progenitor cells into cells of a dendritic cell lineage or a granulocyte lineage, endothelial lineage, or cardiomyocyte lineage.

In another embodiment, the invention provides methods for regulating the differentiation of a progenitor cell into a hematopoietic lineage, particularly a dendritic cell or granulocytic lineage, endothelial lineage, neural lineage or cardiomyocyte lineage. In a specific embodiment, said progenitor cell is a CD34+ or CD133+ cell. Such regulation is accomplished by contacting the progenitor cells during culture with a compound of the invention. In one embodiment, said compound in an inhibitor of TNF-α activity. In a more specific embodiment, said compound is an immunomodulatory compound as described herein, or thalidomide or, more preferably, an amino-substituted isoindoline. In an even more specific embodiment, said compound is ACTIMID™ or REVIMID™

In another specific embodiment, the methods of the invention encompass the suppression of progenitor cell differentiation into a dendritic cell. In another specific embodiment, the invention provides a method for modulating the differentiation of progenitor cells during the first six days of culture to produce an expanded culture of such progenitor cells. In another embodiment, the methods of the invention encompass the promotion of early progenitor cell development into a granulocyte, which may be useful for fighting infections. The increase of granulocyte lineage committed progenitors ($CD15^+$ cells) can be of potential use in the reduction of neutropenia and its subsequent infectious complications that represent the most common dose-limiting toxicity of cancer chemotherapy. In another embodiment, the methods of the invention may be used to suppress dendritic cell differentiation, which is useful for mitigating the effects of graft-versus-host disease.

The progenitor cells of the invention, as modulated by a compound of the invention, are useful for transplantation (i.e., hematopoietic reconstitution), and may be used in regenerative medicine as a renewable source of replacement cells and tissues (such as pancreatic, cardiac, hepatic, kidney, liver, brain, lung, bladder, intestinal or muscle cells) to treat normal senescence, injury or diseases such as heart disease, stroke, Parkinson's disease, and Alzheimer's disease. The cells will also be useful in the determination of the intracellular biochemical pathways that mediate the action of the compounds of the invention. These cells may also be useful for the screening of new drugs and toxins, for example, to determine potential anti-cancer drugs, to understand the origins of birth defects, etc.

The methods of the invention may be used to suppress specifically the generation of red blood cells or erythropoietic colonies (BFU-E and CFU-E), while augmenting both the generation of leukocyte and platelet forming colonies (CFU-GM) and enhancing total colony forming unit production. The methods of the invention may be used not only to regulate the differentiation of stem cells, and progenitor cells such as CD34+ progenitor cells, but may also be used to stimulate the rate of colony formation, providing significant benefits to hematopoietic stem cell transplantation by improving the speed of bone marrow engraftment.

Any mammalian stem cell can be used in accordance with the methods of the invention, including but not limited to, stem cells isolated from cord blood, placenta and other sources. The stem cells may be isolated from any mammalian species, e.g., mouse, rat, rabbit, guinea pig, dog, cat, pig, sheep, cow, horse, monkey, etc., more preferably, a human. The stem cells may include pluripotent cells, i.e., cells that have complete differentiation versatility, that are self-renewing, and can remain dormant or quiescent within tissue. The stem cells may also include multipotent cells or committed progenitor cells. In one preferred embodiment, the invention utilizes stem cells that are viable, quiescent, pluripotent stem cells that exist within, or are later produced by, the full-term placenta, that is, such cells can be recovered following successful birth and placental expulsion, exsanguination and perfusion of the placenta, resulting in the production and recovery of as many as one billion nucleated cells, which yield 50 to 100 million multipotent and pluripotent stem cells. Such cells are referred to herein as human placental stem cells or embryonic-like stem cells.

In one particular embodiment of the invention, cells, for example cells endogenous to bone marrow or to a postpartum perfused placenta, including, but not limited to, embryonic-like stem cells, progenitor cells such as CD34+ or CD133+ cells, pluripotent cells and multipotent cells, are exposed to the compounds of the invention and induced to differentiate. The endogenous cells may be propagated in vitro. In another embodiment, the endogenous cells may be collected from the placenta and culture medium and cultured in vitro under conditions appropriate, and for a time sufficient, to induce differentiation to the desired cell type or lineage.

In another embodiment of the invention, the stem or progenitor cells are derived from other sources such as cord blood, peripheral blood or adult blood, and are exposed to the compounds of the invention and induced to differentiate. In a preferred embodiment, the differentiation is conducted in vitro under conditions appropriate, and for a time sufficient, to induce differentiation into the desired lineage or cell type. The compounds of the invention are used in the differentiation/culture media by addition, in situ generation, or in any other manner that permits contact of the stem or progenitor cells with the compounds of the invention.

It has been discovered that the timing of the administration of the compounds of the invention have a profound impact upon the differentiation of $CD34^+$ progenitor cells. Thus, in one embodiment of the invention, differentiation of $CD34^+$ progenitor cells into dendritic cells is delayed or suppressed by a method comprising contacting the progenitor cell on the first day of culture with a compound of the invention. In another embodiment, the development of $CD1a^+$ cells from $CD34^+$ progenitor cells is reduced or prevented by a method comprising contacting said progenitor cells with a compound of the invention on the first day of culture. In another embodiment, the persistence of a $CD1a^+$ cell population derived from $CD34^+$ progenitor cells is increased by contacting said progenitor cells with a compound of the invention after culturing said progenitor cells for six days in the absence of said compound.

The present invention also encompasses methods of modulating the differentiation of early progenitor cells, such as human $CD34^+$ and $CD133^+$ cells, comprising contacting the progenitor cells at various times during the proliferative and differentiative phases with one or more of the compound(s) of the invention. Thus, in one embodiment, the invention encompasses a method of modulating the differentiation of the progenitor cells comprising contacting said cells with one or more compound(s) of the invention on the first day of culture only. In another embodiment, said cells are contacted with said compound(s) in one dose on any day between the first day and the twelfth day of culture. In another embodiment, said cells are contacted at least two times with said compound(s), on different days, between days 0-12, inclusive. In yet another embodiment, said cells are contacted with one or more compound(s) twice a day, once a day, or once every other day during the proliferative and/or differentiation phases. In another embodiment, said contacting is performed in vitro. In yet another embodiment, said contacting is performed in vivo in a subject. In a more specific embodiment, said subject is a human, a non-human mammal, an bird or a reptile.

In sum, exposure of endogenous or exogenous stem or progenitor cells which may be cultured in a postpartum perfused placenta, to compounds of the invention may occur while the cells are cultured in the placenta, or preferably, may occur in vitro after the cells have been recovered and removed from the placenta.

The invention encompasses the use of compounds that have TNF-α activity as modulators of stem and/or progenitor cell development. In specific embodiments, the compounds are immunomodulatory compounds such as classes of compounds known as IMIDS®, including but not limited to thalidomide analogs, ACTIMID™ (Celgene Corp., Warren, N.J.), and REVIMID™ (Celgene Corp., Warren, N.J.).

The invention also encompasses the transplantation of pretreated stem or progenitor cells to treat or prevent disease. In one embodiment, a patient in need of transplantation is also administered a compound of the invention before, during and/or after transplantation.

The invention further encompasses the use of a progenitor cell or specific cell type produced from a method of the invention. In other words, the invention encompasses the use of leukocytes, granulocytes, or dendritic cells made from the differentiation of a hematopoietic progenitor wherever said differentiation of the progenitor as modulated or regulated using a compound of the invention.

In other embodiments, the invention encompasses the control or regulation of stem cells in vivo by the administration of both a stem cell and a small molecule compound of the invention to a patient in need thereof.

In one embodiment, the invention provides a pharmaceutical composition comprising CD34+ or CD133+ progenitor cells that have been contacted with a compound of the invention, particularly one that inhibits the activity of TNF-α, in the first six days of culture, under conditions that promote proliferation and differentiation of said progenitor cells, and a pharmaceutically-acceptable carrier. In a specific embodiment, the pharmaceutical composition includes cells that have been collected and cryopreserved after six days of culture. In another specific embodiment, the cells of the pharmaceutical composition are $CD34^+CD38^-CD34^-$ or $CD34^+ CD38^{31} CD34^+$ cells. In another specific embodiment, the compound with which the cells are contacted is an immunomodulatory compound of the invention, or thalidomide or a thalidomide analog. In another specific embodiment, the compound with which the cells are contacted is ACTIMID™ or REVIMID™.

In another embodiment, the invention also provides for method of making a pharmaceutical composition, comprising contacting CD34+ or CD133+ progenitor cells with a compound that inhibits TNF-α activity, wherein said progenitor cells are cultured for six days in a culture medium under culture conditions that allow proliferation and differentiation of said progenitor cells; collecting said cells after six days of culture; and combining said cells with a pharmaceutically-acceptable carrier. In a specific embodiment of this method, said contacting is performed on the first day of culture. In another specific embodiment of this method, said contacting is performed at least twice during said six days of culture. In another specific embodiment of this method, said compound is a small immunomodulatory compound of the invention. In another specific embodiment of this method, said compound is ACTIMID™ or REVIMID™. In yet another specific embodiment of this method, said progenitor cells have been isolated from other blood cells prior to said culturing. In another specific embodiment of this method, said culture medium additionally contains GM-CSF and TNF-α. In more specific embodiment of this method, said ACTIMID™ or REVIMID™ is present in a concentration of between 0.1 μM and 10.0 μM. In another more specific embodiment of this method, said ACTIMID™ or REVIMID™ is present at a concentration of 1.0 μM. In another specific embodiment of this method, said cells are cryopreserved after said collecting.

The invention further provides a method for expanding a progenitor cell population in a mammalian subject, comprising administering a therapeutically effective amount of CD34+ or CD133+ progenitor cells and either ACTIMID™ or REVIMID™ to said recipient mammalian subject. In specific embodiment of this method, said progenitor cells are differentiated in the recipient mammalian subject. In another specific embodiment of this method, said progenitor cells are administered to said subject in a cell preparation that is substantially free of red blood cells. In another specific embodiment of this method, said progenitor cells are administered to the recipient mammalian subject in a cell preparation that comprises bone marrow cells, placental cells, cord blood cells or PBMCs. In another specific embodiment of this method, said progenitor cells are administered to the recipient mammalian subject in conjunction with a carrier. In another specific embodiment of this method, said progenitor cell is a CD34+ CD133+ progenitor cell. In another specific embodiment of this method, the progenitor cells express incorporated genetic material of interest.

The present invention also provides the cells that are produced by the above methods that are useful as pharmaceutical compositions.

In yet other embodiments, the invention encompasses methods of conditioning stem cells or progenitor cells, for example, CD34+ progenitor cells, following cryopreservation and thawing, to counteract the deleterious effects of cryopreservation and exposure to cryopreservatives on the stem cells. In certain embodiments, the invention provides methods of conditioning stem cells following cryopreservation and thawing, to counteract the deleterious effects of exposure to cryopreservatives (e.g., DMSO) on the proliferative and migratory capacity of stem cells.

3.1. Definitions

As used herein, the term "bioreactor" refers to an ex vivo system for propagating cells, producing or expressing biological materials and growing or culturing cells tissues, organoids, viruses, proteins, polynucleotides and microorganisms.

As used herein, "DC cells" refers to dendritic cells.

As used herein, "early progenitor cell" means a CD34+ progenitor cell, a $CD133^+$ progenitor cell, or the mammalian, avian or reptilian equivalent of either.

As used herein, the term "embryonic stem cell" refers to a cell that is derived from the inner cell mass of a blastocyst (e.g., a 4- to 5-day-old human embryo) and that is pluripotent.

As used herein, the term "embryonic-like stem cell" refers to a cell that is not derived from the inner cell mass of a blastocyst. As used herein, an "embryonic-like stem cell"

may also be referred to as a "placental stem cell." An embryonic-like stem cell is preferably pluripotent. However, the stem cells which may be obtained from the placenta include embryonic-like stem cells, multipotent cells, and committed progenitor cells. According to the methods of the invention, embryonic-like stem cells derived from the placenta may be collected from the isolated placenta once it has been exsanguinated and perfused for a period of time sufficient to remove residual cells. Preferably, the embryonic-like stem cells are human, though they may be derived from any mammal.

As used herein, the term "exsanguinated" or "exsanguination," when used with respect to the placenta, refers to the removal and/or draining of substantially all cord blood from the placenta. In accordance with the present invention, exsanguination of the placenta can be achieved by, for example, but not by way of limitation, draining, gravity induced efflux, massaging, squeezing, pumping, etc. In a preferred embodiment, exsanguination of the placenta may further be achieved by perfusing, rinsing or flushing the placenta with a fluid that may or may not contain agents, such as anticoagulants, to aid in the exsanguination of the placenta.

As used herein, the term "perfuse" or "perfusion" refers to the act of pouring or passaging a fluid over or through an organ or tissue, preferably the passage of fluid through an organ or tissue with sufficient force or pressure to remove any residual cells, e.g., non-attached cells from the organ or tissue. As used herein, the term "perfusate" refers to the fluid collected following its passage through an organ or tissue. In a preferred embodiment, the perfusate contains one or more anticoagulants.

As used herein, the term "endogenous cell" refers to a "non-foreign" cell, i.e., a "self" or autologous cell, that is derived from the placenta.

As used herein, the term "exogenous cell" refers to a "foreign" cell, i.e., a heterologous cell (i.e., a "non-self" cell derived from a source other than the placental donor) or autologous cell (i.e., a "self" cell derived from the placental donor) that is-derived from an organ or tissue other than the placenta.

As used herein, "immunomodulatory compound" refers to the compounds disclosed in Section 5.3, below.

As used herein, the term "organoid" refers to an aggregation of one or more cell types assembled in superficial appearance or in actual structure as any organ or gland of a mammalian body, preferably the human body.

As used herein, the term "multipotent cell" refers to a cell that has the capacity to grow into any of subset of the mammalian body's approximately 260 cell types. Unlike a pluripotent cell, a multipotent cell does not have the capacity to form all off the cell types.

As used herein, the term "pluripotent cell" refers to a cell that has complete differentiation versatility, i.e., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), an embryonic stem cell cannot usually form a new blastocyst.

As used herein, the term "progenitor cell" refers to a cell that is committed to differentiate into a specific type of cell or to form a specific type of tissue.

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells.

As used herein, the term "totipotent cell" refers to a cell that is able to form a complete embryo (e.g., a blastocyst).

4. BRIEF DESCRIPTION OF THE FIGURES

FIG. 1. Bar graph indicating results of culturing cord blood CD34+ cells in the presence of Thalidomide (THD), ACTIMID™, and REVIMID™ at concentrations of 1 µg/ml and 10 µg/ml. An equal volume of DMSO was used as a negative control. Hematopoietic colonies of burst forming units-erythroid (BFU-E), colony forming units-erythroid (CFU-E), colony forming units-granulocyte macrophage (CFU-GM) and total numbers of colonies (CFU-Total) were scored under the light microscope at day 14 of culture. Y-axis: numbers of colonies. See Section 6.1 for details.

Figure 2:
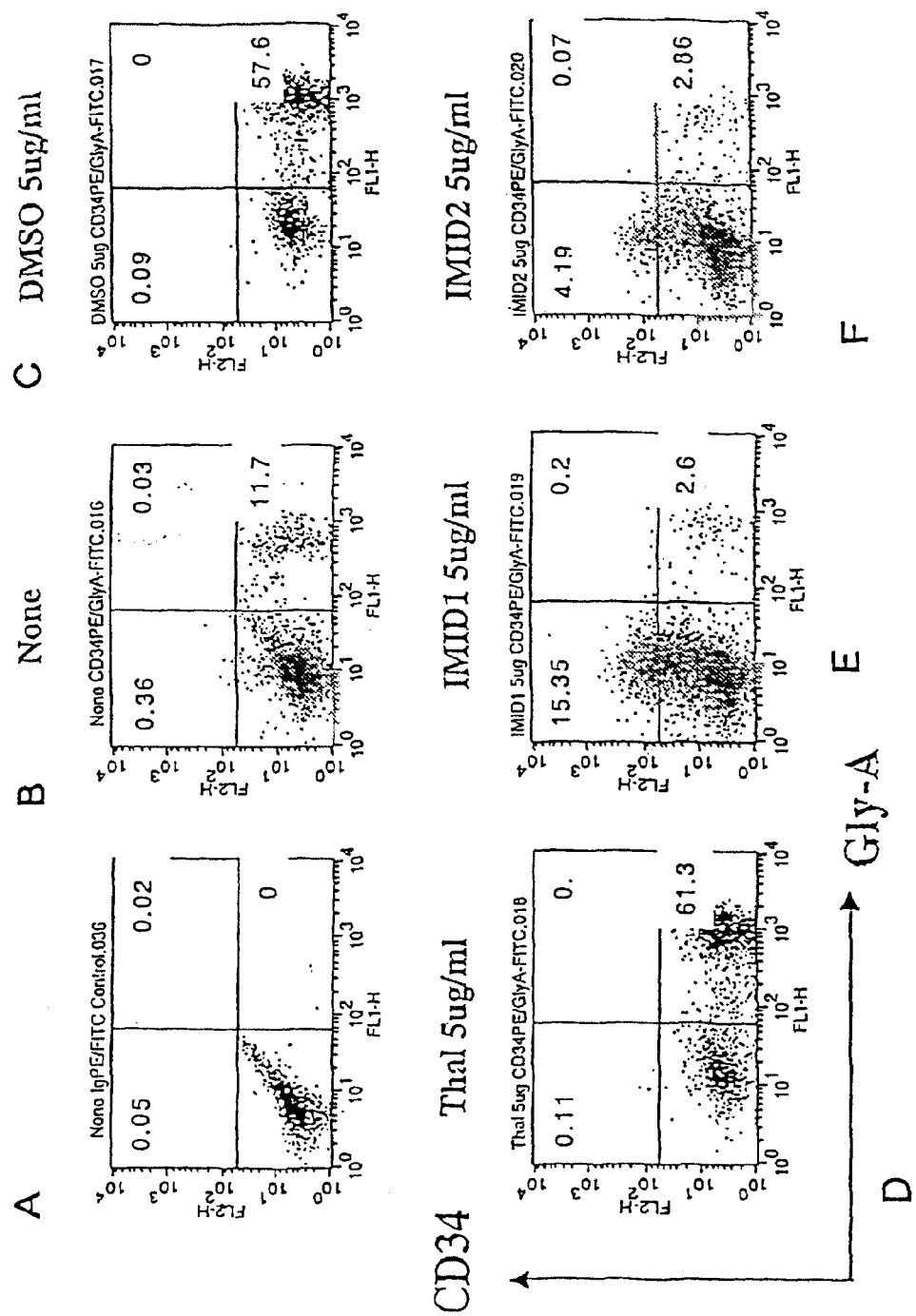

FIGS. 2(A-F). Flow cytograms. Exposure of human cord blood CD45+ cells to ACTIMID™ and REVIMID™ inhibits erythropoiesis and expansion of CD34+ CD38− cells. Cord blood CD45+ cells were cultured for 14 days with cytokines IL3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (5 µg/ml). D. Thalidomide ("Thal") (5 µg/ml). E. ACTIMID™ (5 µg/ml). F. REVIMID™ (5 µg/ml). X-axis: relative intensity of Gly-A (FL1-H) staining. Y-axis: relative intensity of CD34 (F 2-H) staining. See Section 6.1 for details.

Figure 3:
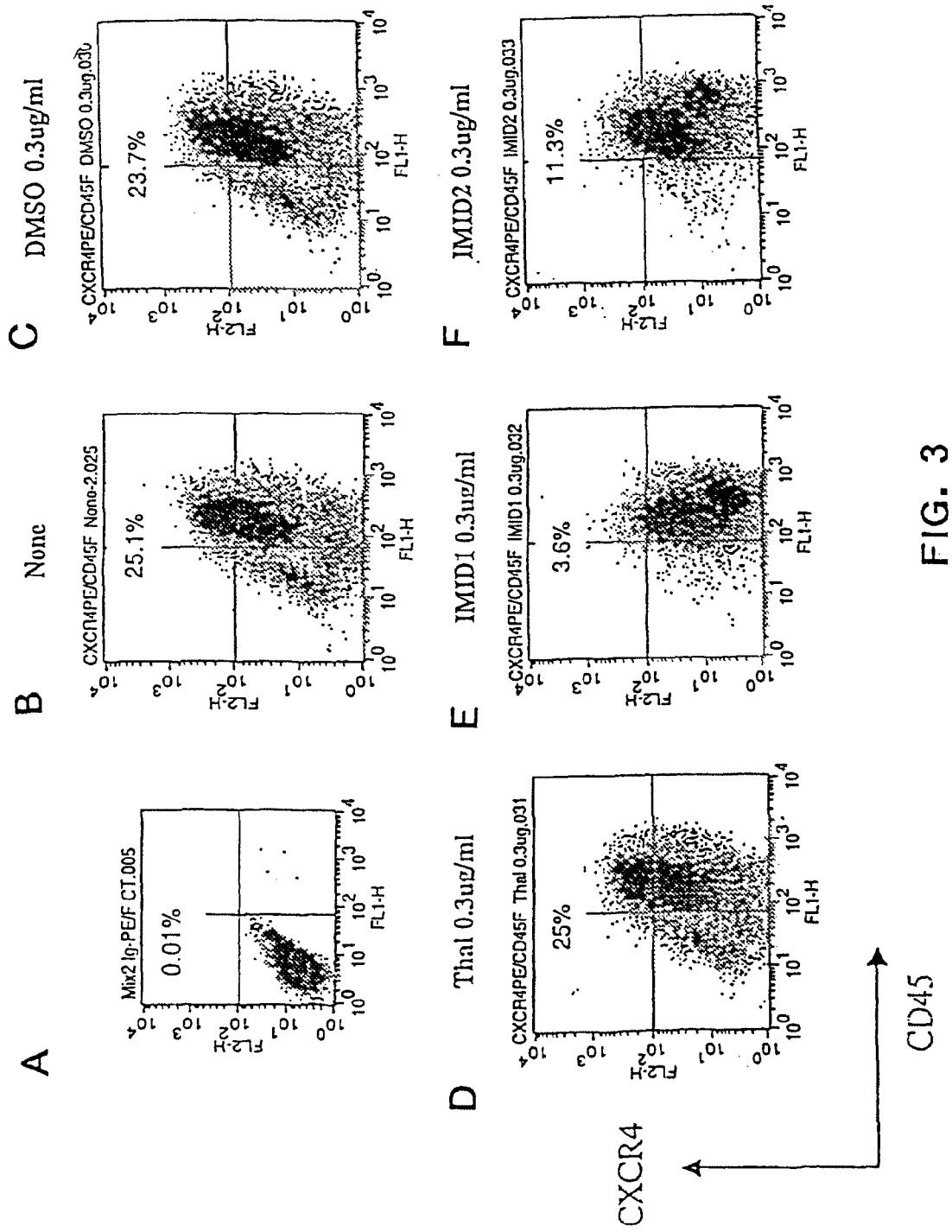

FIGS. 3(A-F). Flow cytograms. Exposure of human cord blood CD45+ cells to ACTIMID™ or REVIMID™ inhibits the expression of CXCR4 on human cord blood CD34+ cells in 14 days of culture with cytokines IL3, KL and G-CSF. Percentages indicated on each cytogram indicate the percentage of the cell population expressing a particular combination of markers. A. Control, immunoglobulin (Ig). B. Control, CD45+ cells. C. DMSO (0.3 µg/ml). D. Thal (0.3 µg/ml). E. ACTIMID™ (0.3 µg/ml). F. REVIMID™ (0.3 µg/ml). X-axis: relative intensity of CD34 (FL1-H) staining. Y-axis: relative intensity of CXCR4 (FL2-H) staining. See Section 6.2 for details.

Figure 4:
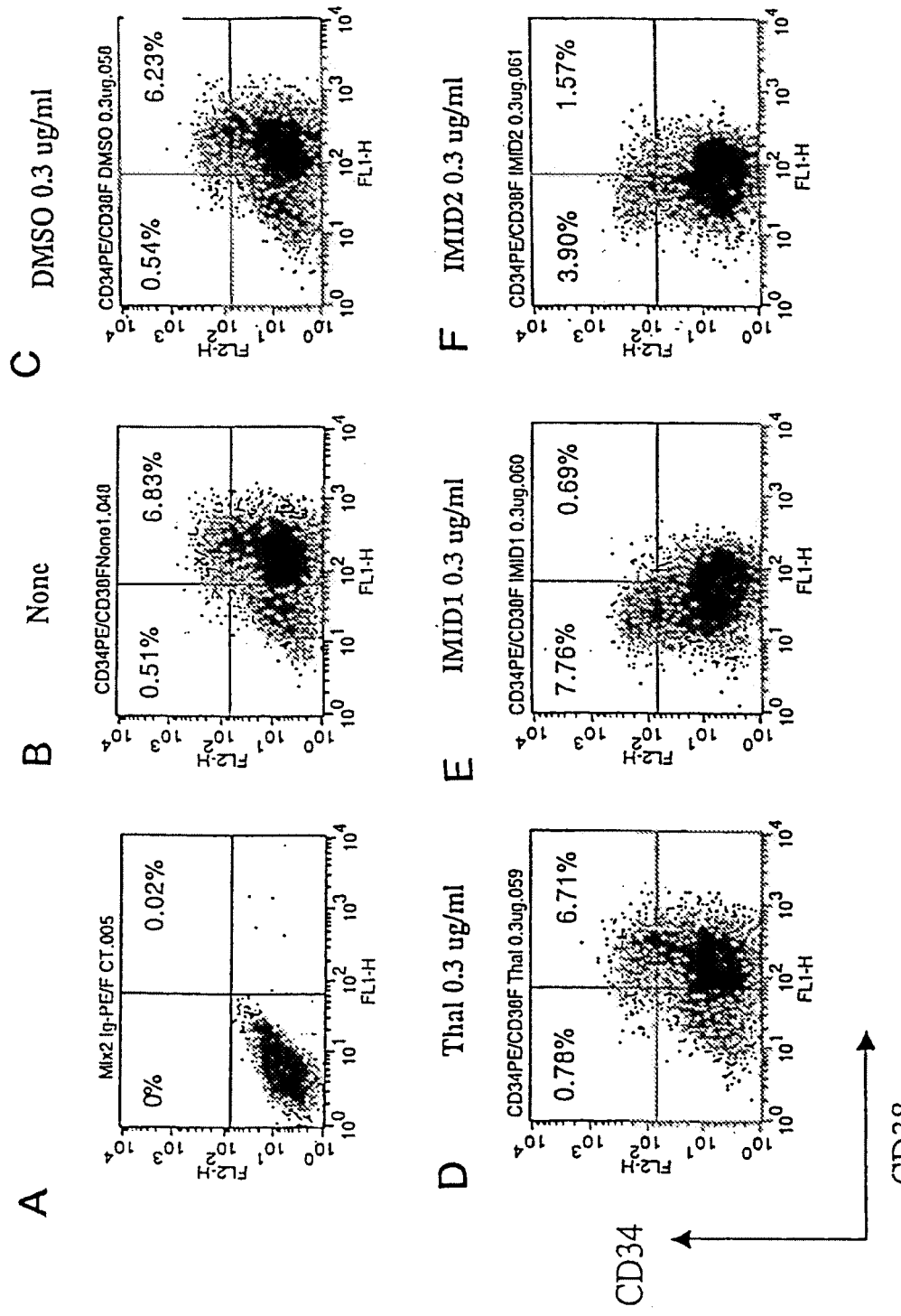

FIGS. 4(A-F). Flow cytograms. Exposure of human cord blood CD45+ cells to ACTIMID™ or REVIMID™ stimulates the expansion of CD34+ and/or CD34+CD38− cell populations. Cord blood CD45+ cells were cultured for 14 days with cytokines IL3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (0.3 µg/ml). D. Thal (0.3 µg/ml). E. ACTIMID™ (0.3 µg/ml). F. REVIMID™ (0.3 µg/ml). X-axis: relative intensity of CD 38 (FL1-H) staining. Y-axis: relative intensity of CD34 (FL2-H) staining. See Section 6.2 for details.

Figure 5:
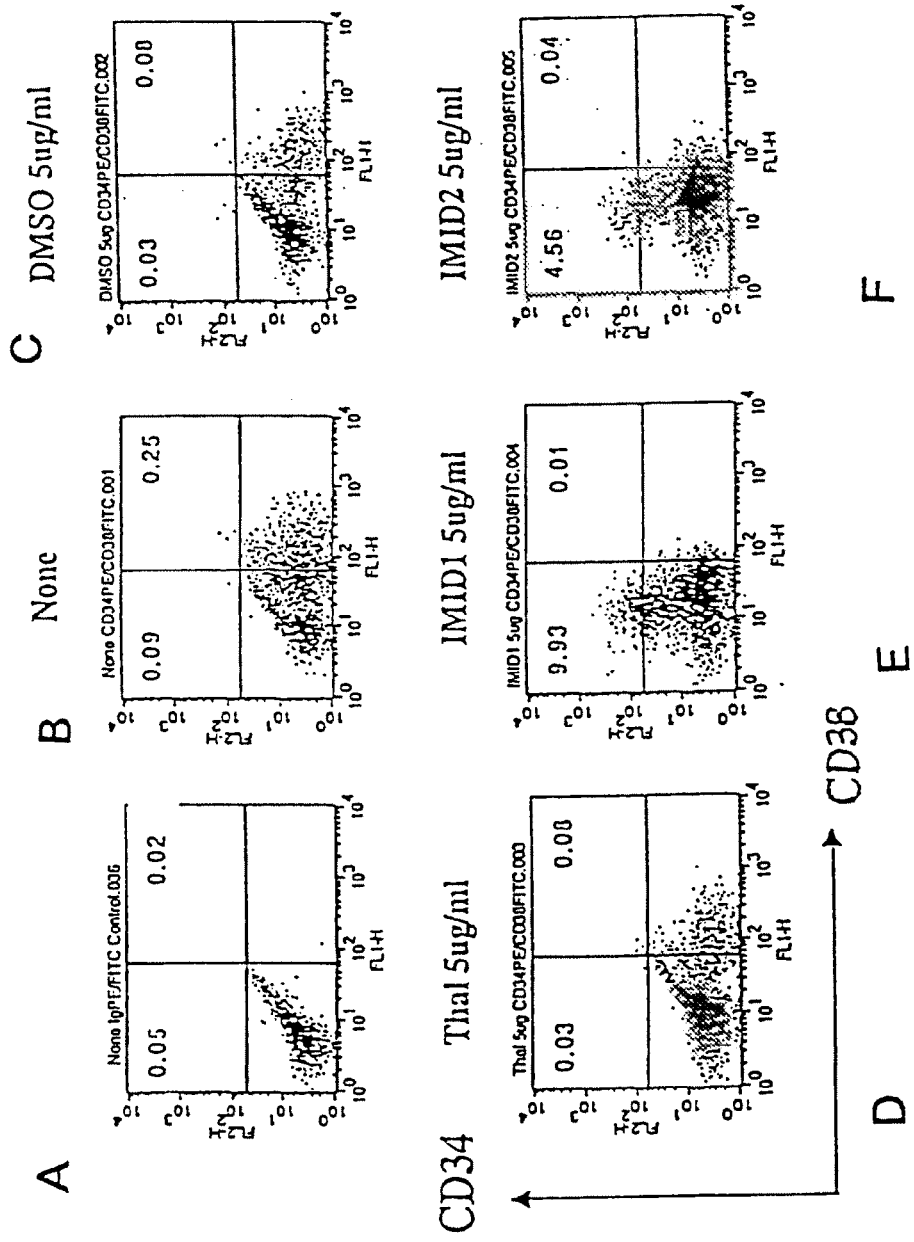

FIGS. 5(A-F). Flow cytograms. Exposure of human cord blood CD45+ cells to ACTIMID™ or REVIMID™ produces significant preservation of human cord blood progenitor cells. Cord blood CD45+ cells were cultured for 14 days with cytokines IL3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (5 µg/ml). D. Thal (5 µg/ml). E. ACTIMID™ (5 µg/ml). F. REVIMID™ (5 µg/ml). X-axis:

relative intensity of CD 38 (FL1-H) staining. Y-axis: relative intensity of CD34 (FL2-H) staining. See Section 6.2 for details.

Figure 6:
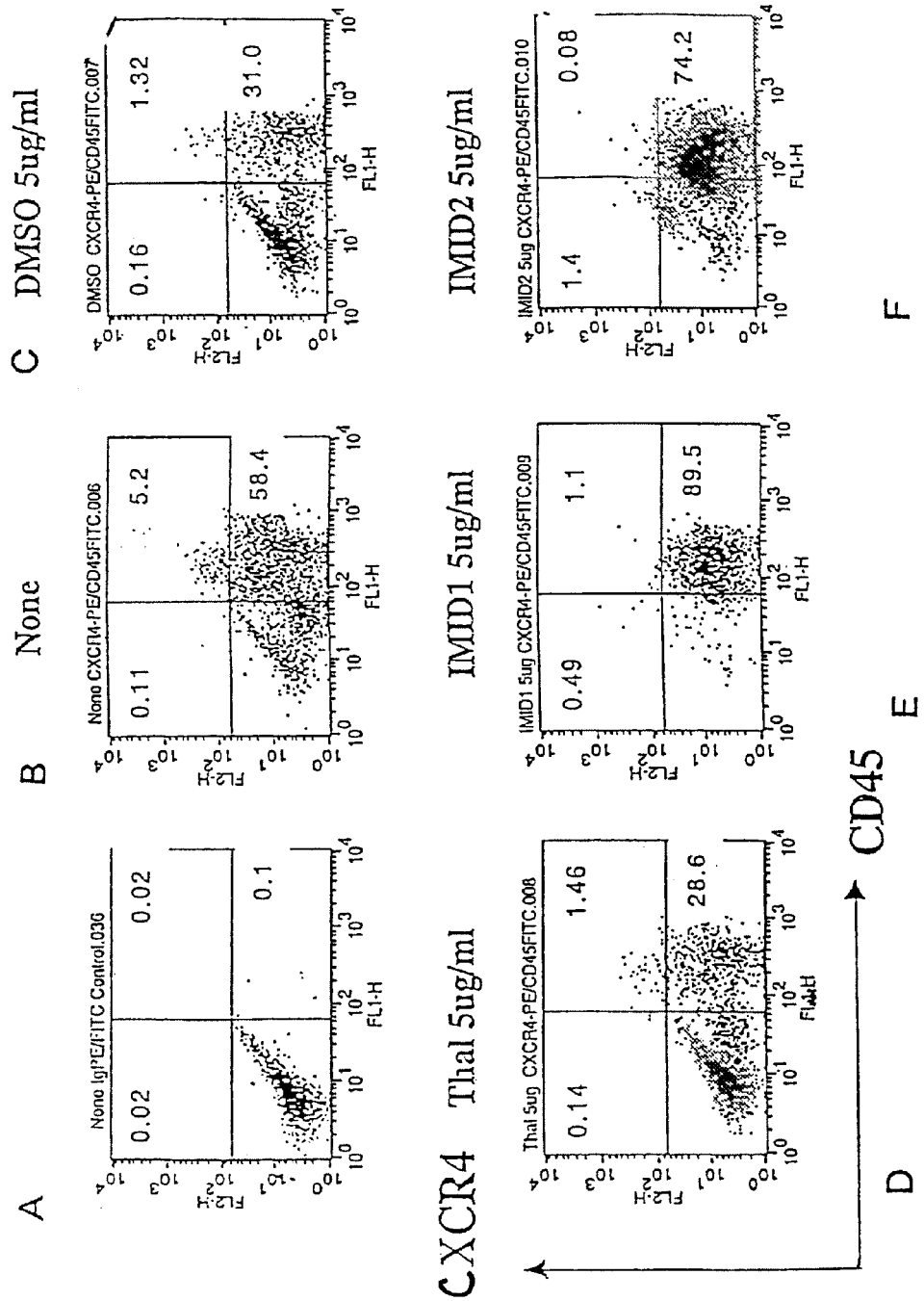

FIGS. 6(A-F). Flow cytograms. Exposure of human cord blood CD45+ cells to ACTIMID™ and REVIMID™ inhibits CXCR4 expression and expands the population of CD45+ cells. Cord blood CD45+ cells were cultured for 14 days with cytokines IL3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (5 µg/ml). D. Thal (5 µg/ml). E. ACTIMID™ (5 µg/ml). F. REVIMID™ (5 µg/ml). X-axis: relative intensity of CD45 (FL1-H) staining. Y-axis: relative intensity of CXCR4 (FL2-H) staining. See Section 6.2 for details.

Figure 7:
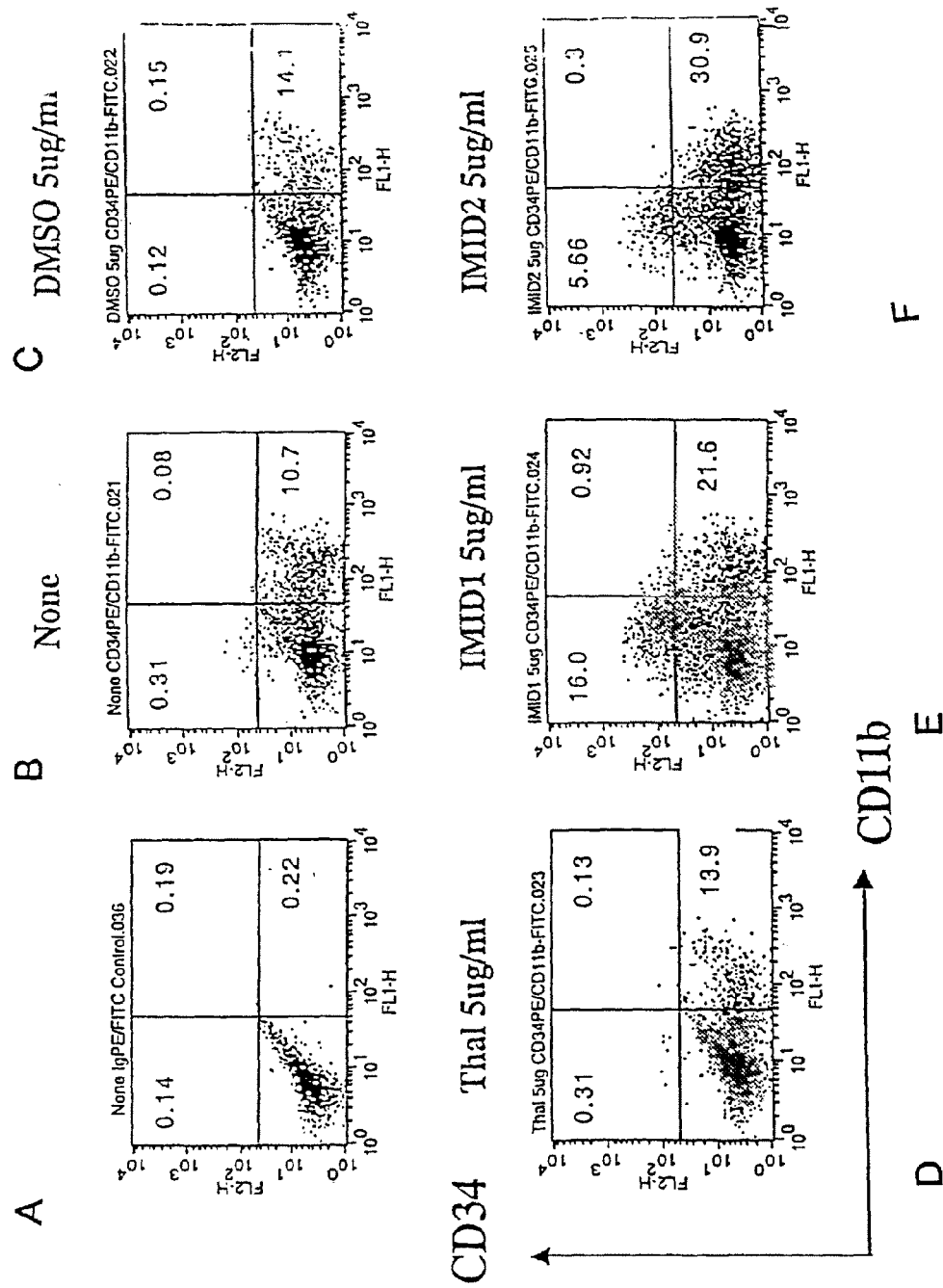

FIGS. 7(A-F). Flow cytograms. Exposure of human cord blood CD45+ cells to ACTIMID™ and REVIMID™ produces an expansion in number of CD34+ progenitor cells and increases production of granulocytes and monocytes. Cord blood CD45+ cells were cultured for 14 days with cytokines 1L3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (5 µg/ml). D. Thal (5 µg/ml). E. ACTIMID™ (5 µg/ml). F. REVIMID™ (5 µg/ml). X-axis: relative intensity of CD11b (FL1-H) staining. Y-axis: relative intensity of CD34 (FL2-H) staining. See Section 6.2 for details.

Figure 8:
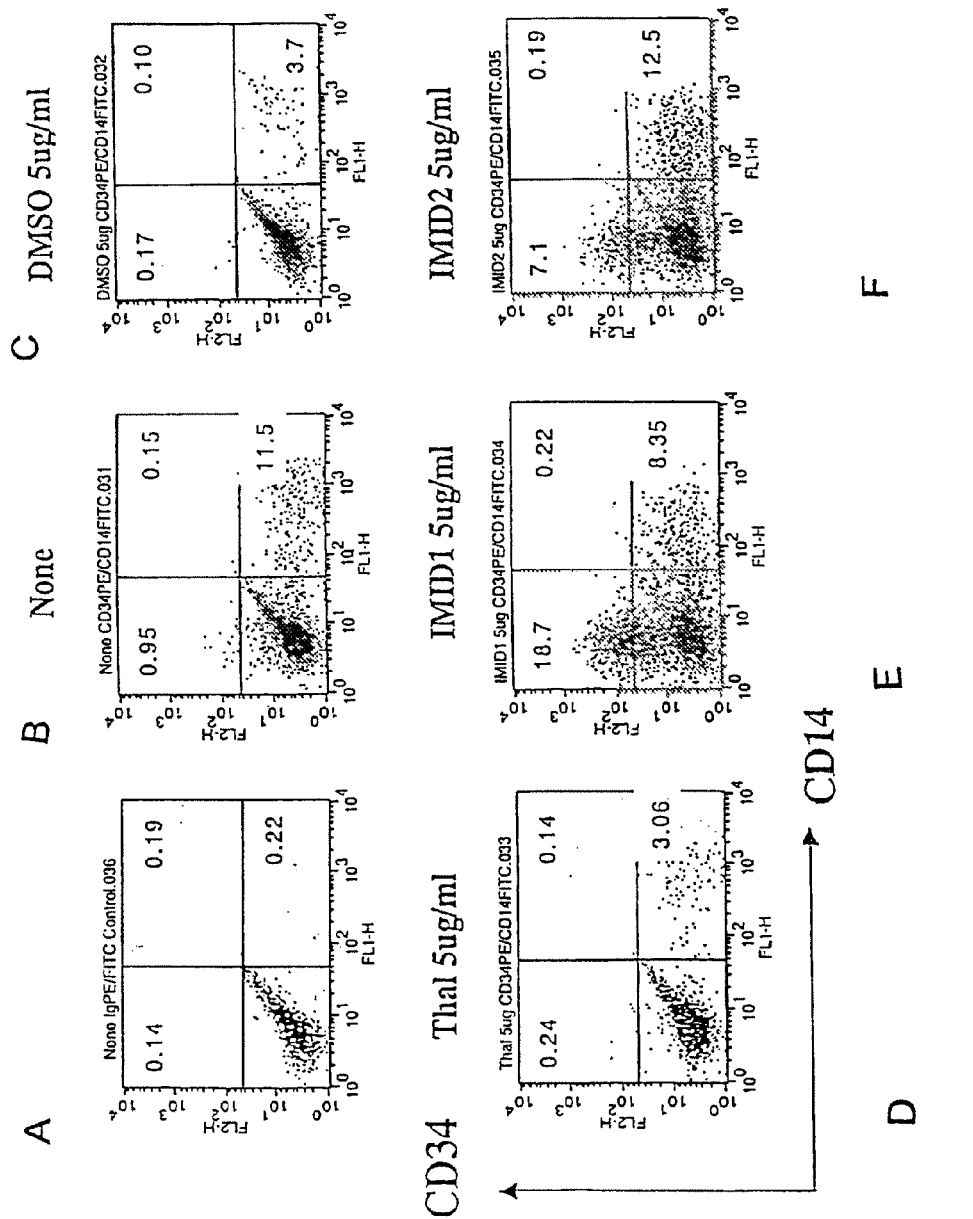

FIGS. 8(A-F). Flow cytograms. Exposure of human cord blood CD45+ cells to ACTIMID™ and REVIMID™ expands CD34+ progenitor cells and counteracts the DMSO-mediated repression of monocyte production. Cord blood CD45+ cells were cultured for 14 days with cytokines IL3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (5 µg/ml). D. Thal (5 µg/ml). E. ACTIMID™ (5 µg/ml). F. REVIMID™ (5 µg/ml). X-axis: relative intensity of CD 14 expression (FL1-H) staining. Maxis: relative intensity of CD34 (FL2-H) staining. See Section 6.3 for details.

Figure 9:
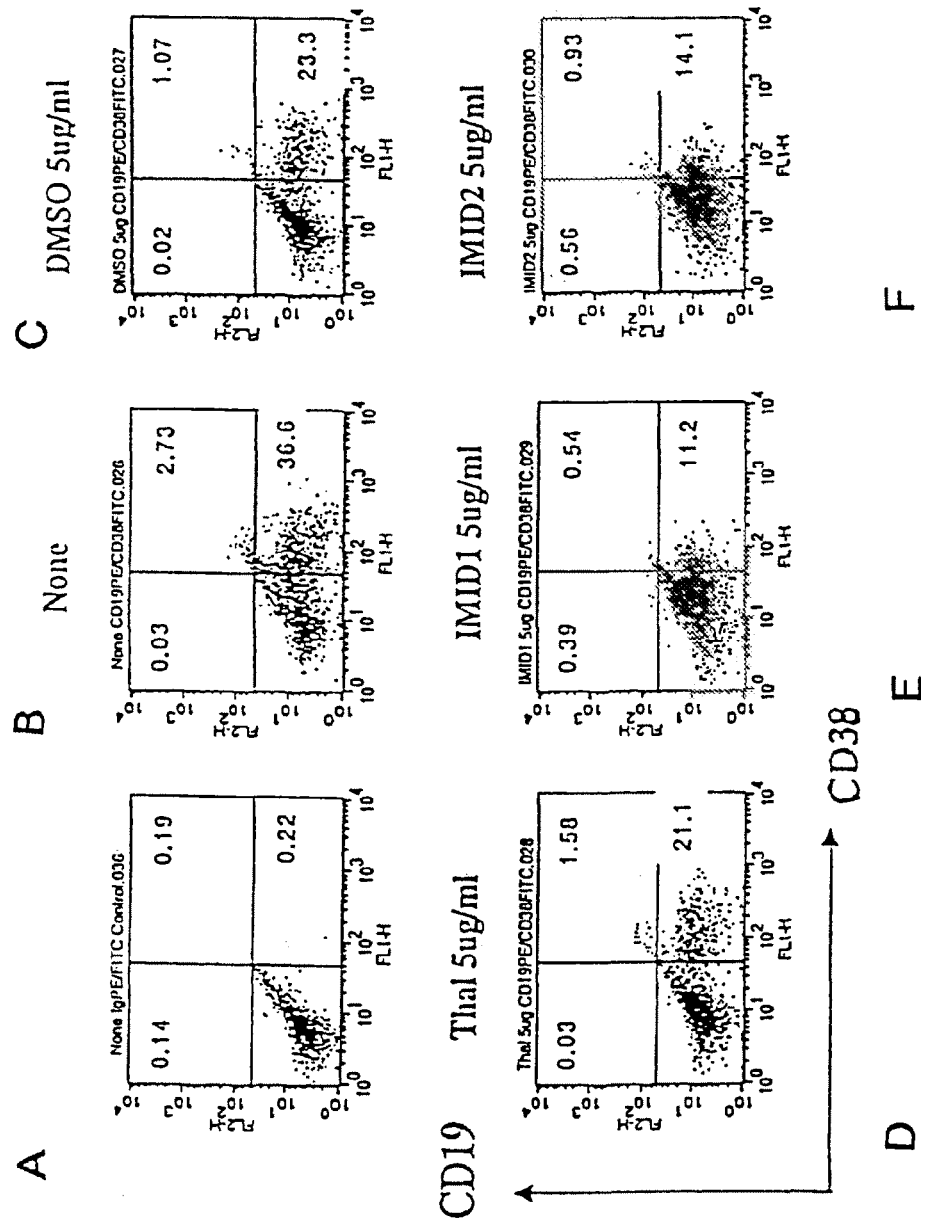

FIGS. 9(A-F). Flow cytograms. Exposure of human cord blood CD45+ cells to ACTIMID™ shows minor suppressive effects on the differentiation into B cells. Cord blood CD45+ cells were cultured for 14 days with cytokines IL3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (5 µg/ml). D. Thal (5 µg/ml). E. ACTIMID™ (5 µg/ml). F. REVIMID™ (5 µg/ml). X-axis: relative intensity of CD38 (FL1-H) staining. Y-axis: relative intensity of CD19 (FL2-H) staining. See Section 6.3 for details.

Figure 10:
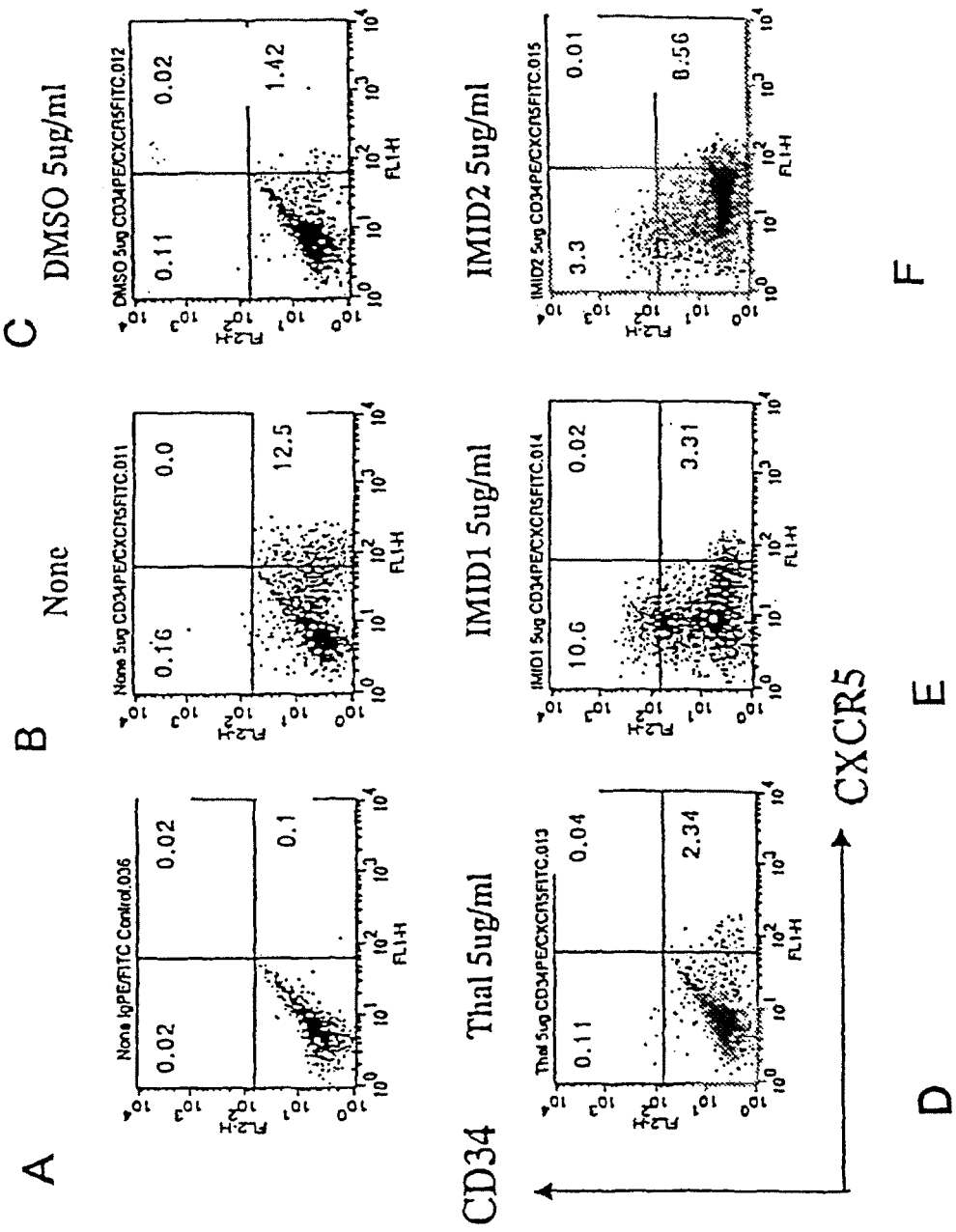

FIGS. 10(A-F). Flow cytograms. Exposure of human cord blood CD45+ cells to ACTIMID™ and REVIMID™ overcomes the repression of CXCR5 produced by exposure to DMSO. Cord blood CD45+ cells were cultured for 14 days with cytokines IL3, IL6, G-CSF, Epo and KL. Percentages indicated on each cytogram indicate the percentage of the cell population expressing a particular combination of markers. A. Control, immunoglobulin (Ig). B. Control, no compound added. C. DMSO (5 µg/ml). D. Thal (5 µg/ml). E. ACTIMID™ (5 µg/ml). F. REVIMID™ (5 µg/ml). X-axis: relative intensity of CXCR5 (FL1-H) staining. Y-axis: relative intensity of CD34 (FL2-H) staining. See Section 6.3 for details.

Figure 11:
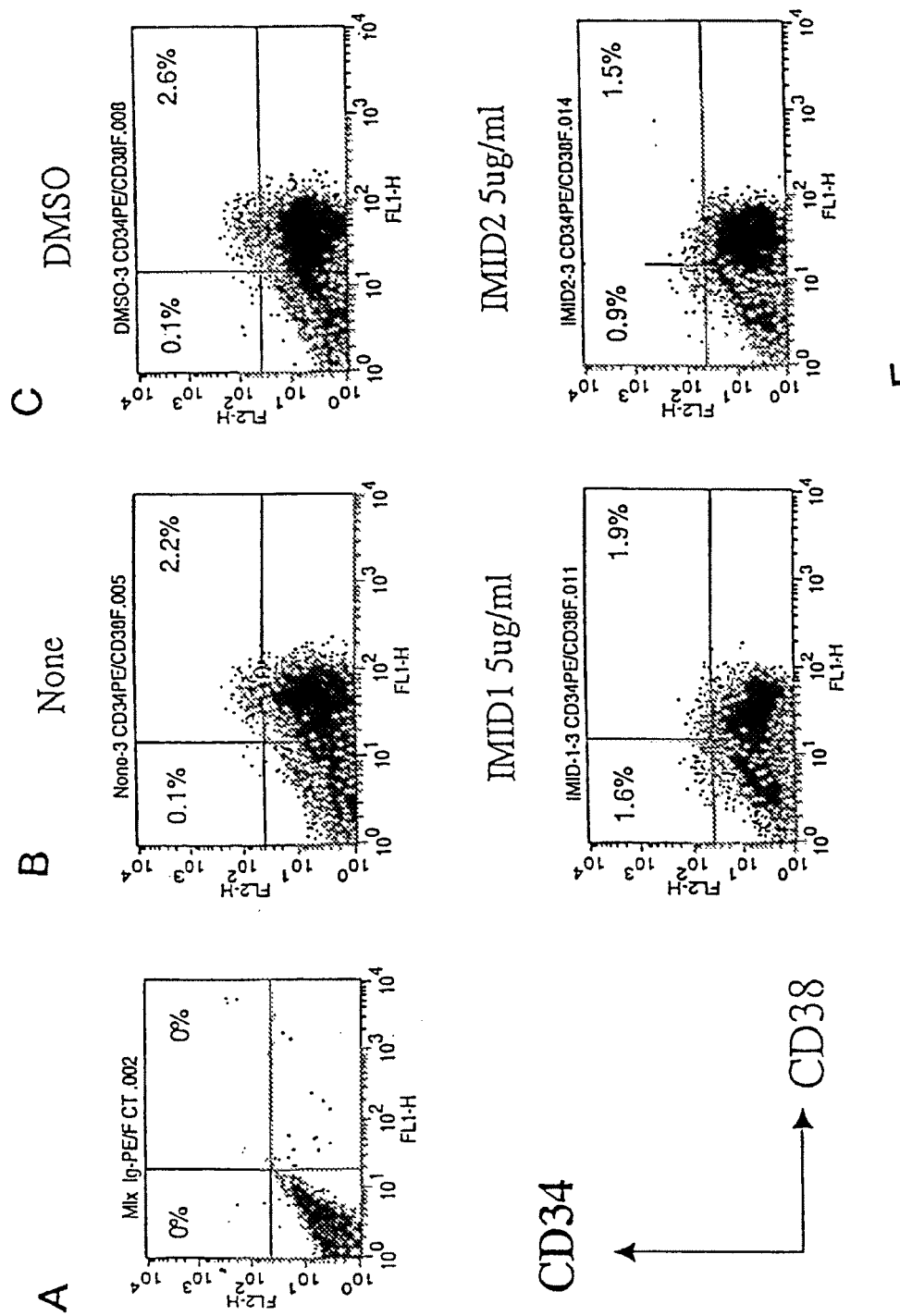

FIG. 11 (A-E). Flow cytograms. Exposure of human cord blood mononucleated cells (MNCs) to ACTIMID™ and REVIMID™ increases the CD34+CD38+ cell population. Percentages indicated on each cytogram indicate the percentage of the cell population expressing a particular combination of markers. A. Control, immunoglobulin (Ig). B. Control, no compound added. C. DMSO (5 µg/ml). D. ACTIMID™ (5 µg/ml). E. REVIMID™ (5 µg/ml). X-axis: relative intensity of CD38 (FL1-H) staining. Y-axis: relative intensity of CD34 (FL2-H) staining. See Section 6.3 for details.

Figure 12:
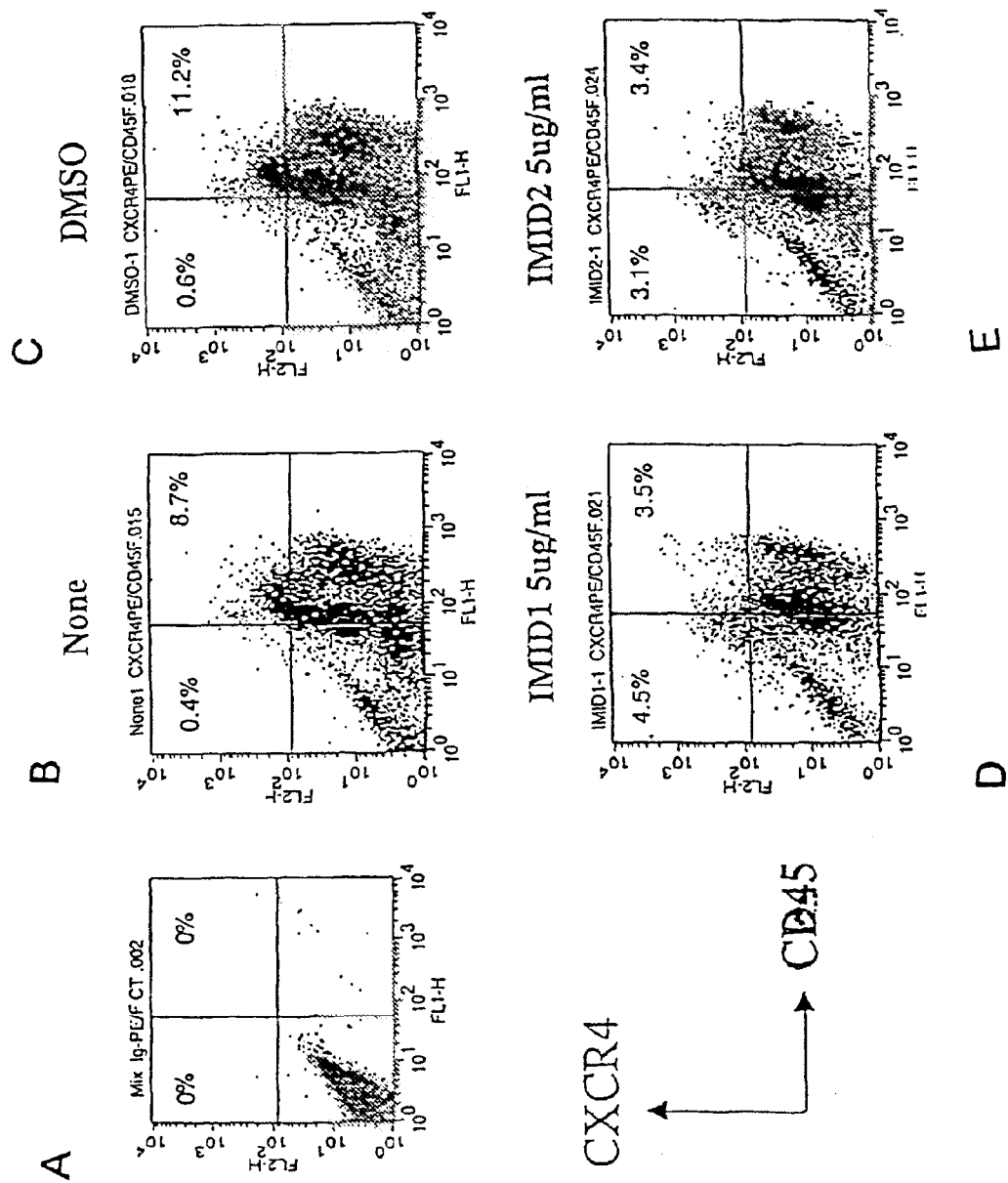

FIGS. 12(A-E). Flow cytograms. Exposure of MNCs to ACTIMID™ and REVIMID™ down-regulates the CXCR4+ CD45+ cell population, but increases the CXCR4+CD45− cell population. Percentages indicated on each cytogram indicate the percentage of the cell population expressing a particular combination of markers. A. Control, immunoglobulin (Ig). B. Control, no compound added. C. DMSO (5 µg/ml). D. ACTIMID™ (5 µg/ml). E. REVIMID™ (5 µg/ml). X-axis: relative intensity of CD45 (FL1-H) staining. Y-axis: relative intensity of CXCR4 (FL2-H) staining. See Section 6.3 for details.

Figure 13:
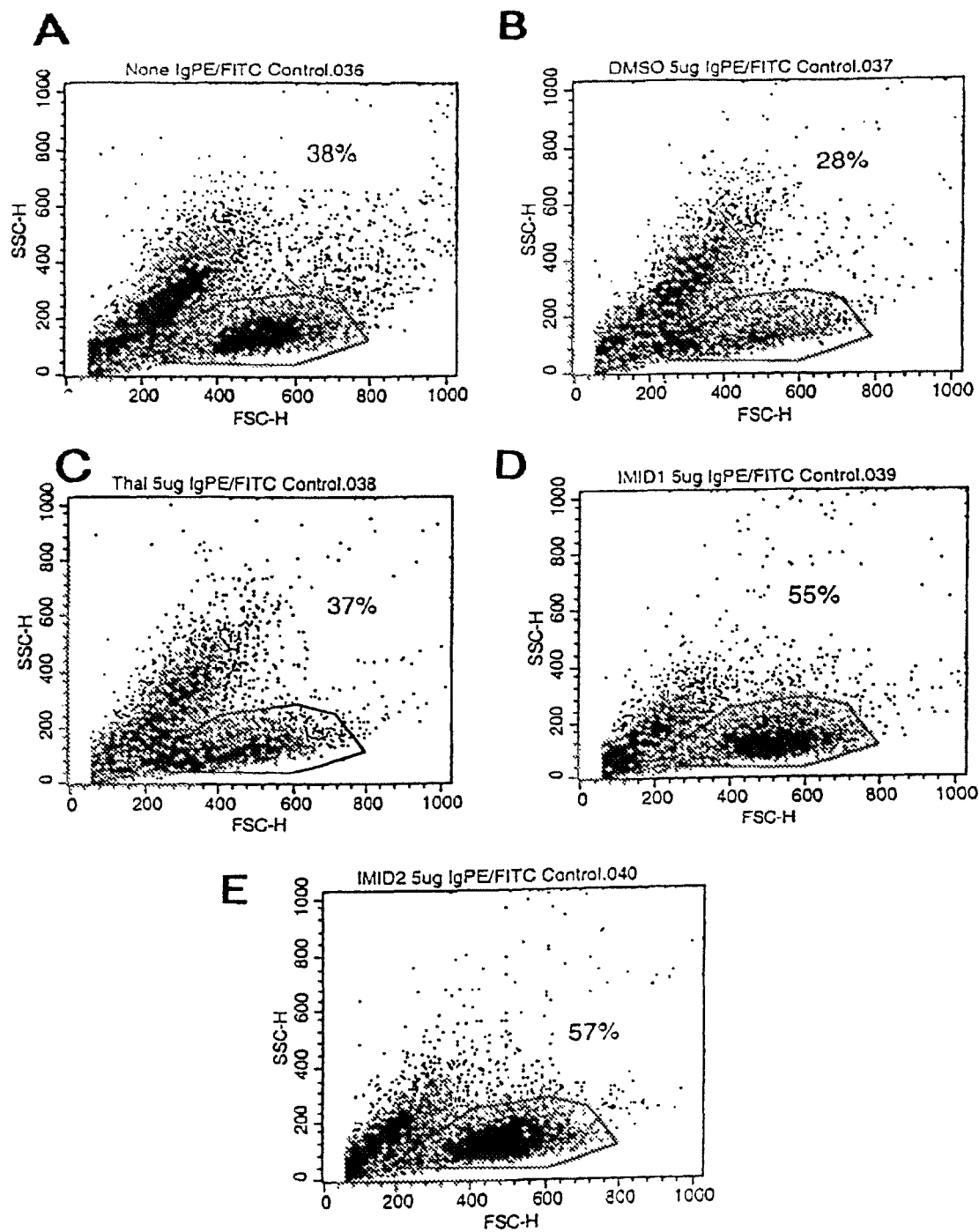

FIGS. 13(A-E). Flow cytograms. The effect of Thalomid, ACTIMID™ and REVIMID™ on lineage commitment of differentiating hematopoietic progenitors in the nucleated cell fraction of umbilical cord blood. The flow cytograms show that ACTIMID™ and REVIMID™ increase the percentage of monocyte lineage cells compared to control, indicating that there is a modulation of differentiation which shifts towards lineages which give rise to lymphoid and myeloid cells. A. Control, immunoglobulin (Ig). B. DMSO (5 µg/ml). C. Thal (5 µg/ml). D. ACTIMID™ (5 µg/ml). E. REVIMID™ (5 µg/ml). See Section 6.4 for details.

Figure 14:
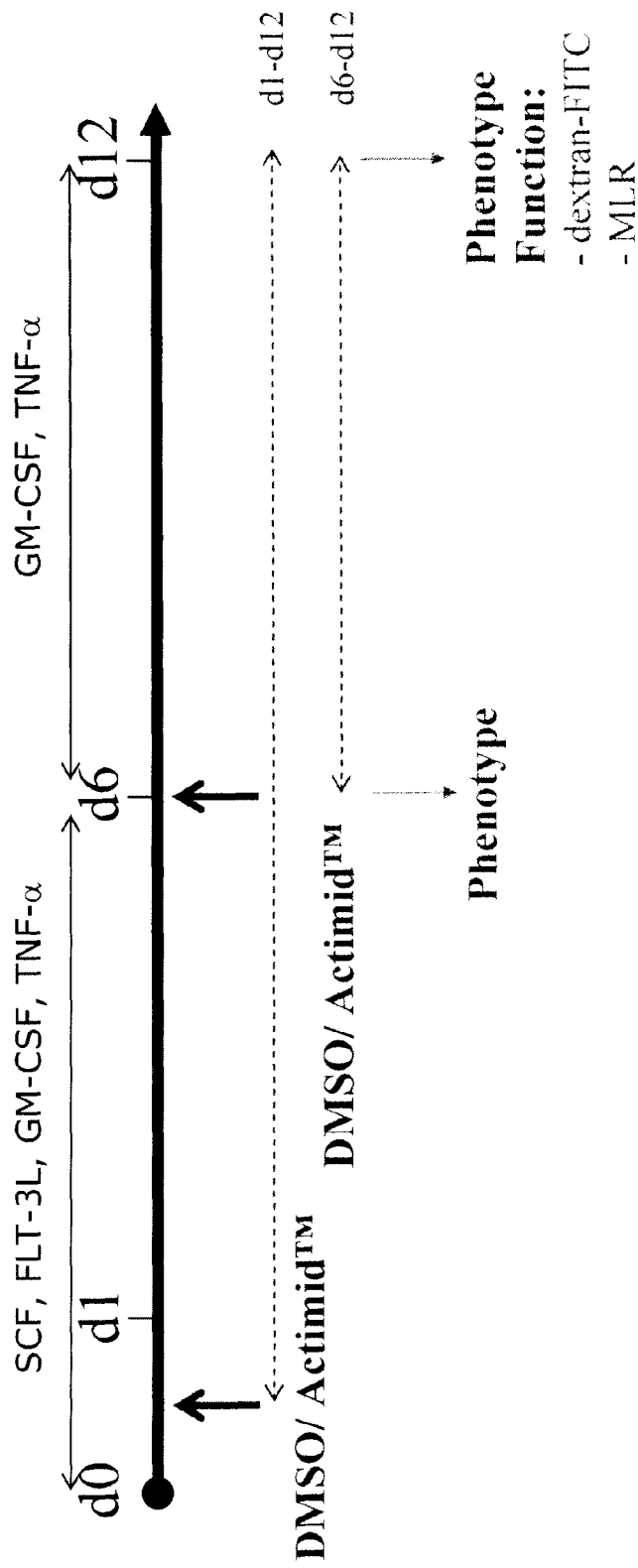

FIG. 14. Outline of study of effect of ACTIMID™ on CD34+ cell differentiation and maturation into DC cells. CD34+ cells were cultured in the presence or absence of 1.0 µM ACTIMID™ and DMSO (dimethylsulfoxide) during either the expansion and maturation phase (day 1 to day 12) or during the maturation phase (day 6 to day 12). Immunohistochemical markers were assessed at day 6 or day 12 using FITC and PE conjugated monoclonal antibodies. See Section 6.6 for details.

FIGS. 15(A-D). Flow cytograms showing phenotypic characteristics of day 6 CD34+ cells, exposed to ACTIMID™ from day 1. ACTIMID™ almost completely suppressed the development of CD86+CD1a$^+$ cells. Cells were double-labeled with CD1a FITC and CD14 PE or CD1a FITC and CD86 PE. A: CD86$^+$CD1$^+$ cells generated from CD34$^+$ cells treated with DMSO (control). B: CD14$^+$CD1$^+$ cells generated from CD34$^+$ cells treated with DMSO (control). C: CD86$^+$CD1$^+$ cells generated from CD34$^+$ cells treated with ACTIMID™. D: CD14$^+$CD1$^+$ cells generated from CD34$^+$ cells treated with ACTIMID™. Percentages in each cytogram indicate the percentage of cells expressing a particular combination of markers. See Section 6.6 for details.

FIGS. 16(A-D). Flow cytograms showing effect at day 6 of ACTIMID™ exposure during expansion phase (day 1 to day 6) on CD34+ cells. CD34$^+$ CD38− cells exposed to ACTIMID™ differentiated into CD34$^+$CD38−CD33$^+$ cells after 6 days. Cells were double-labeled with CD33 FITC and CD83 PE or C38 PE and CD34 PE. A: Cells treated with DMSO and labeled for CD34 and CD38. B: cells treated with DMSO and labeled for CD83 and CD33. C: cells treated with ACTIMID™ and labeled for CD34 and CD38. D: cells treated with Percentages in each cytogram indicate the percentage of cells expressing a particular combination of markers. See Section 6.6 for details.

Figure 17:
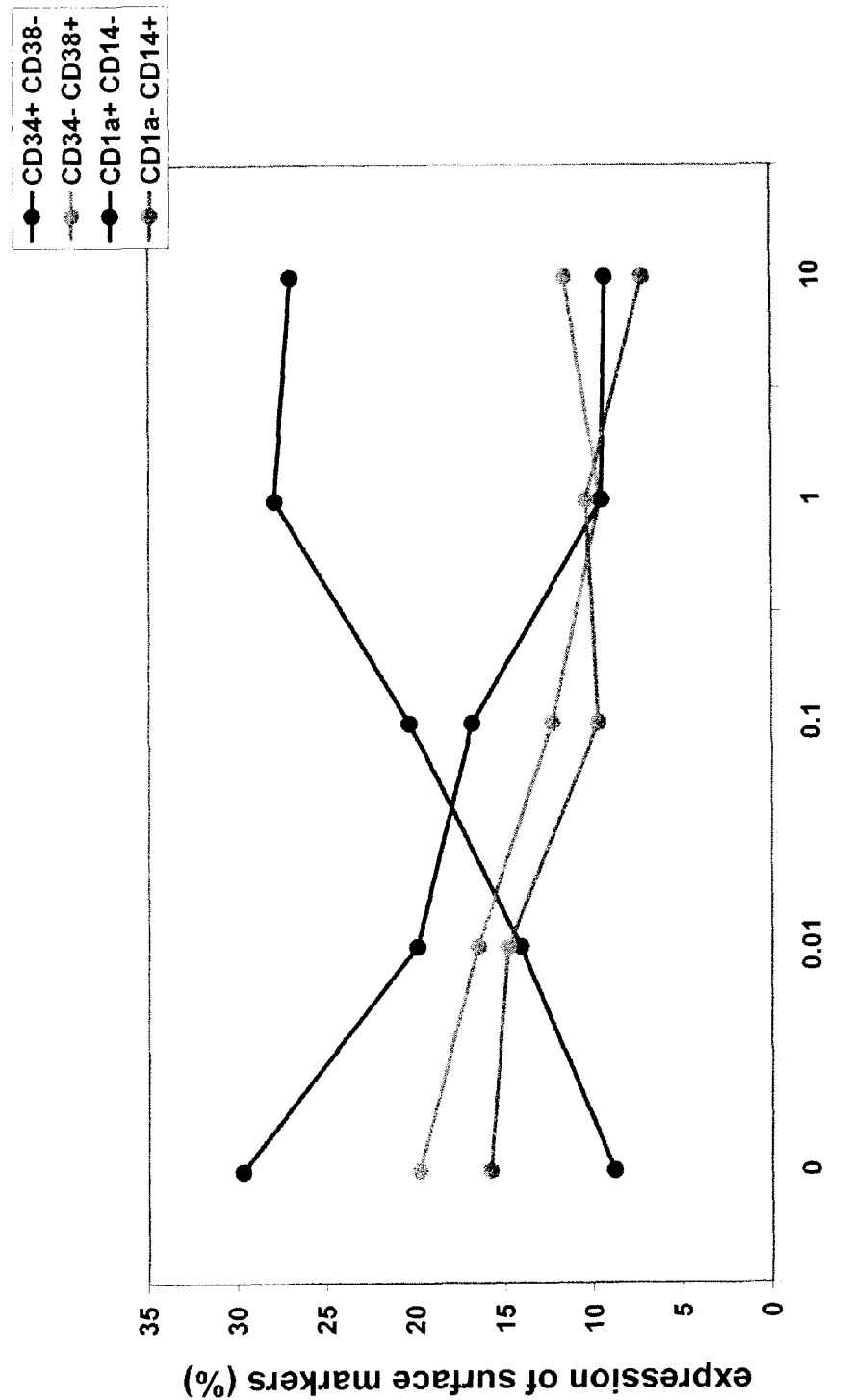

FIG. 17. ACTIMID™ induces a shift in CD34+ cell-derived cell populations from culture day 0 to day 6. Cells were cultured from day 0 to day 6 in the presence of different concentrations of ACTIMID™, then double labeled with CD34 and CD38 or CD1a and CD14. ACTIMID™ causes a marked increase in CD34+CD38– cells and an decrease in CD1a+CD14– cells. See Section 6.6 for details.

Figure 18:
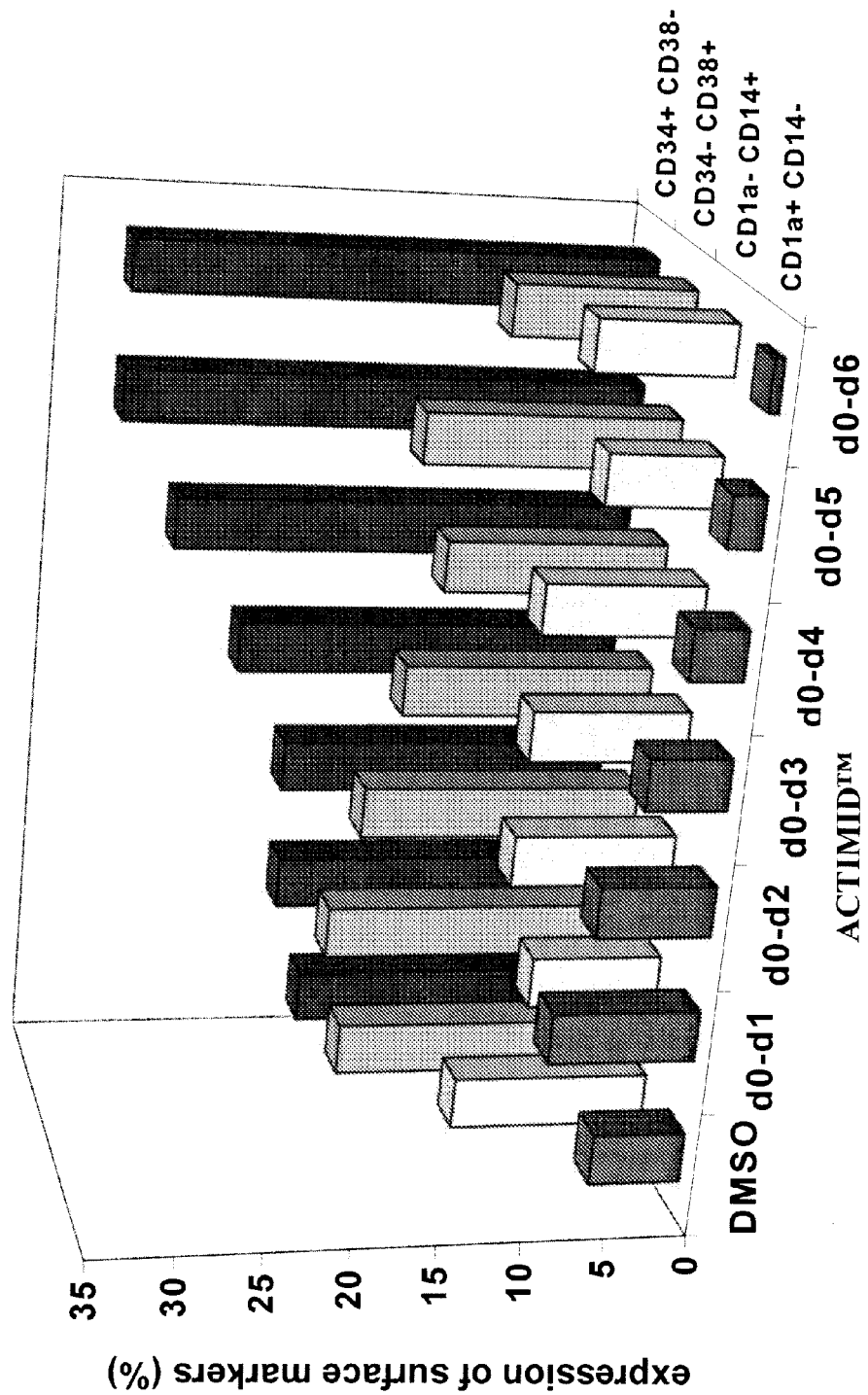

FIG. 18. Phenotypic modifications at day 6 of CD34+ cells treated for various times with ACTIMID™. Cells were plated and cultured for 6 days. Cells were treated with ACTIMID™ from day 0 to day 1 only, day 0 to day 2 only, day 0 to day 3 only, day 0 to day 4 only, day 0 to day 5 only, or day 0 to day 6. For incubations less than 6 days, ACTIMID™ was washed out on the indicated day and cells were resuspended in DMSO. At 6 days, the cells were labeled with CD34 and CD38 or CD1a and CD14. See Section 6.6 for details.

Figure 19A:
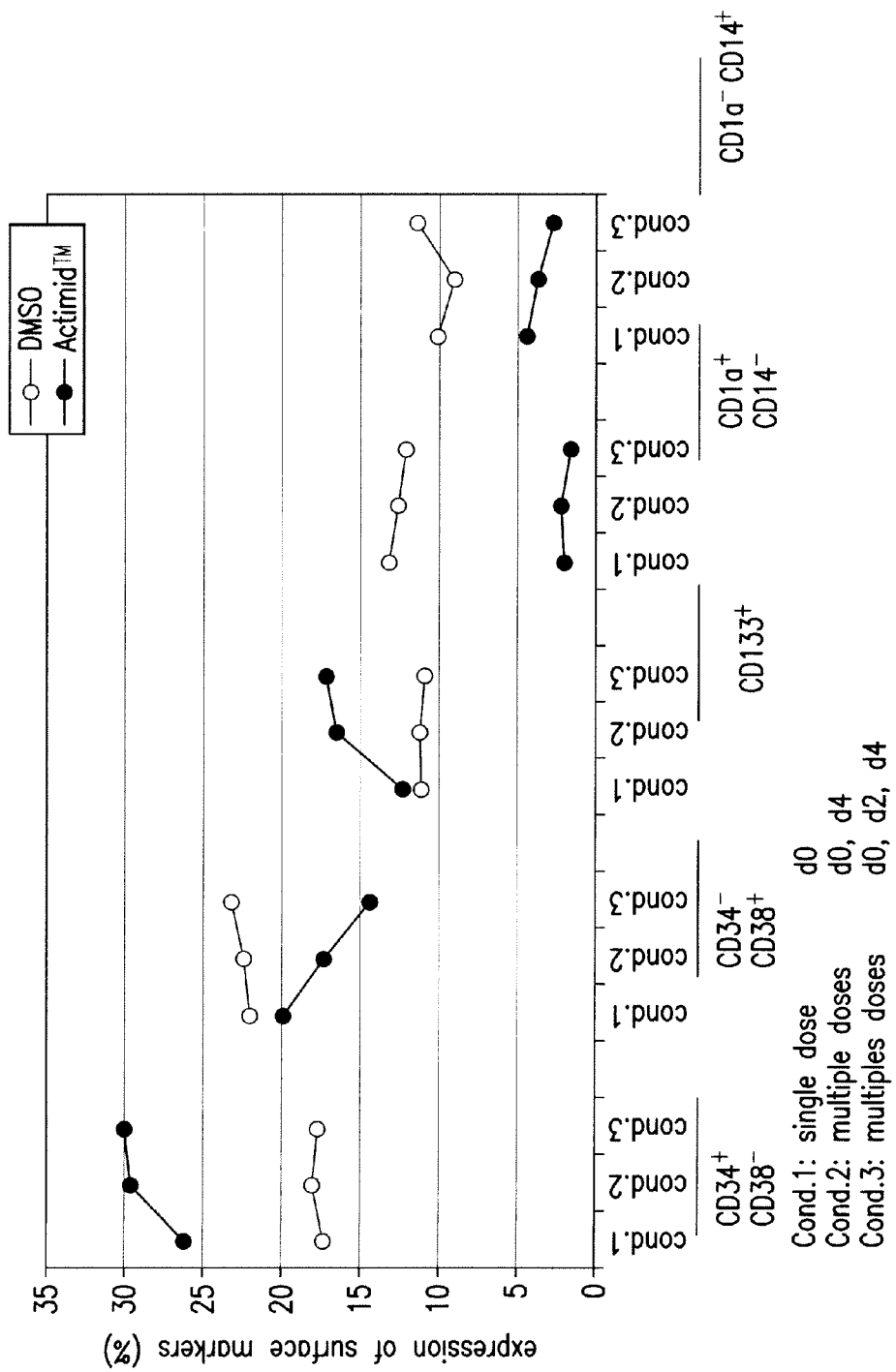
Figure 19B:
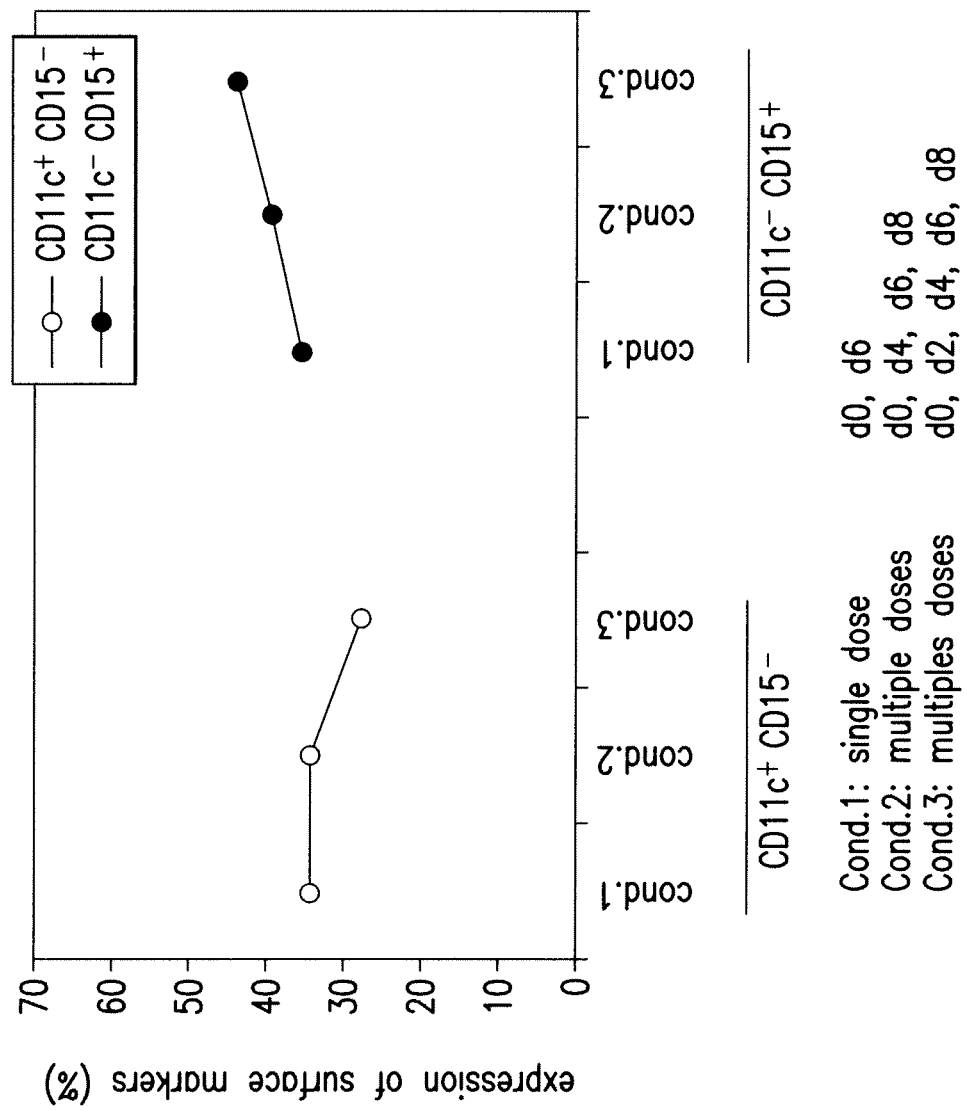

FIGS. 19(A-B). Phenotypic modifications at day 6 of CD34+ progenitor cells treated with single or multiple doses of ACTIMID™. FIG. 19A: Condition 1: single dose of ACTIMID™ at day 0; condition 2: ACTIMID™ administered at day 0 and day 4; condition 3: ACTIMID™ administered at day 0, day 2, and day 4. Y axis indicates the percentage of cells expressing the particular marker or combination of markers. FIG. 19B: Condition 1: single dose of ACTIMID™ at day 0; condition 2: ACTIMID™ administered at day 0, day 4, day 6 and day 8; condition 3: ACTIMID™ administered at day 0, day 2, day 4, day 6 and day 8. Cells were assessed for expression of CD11c and CD15, a granulocytic marker. Y axis indicates the percentage of CD11c+CD15– and CD11c–CD 15+ cells contacted with ACTIMID™ or DMSO (control). See Section 6.6 for details.

Figure 20E:
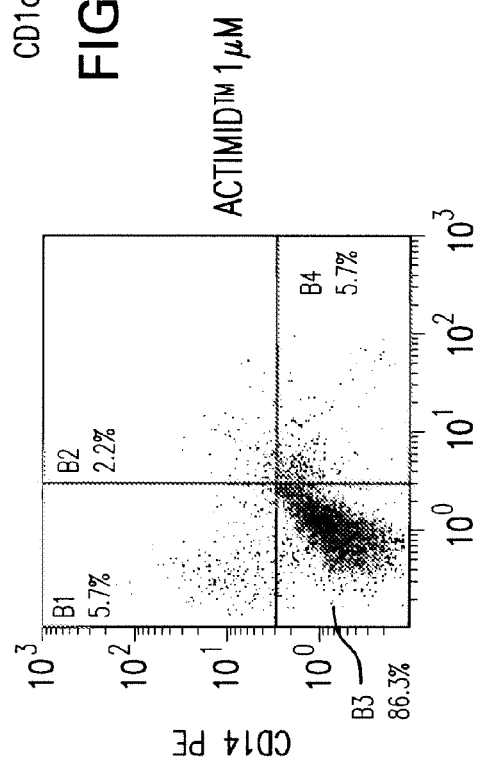
Figure 20F:
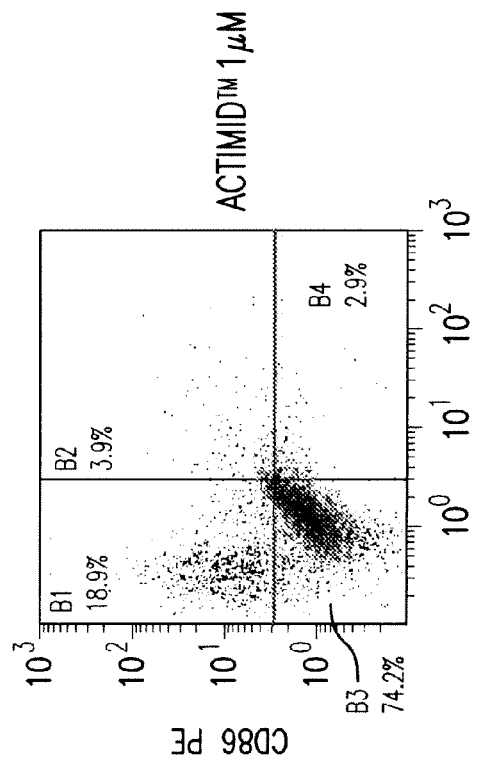

FIGS. 20(A-F). Flow cytograms of dendritic cells at day 12 generated from CD34+ cells exposed to ACTIMID™ (1 μM) from day 1 to day 12. ACTIMID™ causes the decrease of co-stimulatory molecules CD86 and CD80 at day 12 as compared to control. Cells were double-labeled with CD1a FITC and CD86 PE antibodies, CD1a FITC and CD80 PE antibodies, or CD1a FITC and CD14 PE antibodies. A: Cells treated with DMSO and stained at day 12 for CD86 and CD1a. B: Cells treated with DMSO and stained at day 12 for CD80 and CD1a. C: Cells treated with DMSO and stained at day 12 for CD14 and CD1a. D: Cells treated with ACTIMID™ and stained at day 12 for CD86 and CD1a. E: Cells treated with ACTIMID™ and stained at day 12 for CD80 and CD1a. F: Cells treated with ACTIMID™ and stained at day 12 for CD14 and CD1a. Percentages in each cytogram indicate the percentage of cells expressing a particular combination of markers. See Section 6.6 for details.

FIG. 21 (A-D). Flow cytograms of dendritic cells at day 12 generated from CD34+ cells exposed to ACTIMID™ (1 μM) from day 1 to day 12. Exposure to ACTIMID™ results in a modulation of adhesion molecule CD54 expression, causing a decrease in the expression of CD54$^{bright}$ and an increase expression of CD54$^{dim}$ relative to control (compare subpanels E and F in FIG. 21D). A: Cells treated with DMSO and stained for HLA-DR and with IgG1. B: Cells treated with DMSO and stained for CD54 and CD40. C: Cells treated with ACTIMID™ and stained for HLA-DR and with IgG1. D: Cells treated with ACTIMID™ and stained for CD54 and CD40. Percentages in each cytogram indicate the percentage of cells expressing a particular combination of markers. See Section 6.6 for details.

Figure 22:
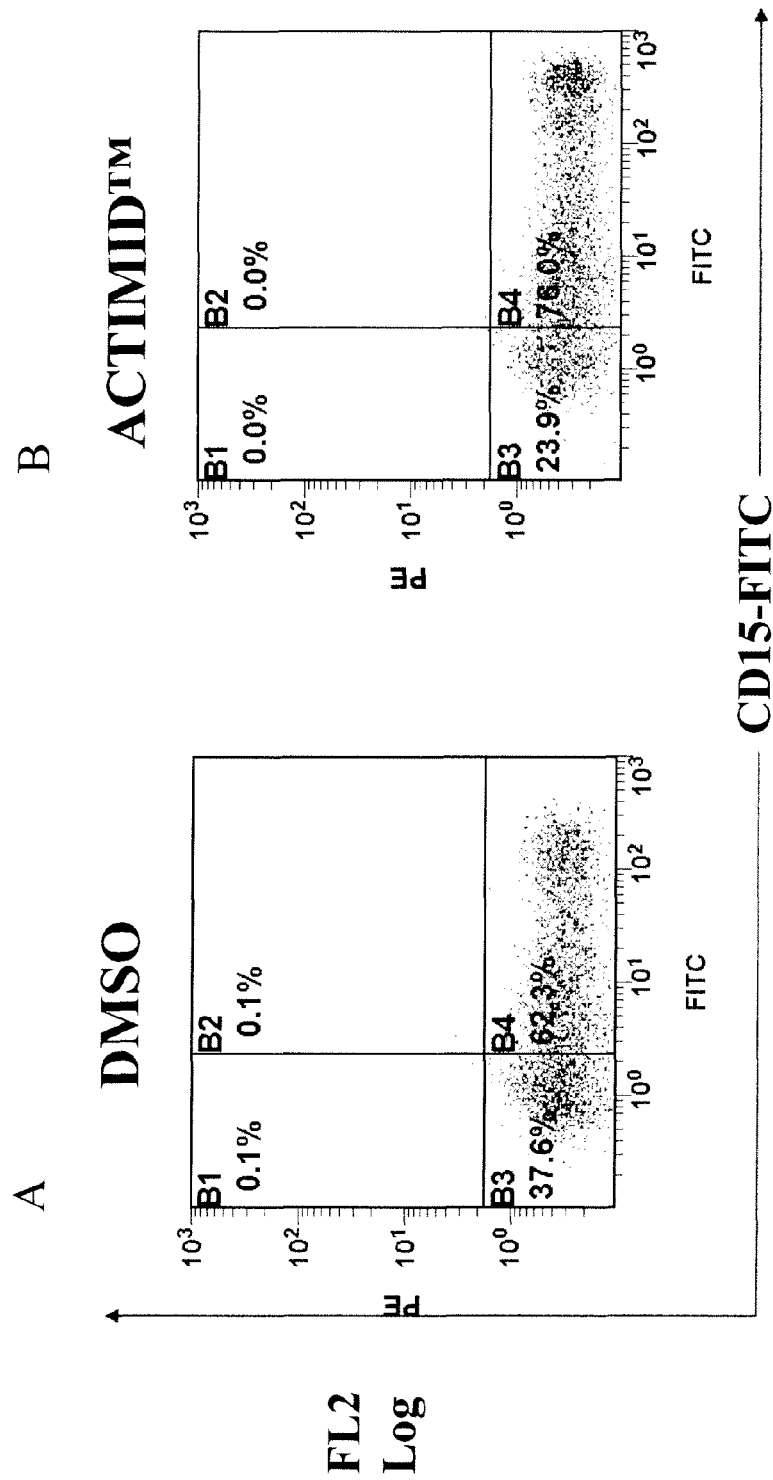

FIGS. 22(A-B). ACTIMID™ promotes granulocytic differentiation from CD34+ progenitor cells. Flow cytograms of CD34+ cells grown for 12 days in the presence of DMSO (FIG. 22A) or ACTIMID™ (FIG. 22B), then labeled with antibody to the granulocyte marker CD15. Percentages in each cytogram indicate the percentage of cells expressing a particular combination of markers. See Section 6.6 for details.

Figure 23:
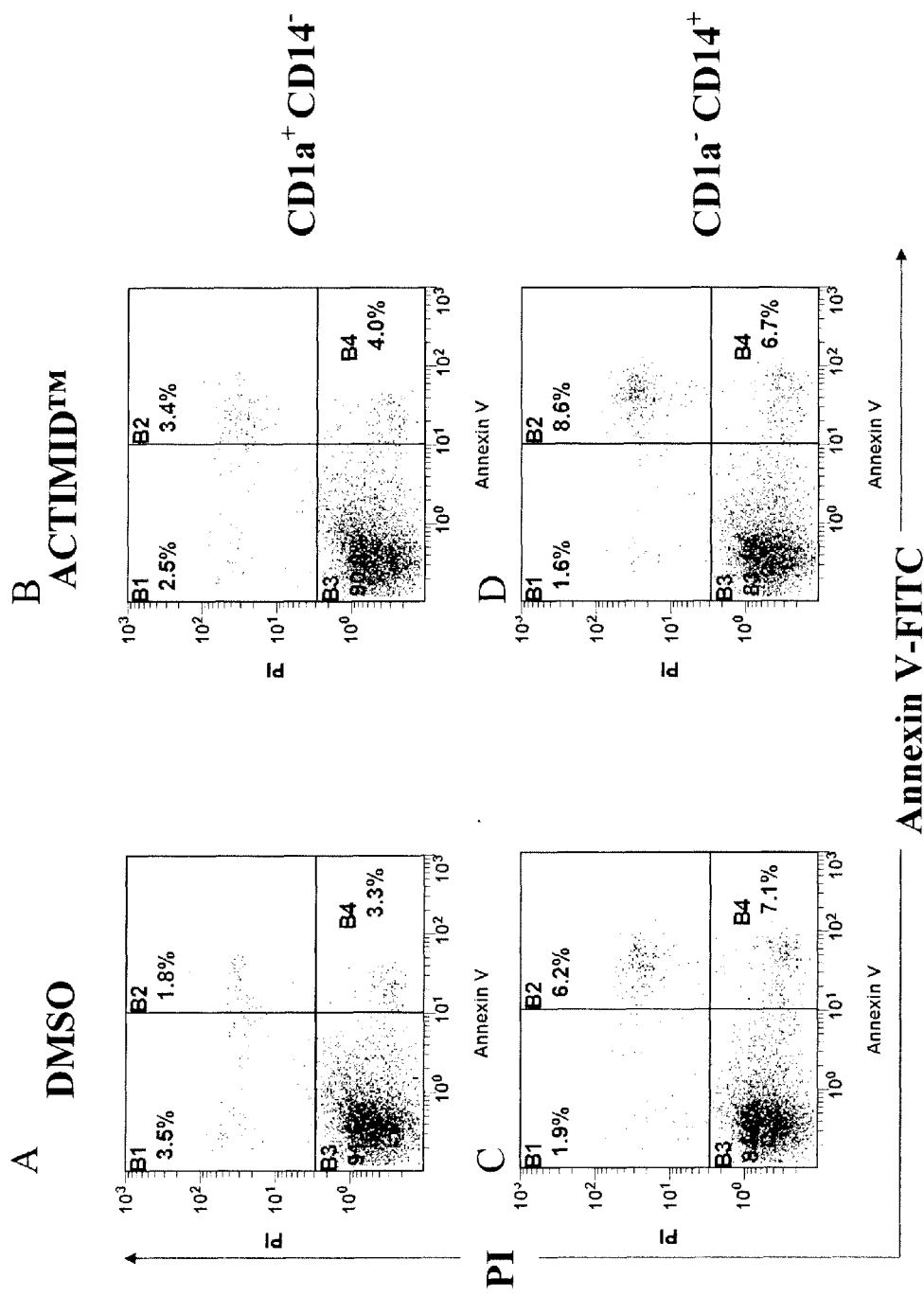

FIGS. 23(A-D). ACTIMID™ does not induce apoptosis of CD1a+ or CD14+ precursors. Flow cytograms of CD1a+CD14– and CD1a–CD14+ isolated cells (DC progenitors). CD34+ progenitors cells were cultured for a period of 6 days in the presence of SCF, Flt-3L, GM-CSF and TNF-α. At day 6, CD1a+CD14– and CD1a–CD14+ cells were isolated by magnetic cell sorting (Miltenyi), and purified CD1a+CD14– and CD1a–CD14+ populations were cultured for an additional 2 days in the presence of GM-CSF and TNF-α with or without ACTIMID™ (1 μM). Apoptotic cells were then monitored using Annexin V-FITC staining, a marker for apoptosis, in combination with propidium iodide (PI), a viability probe. Percentages in each cytogram indicate the percentage of cells staining positive for Annexin V-FITC and/or propidium iodide. The number of cells positive for Annexin V-FITC was comparable in ACTIMID™-treated and control cells (compare particularly B3 and B4 in each cytogram). A: CD1a+CD14– cells treated with DMSO. B: CD1a+CD14– cells treated with ACTIMID™. C: CD1a–CD14+ cells treated with DMSO. D: CD1a–CD14+ cells treated with ACTIMID™. See Section 6.6 for details.

Figure 24:
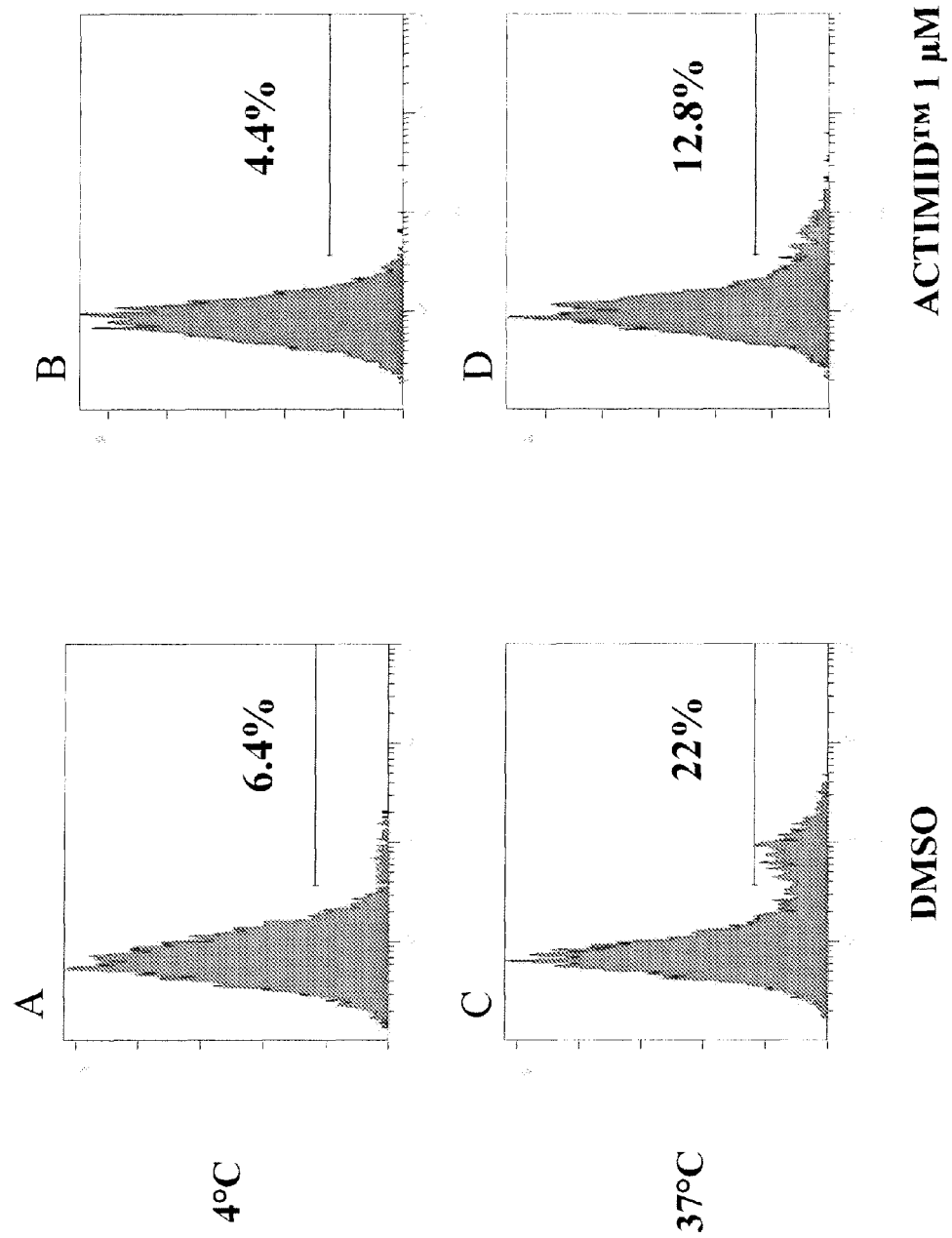

FIGS. 24(A-D). Flow cytograms of CD34+ cells grown for 12 days in the presence or absence of ACTIMID™. ACTIMID™ causes a decrease in mannose receptor-mediated endocytosis, as demonstrated by decreased uptake of FITC-labeled dextran relative to DMSO control. A: DMSO and 4° C. B. ACTIMID™ and 4° C. C: DMSO and 37° C. B. ACTIMID™ and 37° C. Percentage in each cytogram indicates the fraction of cells exhibiting endocytosis. See Section 6.6 for details.

Figure 25:
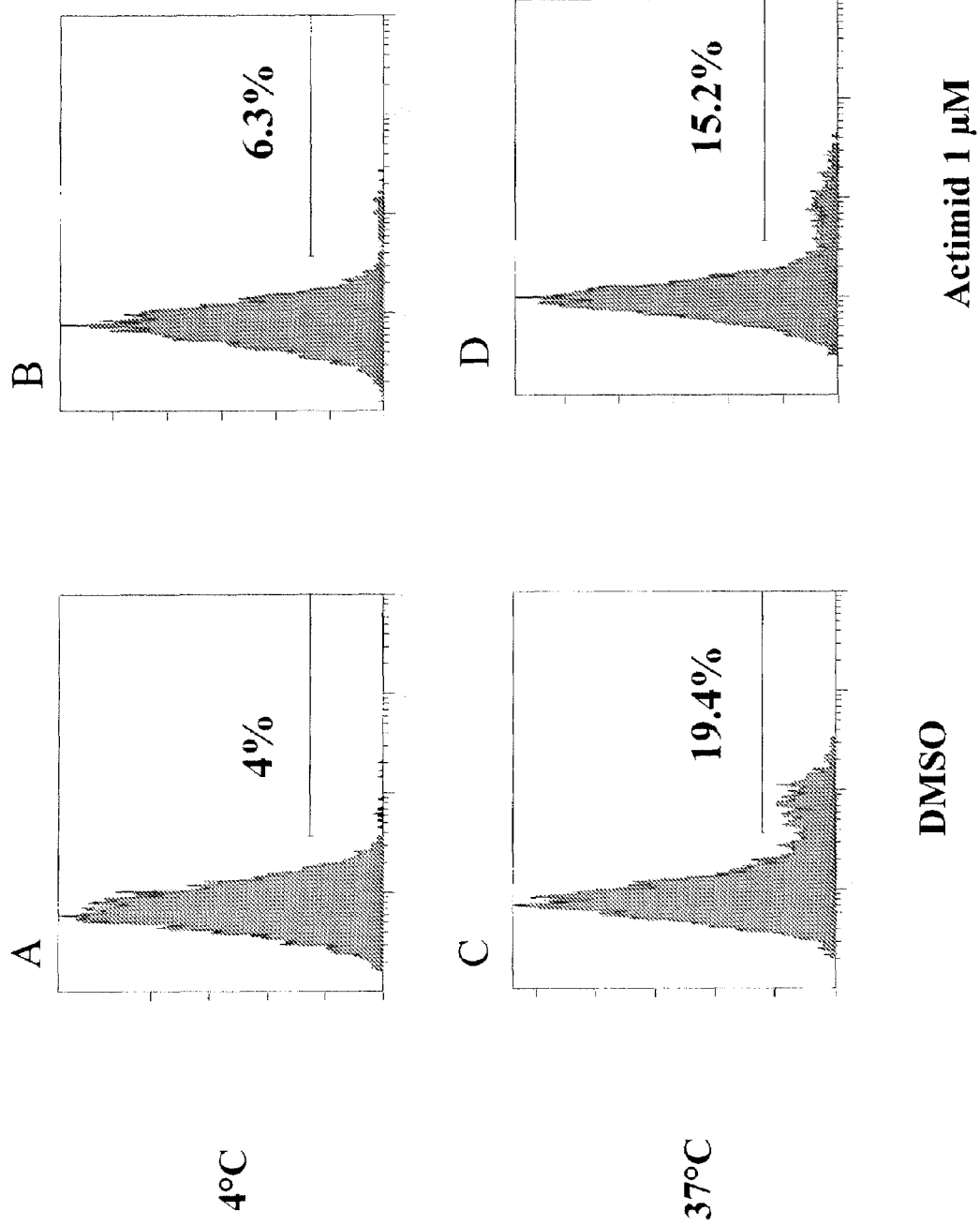

FIGS. 25(A-D). Flow cytograms of CD34+ cells cultured for 12 days, and cultured in the presence or absence of ACTIMID™ from days 6-12. Culturing in the presence of ACTIMID™ on days 6-12, after culture from days 1-5 in the absence of ACTIMID™, results in mannose receptor-mediated endocytosis comparable to that of DMSO control. Percentage in each cytogram indicates the fraction of cells exhibiting endocytosis. A: DMSO and 4° C. B. ACTIMID™ and 4° C. C: DMSO and 37° C. B. ACTIMID™ and 37° C. See Section 6.6 for details.

Figure 26:
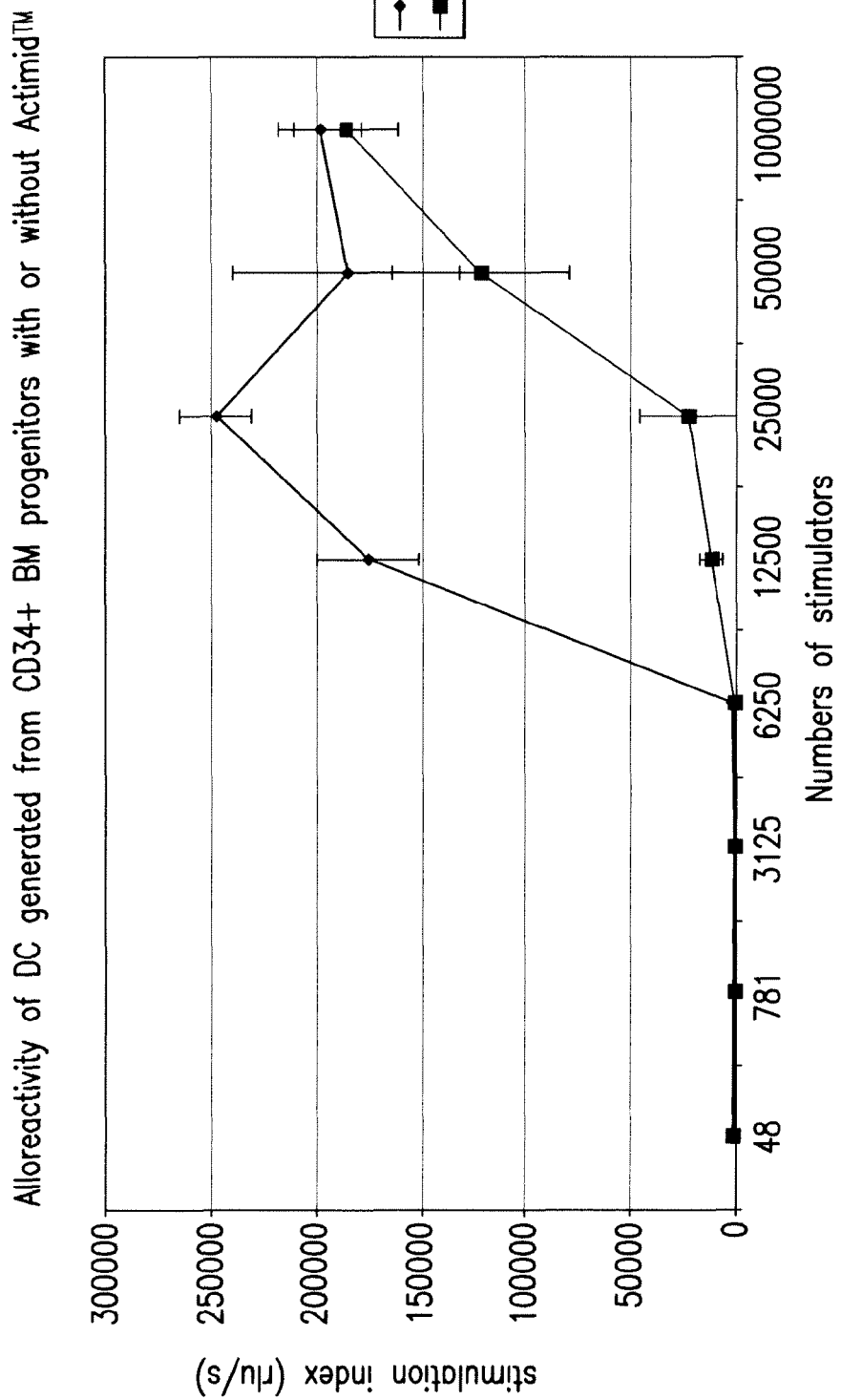

FIG. 26. ACTIMID™ reduces the capacity of CD34+ cells cultured for 12 days to present antigen. CD34+ cells were cultured for 12 days in the presence or absence of ACTIMID™; ACTIMID™-treated cells, at day 12, show a substantially decreased stimulation index as compared to DMSO control. See Section 6.6 for details.

Figure 27:
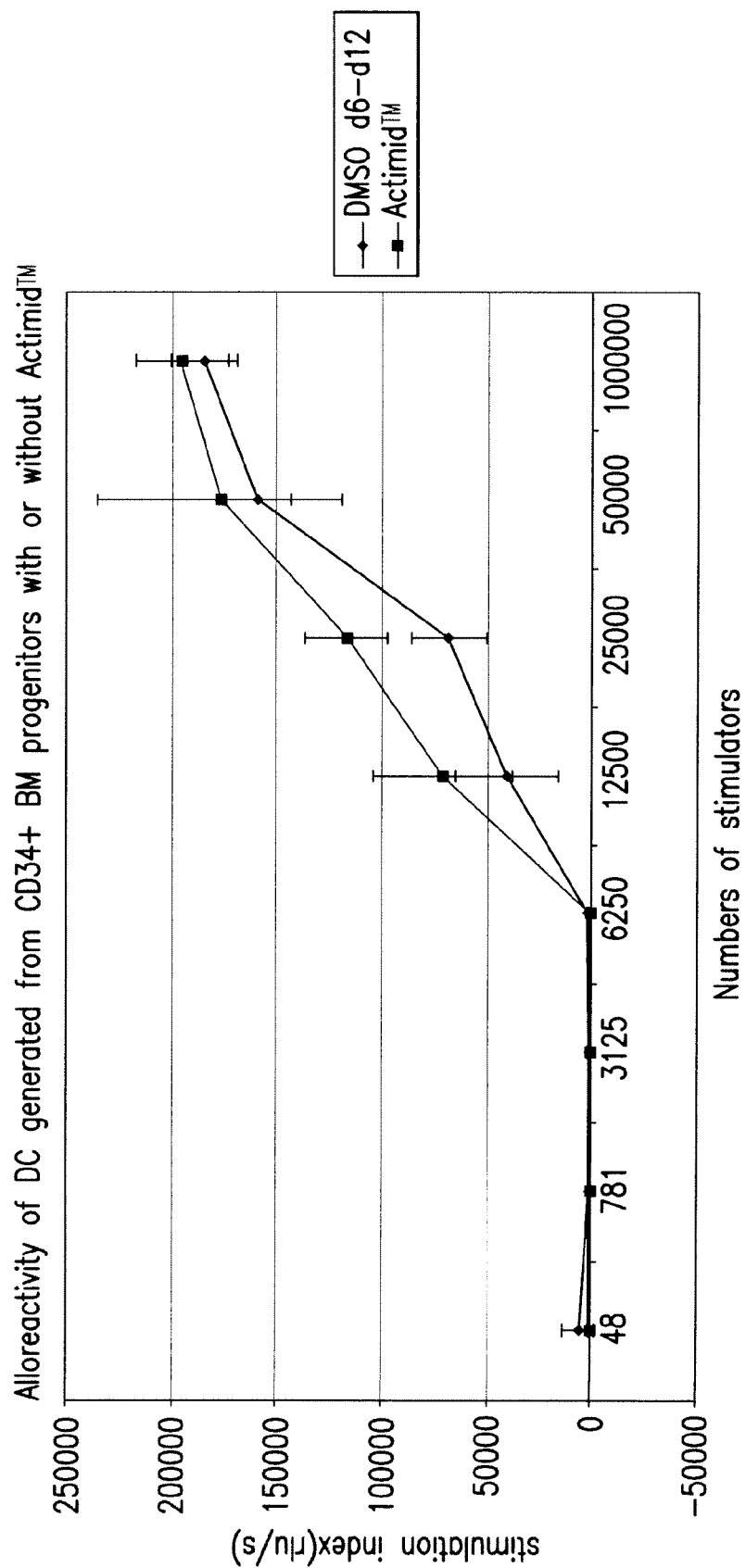

FIG. 27. ACTIMID™ has little APC reduction activity on CD34+ cells cultured in ACTIMID™ from day 6 to day 12. CD34+ cells were cultured for five days, the cultured in the presence or absence of ACTIMID™. Antigen-presenting capacity of treated cells is comparable to that of control, DMSO-treated cells. See Section 6.6 for details.

Figure 28:
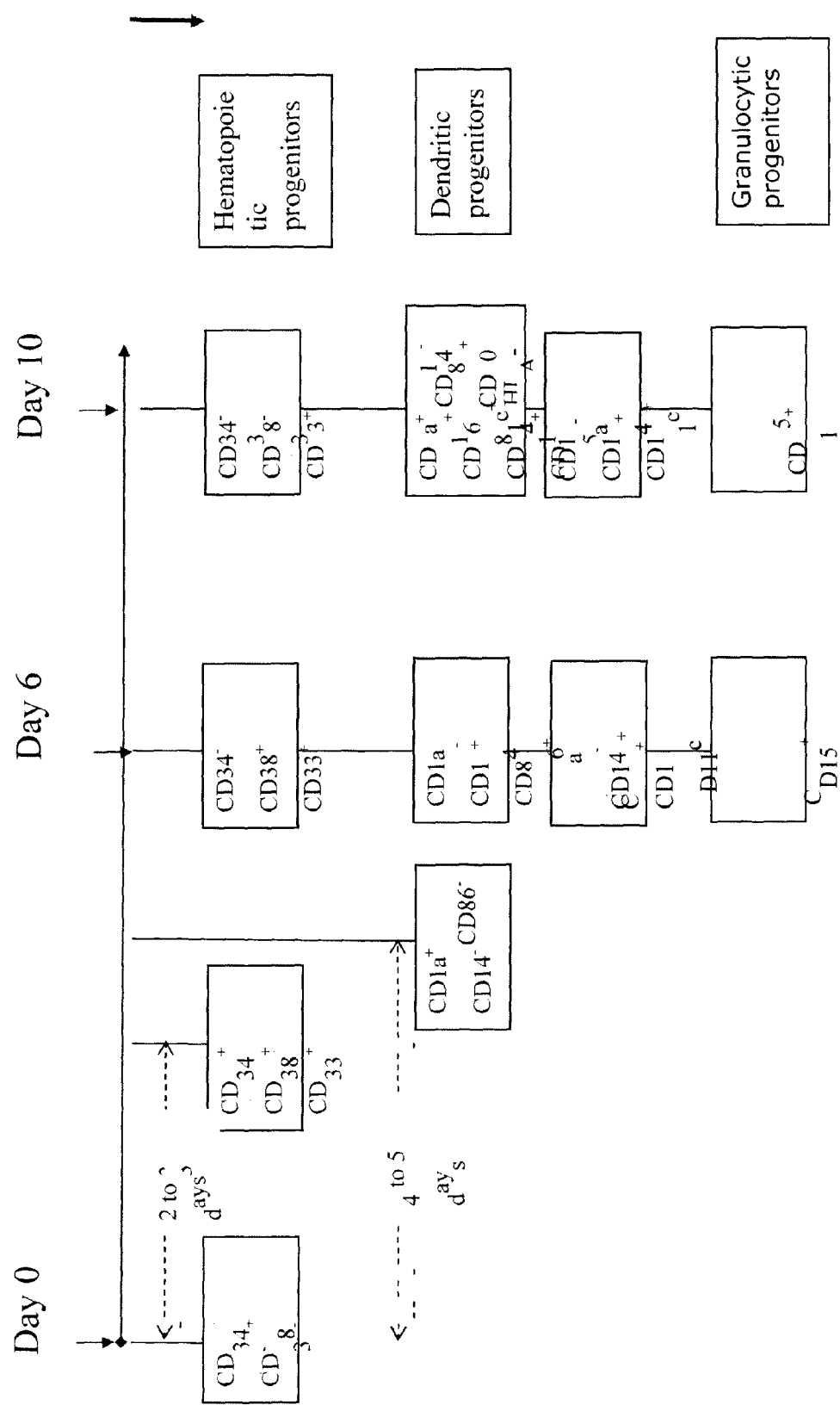

FIG. 28. Differentiation pathway of CD34+ hematopoietic progenitor cells cultured in the presence of GM-CSF and TNF-α.

Figure 29:
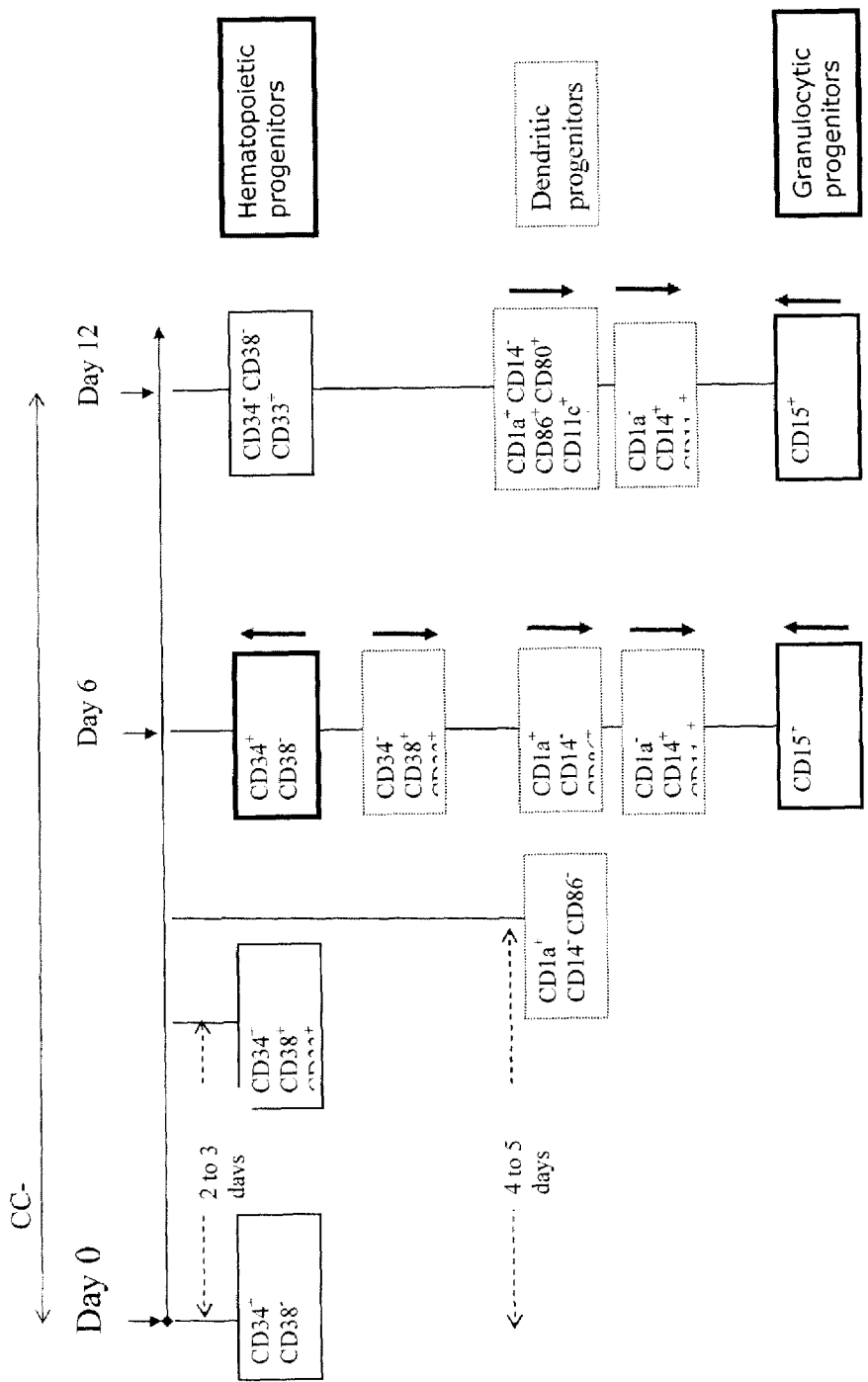

FIG. 29. Summary chart showing the effect of ACTIMID™ on the differentiation pathway of CD34+ hematopoietic progenitor cells cultured in the presence of GM-CSF and TNF-α. See Section 6.6 for details.

Figure 30:
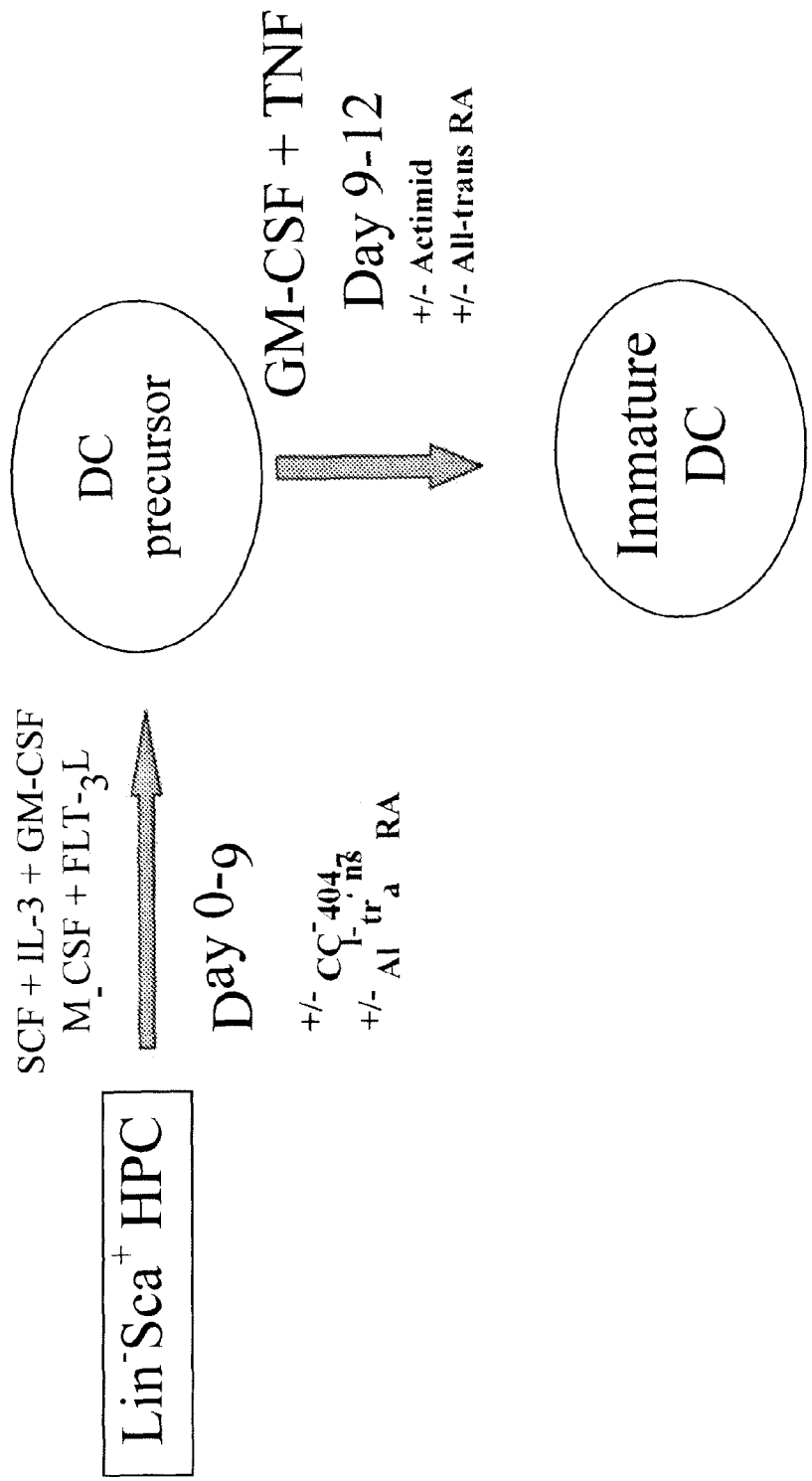

FIG. 30. Diagram showing maturation conditions for murine Sca+Lin– hematopoietic progenitor cells. Cells were grown for 9 days in the presence of stem cell factor (SCF), Flt-3L, granulocyte macrophage-colony stimulating factor (GM-CSF) and macrophage-colony stimulating factor (MCSF) in the presence of DMSO at 0.1% (control), 10 μM ACTIMID™ or 10 μM all-trans retinoic acid (ATRA) to drive cells to a DC precursor phenotype. Cells were then cultured from day 9 to day 12 in the presence of GM-CSF and TNF-α, plus DMSO, ACTIMID™ or ATRA, to drive differentiation of the murine cells to immature dendritic cells. See Section 6.8 for details.

Figure 31:
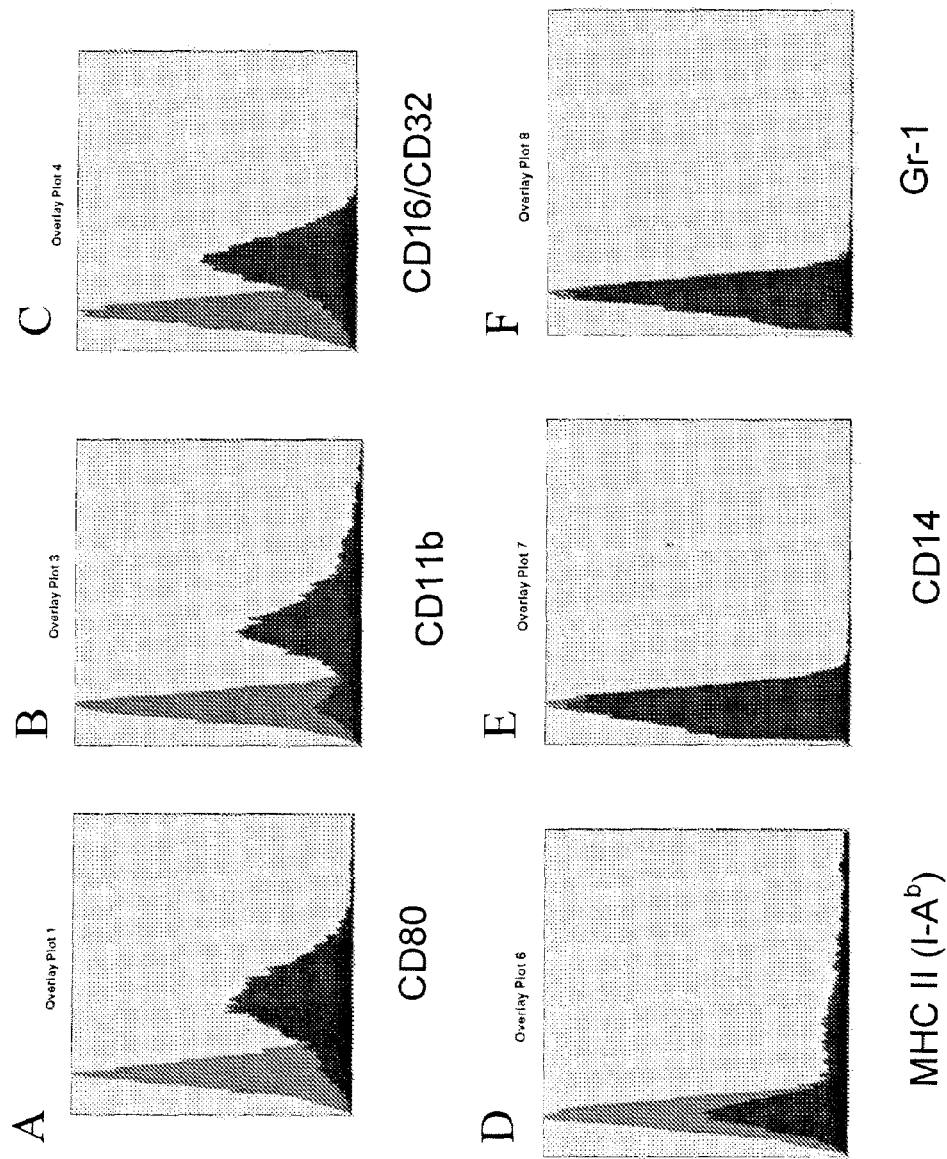

FIG. 31 (A-E). Murine cells present at day 9 under normal culture conditions (see Example 1, Materials & Methods; description of FIG. 30). Cells were labeled with antibodies to CD80 (FIG. 31A), CD11 (FIG. 31B), CD32/16 (FIG. 31C), MHC II ((I-A$^b$) (FIG. 31D), CD 14 (FIG. 31E) or Gr-1 (FIG. 31F). Cells at day 9 exhibited labeling with to the CD88, CD11 and CD32/16 markers, little labeling with antibodies to the 1 A$^b$ marker, and none to CD14 or Gr-1. See Section 6.8 for details.

Figure 32:
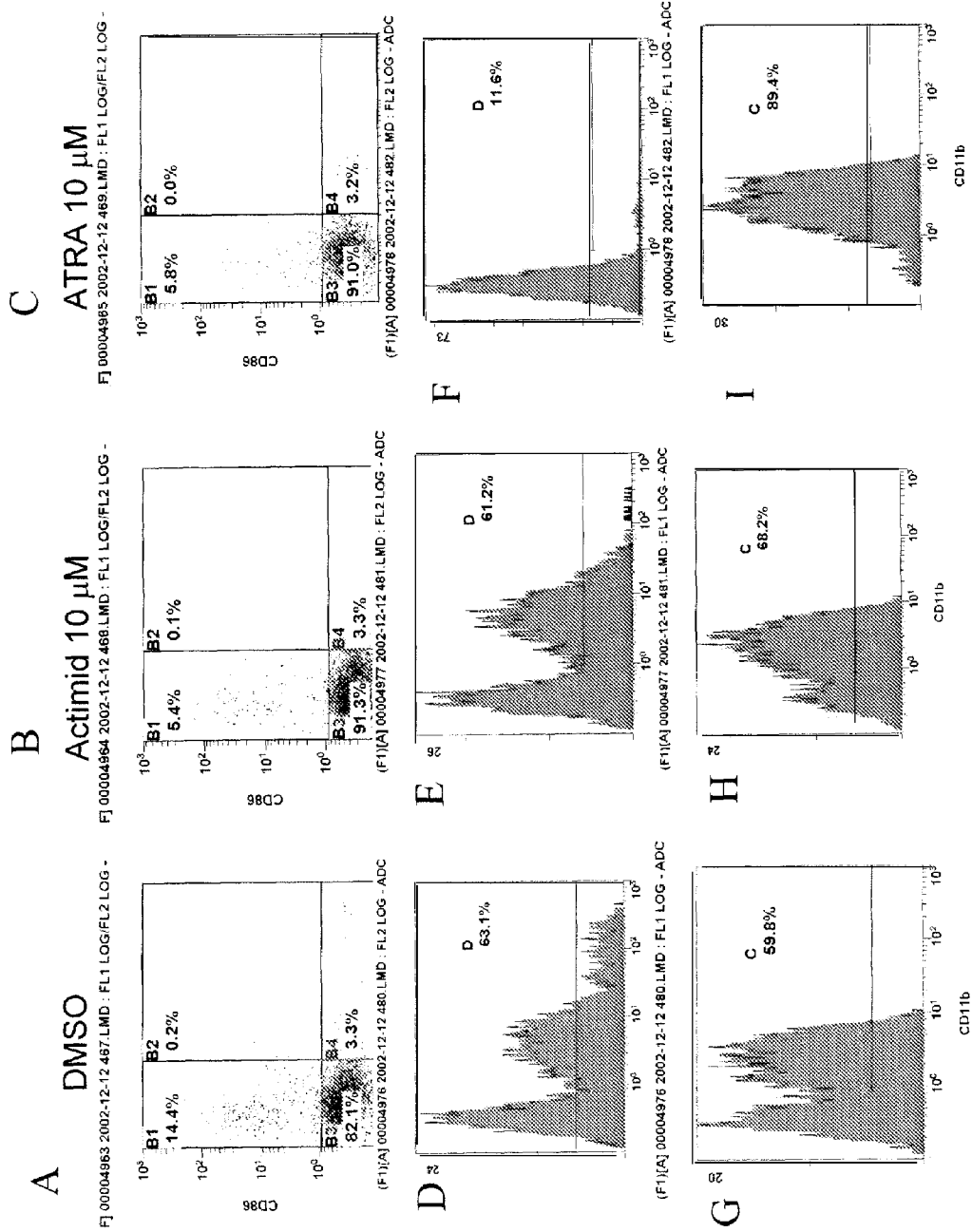

FIGS. 32(A-I). Flow cytograms of day 12 murine cells treated with DMSO, ACTIMID™ or ATRA. Cells were labeled with antibodies to CD86 and CD11b. FIGS. 32A-32C (top row): cytograms showing percentages of cells expressing CD86 (Y-axis) when treated with DMSO (control), ACTIMID™ or all-trans retinoic acid (ATRA). FIGS. 32D-32F (middle row): percentage of cells expressing the major histocompatibility II (MHC II) marker; treatment as in top row. FIGS. 32G-32I (bottom row): percentage of cells expressing CD11b; treatment as in top row. See Section 6.8 for details.

5. DETAILED DESCRIPTION OF THE INVENTION

The present invention is based, in part, on the unexpected discovery that the exposure of stem cells or progenitor cells to the compounds of the invention results in a regulatable means of controlling the differentiation of stem or progenitor cells into specific populations of progenitor cells or differentiation of progenitor cells into specific cell types, such as dendritic cells, granulocytes, endothelial cells or neural cells. In particular, the exposure of stem or progenitor cells to the compounds of the invention results in the regulatable differentiation and expansion of specific populations of hematopoietic cells, including CD34+, CD38+ and CD133+ cells. Such regulation of differentiation is accomplished without significant loss of yield due to cell death or differentiation to undesired cell types or cell lineages; in other words, the compounds of the invention do not cause apoptosis of one or more cell populations. Further, the exposure of hematopoietic progenitor cells to the compounds of the invention results in regulatable differentiation and expansion of specific cell types.

Thus, the present invention provides methods of modulating human stem cell differentiation, specifically CD34$^+$ hematopoietic progenitor cell, and CD133$^+$ progenitor cell differentiation. In particular, the present invention provides methods that employ small organic molecules that inhibit TNF-α activity to modulate the differentiation of progenitor cell populations along specific cell and tissue lineages. Further, the invention encompasses methods of expanding early progenitor cells, such as human CD133$^+$ or CD34$^+$, particularly CD34$^+$CD38$^-$ cells, for transplantation into mammals, birds or reptiles, comprising exposing hematopoietic progenitor cells to a TNF-α inhibitor or antagonist, wherein the inhibitor or antagonist is a small molecule. The invention also provides methods of producing other cell types from these early progenitor cells, including, but not limited to, cells of the brain, kidney, intestinal tract and muscle. The compounds of the invention also act to suppress dendritic cell differentiation, and promote granulocytic cell differentiation, from early progenitor cells, such as human CD34$^+$ progenitor cells.

Examples of the small molecule compounds that may be used in connection with the invention, include, but are not limited to, compounds that inhibit TNF-α activity. Compounds that may be used in the methods of the invention are described in detail in Section 5.3. In one embodiment, the preferred compounds are thalidomide analogs, although thalidomide hydrolysis products, metabolites, derivatives and precursors of thalidomide may also be used. In particularly preferred embodiments, the compounds are IMIDS® ((Celgene) such as ACTIMID™ and REVIMID™.

The methods of the invention encompass the regulation of differentiation of a stem or progenitor cell into a specific cell lineage, including, but not limited to, a mesenchymal, hematopoietic, adipogenic, hepatogenic, neurogenic, gliogenic, chondrogenic, vasogenic, myogenic, chondrogenic, or osteogenic lineage comprising incubating the stem or progenitor cell with a compound of the invention, preferably in vitro, for a sufficient period of time to result in the differentiation of the cell into a cell of a desired cell lineage. In a specific embodiment, differentiation of a stem or progenitor cell into a cell of the hematopoietic lineage is modulated. In particular, the methods of the invention may used to modulate the generation of blood cell colony generation from CD34$^+$, CD133$^+$, and CD45$^+$ hematopoietic progenitor cells in a dose-responsive manner.

The methods of the invention also encompass the regulation of differentiation of a CD34$^+$ progenitor cell into dendritic cells comprising incubating the progenitor cell with a compound of the invention, preferably in vitro, for a sufficient period of time to result in the differentiation of the cell into a cell of a desired cell lineage. In a specific embodiment, differentiation of a such a progenitor cell into a cell of the dendritic cell lineage is modulated through contacting said cell with ACTIMID™ or REVIMID™, or an analog or prodrug of either. In another specific embodiment, the differentiation of a CD34$^+$ progenitor cell is modulated to suppress differentiation along a myeloid lineage and encourage differentiation along a granulocytic lineage. In a more specific embodiment, differentiation of a CD34+ progenitor cell into a cell of a granulocytic cell lineage is modulated by a method comprising contacting a CD34$^+$ progenitor cell with a compound of the invention on the first day said progenitor cells are cultured.

Any mammalian stem or progenitor cell can be used in accordance with the methods of the invention, including but not limited to, stem cells isolated from cord blood ("CB" cells), placenta and other sources. The stem cells may include pluripotent cells, i.e., cells that have complete differentiation versatility, that are self-renewing, and can remain dormant or quiescent within tissue. The stem cells may also include multipotent cells or committed progenitor cells. In one preferred embodiment, the invention utilizes stem cells that are viable, quiescent, pluripotent stem cells that exist within the full-term placenta can be recovered following successful birth and placental expulsion, exsanguination and perfusion resulting in the recovery of multipotent and pluripotent stem cells.

In another preferred embodiment, the progenitor cells are early progenitor cells, particularly CD34$^+$ or CD133$^+$ cells. Preferably, CD34$^+$ or CD133$^+$ progenitor cells are derived from human bone marrow, placenta, or cord blood. Equivalents of these cells from other mammals may also be used. In mouse, for example, Sca$^+$ progenitor cells may be used in the methods of the invention. Equivalent early progenitor cells from birds or reptiles may also be used.

In a particular embodiment of the invention, cells endogenous to the placenta, or produced by a postpartum perfused placenta, including, but not limited to, embryonic-like stem cells, progenitor cells, pluripotent cells and multipotent cells, are exposed to the compounds of the invention and induced to differentiate while being cultured in an isolated and perfused placenta. The endogenous cells propagated in the postpartum perfused placental may be collected, and/or bioactive molecules recovered from the perfusate, culture medium or from the placenta cells themselves.

In another embodiment of the invention, stem or progenitor cells that are derived from sources other than postpartum placenta are exposed to the compounds of the invention and induced to differentiate while being cultured in vitro. Thus, the invention encompasses methods for differentiating mammalian stem cells into specific progenitor cells comprising differentiating the stem cells under conditions and/or media suitable for the desired differentiation and in the presence of a compound of the invention.

Further, the invention encompasses methods for modulating or regulating the differentiation of a population of a specific progenitor cell into specific cell types comprising differentiating said progenitor cell under conditions suitable for said differentiation and in the presence of one or more compounds of the invention. Alternatively, the stem or progenitor cell can be exposed to a compound of the invention and subsequently differentiated using suitable conditions. Examples of suitable conditions include nutrient media formulations supplemented with human serum and cell culture matrices, such as MATRIGEL® supplemented with growth factors.

The method of the invention also contemplates that different cell populations may be produced by contacting the progenitor cell(s) with a compound of the invention at various times during culture, either at the proliferation or differentiation stage. See Section 5.4, particularly Section 5.4.2, below.

In a specific embodiment, the present invention provides methods that employ amides and imide small molecules, particularly amino conjugates of thalidomide, to modulate and regulate hematopoiesis in the context of pre-transplantation conditioning of hematopoietic progenitors.

The present invention also provides methods that employ the small molecules of the invention to modulate and regulate hematopoiesis in the context of ex vivo conditioning of hematopoietic progenitors. The methods of the invention encompass the regulation of stem or progenitor cell differentiation in vitro, comprising incubating the stem or progenitor cells with the compound in vitro, followed by direct transplantation of the differentiated cells to a subject.

The invention also encompasses the control or regulation of stem or progenitor cells in vivo by the administration of both a stem or progenitor cell and a compound of the invention to a patient in need thereof.

The invention further encompasses the transplantation of pretreated stem or progenitor cells to treat or prevent disease. In one embodiment, a patient in need of transplantation is also administered a compound of the invention before, during and/or after transplantation. In another embodiment, a patient in need of transplantation is also administered untreated stem or progenitor cells, e.g., cord blood cells, adult blood cells, peripheral blood cells, or bone marrow cells. In another embodiment, the methods of the invention include the administration of the compounds to a subject that is the recipient of unconditioned stem cells or progenitor cells for the purpose of eliciting a modulatory effect on the stem cells that have already been transplanted.

In certain embodiments, the invention encompasses bone marrow transplantation which comprises transplanting cord blood (or stem cells obtained from cord blood), peripheral (i.e., adult) blood (or stem cells obtained from peripheral blood), wherein said cord blood or stem cells have been pretreated with a compound of the invention. Further, the invention encompasses the use of white blood cells made from hematopoietic progenitor cells that have been differentiated in the presence of a compound of the invention. For example, white blood cells produced by differentiating hematopoietic progenitor can be used in transplantation or can be mixed with cord blood or cord blood stem cells prior to transplantation.

In other embodiments, the invention encompasses bone marrow transplantation which comprises transplanting early progenitor cells, such as $CD34^+$ or $CD133^+$ progenitor cells, obtained according to the methods of the invention, wherein said progenitor cells have been pretreated with a compound of the invention. In one embodiment of the invention, said dendritic cell precursors are $CD34^+CD38^-CD33^+$ or $CD34^+CD38^-CD33+$ precursor cells. Further, the invention encompasses the use of cells made from $CD34^+$ progenitor cells that have been differentiated in the presence of a compound of the invention. For example, $CD34^+CD38^-CD33^+$ precursor cells, $CD34^+CD38^-CD33^-$ precursor cells, granulocytes, etc. produced by the differentiation of $CD34^+$ progenitor cells using the compounds of the invention can be used in transplantation. Cells differentiated from $CD133^+$ cells, using the compounds of the invention, are also encompassed by the present invention.

The invention further encompasses methods of conditioning stem cells following cryopreservation and thawing, to counteract the deleterious effects of cryopreservation and exposure to cryopreservatives on the stem cells. In certain embodiments, the invention provides methods of conditioning stem cells following cryopreservation and thawing, to counteract the deleterious effects of exposure to cryopreservatives (e.g., DMSO) on the proliferative and migratory capacity of stem cells.

5.1. Modulation of Differentiation of Stem Cells and CD34+ or CD133+ Progenitor Cells 5.1.1. Stem Cells The present invention provides methods of modulating human stem cell differentiation. In certain embodiments, the methods of the invention encompass the regulation of stem or progenitor cell differentiation in vitro, comprising incubating the stem cells with the compound in vitro, followed by direct transplantation of the differentiated cells to a subject. In other embodiments, the methods of the invention encompass the regulation of stem or progenitor cell differentiation in vivo, comprising delivering the compounds to a subject that is the recipient of unconditioned stem cells, followed by direct administration of the compound to the subject.

The embryonic-like stem cells obtained by the methods of the invention may be induced to differentiate along specific cell lineages, including, but not limited to a mesenchymal, hematopoietic, adipogenic, hepatogenic, neurogenic, gliogenic, chondrogenic, vasogenic, myogenic, chondrogenic, or osteogenic lineage.

In certain embodiments, embryonic-like stem cells obtained according to the methods of the invention are induced to differentiate for use in transplantation and ex vivo treatment protocols. In certain embodiments, embryonic-like stem cells obtained by the methods of the invention are induced to differentiate into a particular cell type and genetically engineered to provide a therapeutic gene product. In a specific embodiment, embryonic-like stem cells obtained by the methods of the invention are incubated with a compound, such as a small organic molecule, in vitro, that induces it to differentiate, followed by direct transplantation of the differentiated cells to a subject. In a preferred embodiment, the compounds that are used to control or regulate differentiation of stem cells are not polypeptides, peptides, proteins, hormones, cytokines, oligonucleotides or nucleic acids.

Stem cells that may be used in accordance with the invention include, but are not limited to, cord blood (CB) cells, placental cells, embryonic stem (ES) cells, embryonic-like stem cells, trophoblast stem cells, progenitor cells, bone marrow stem cells and multipotent, pluripotent and totipotent cells.

In particular, the methods of the invention encompass the regulation of the differentiation of stem cell populations, in addition to mesenchymal stem cells, into specific tissue lineages. For example, the methods of the invention may be employed to regulate the differentiation of a multipotent stem cell into chondrogenic, vasogenic, myogenic, and osteogenic lineage cells by promoting specific musculoskeletal regeneration and repair, neoangiogenesis, and repopulation of specific muscular tissues, such as myocardium and skeletal muscle, and revascularization of a variety of organs and tissues including, but not limited to brain, spinal cord, liver, lung, kidney and pancreas. The methods of the invention may be employed to regulate differentiation of a multipotent stem cell into cell of adipogenic, chondrogenic, osteogenic, neurogenic or hepatogenic lineage.

The agent used to modulate differentiation can be introduced into the postpartum perfused placenta to induce differentiation of the cells being cultured in the placenta. Alternatively, the agent can be used to modulate differentiation in vitro after the cells have been collected or removed from the placenta.

The methods of the invention encompass the regulation of progenitor stem cell differentiation to a cell of the hematopoietic lineage, comprising incubating the progenitor stem cells with the compound in vitro for a sufficient period of time to result in the differentiation of these cells to a hematopoietic lineage. In particular, the methods of the invention may used to modulate the generation of blood cell colony generation from CD34+, CD133+, and CD45+ hematopoietic progenitor cells in a dose-responsive manner (for discussion of dosing, see Section 5.7).

Preferably, the methods of the invention may be used to suppress specifically the generation of red blood cells or erythropoietic colonies (BFU-E and CFU-E), while augmenting both the generation of leukocyte and platelet forming colonies (CFU-GM) and enhancing total colony forming unit production. The methods of the invention may be used not only to regulate the differentiation of stem cells, but may also be used to stimulate the rate of colony formation, providing significant benefits to hematopoietic stem cell transplantation by improving the speed of bone marrow engraftment and recovery of leukocyte and/or platelet production.

In other embodiments, the methods of the invention may be used to regulate the differentiation of e.g., a neuronal precursor cell or neuroblast into a specific neuronal cell type such as a sensory neuron (e.g., a retinal cell, an olfactory cell, a mechanosensory neuron, a chemosensory neuron, etc.), a motor neuron, a cortical neuron, or an interneuron. In other embodiments, the methods of the invention may be used to regulate the differentiation of cell types including, but not limited to, cholinergic neurons, dopaminergic neurons, GABA-ergic neurons, glial cells (including oligodendrocytes, which produce myelin), and ependymal cells (which line the brains ventricular system). In yet other embodiments, the methods of the invention may be used to regulate the differentiation of cells that are constituent of organs, including, but not limited to, purkinje cells of the heart, biliary epithelium of the liver, beta-islet cells of the pancreas, renal cortical or medullary cells, and retinal photoreceptor cells of the eye.

Assessment of the differentiation state of stem cells obtained according to the methods of the invention may be identified by the presence of cell surface markers. Embryonic-like stem cells of the invention, for example, may be distinguished by the following cell surface markers: OCT-4+ and ABC-pt. Further, the invention encompasses embryonic-like stem cells having the following markers: CD10, CD29, CD44, CD54, CD90, SH2, SH3, SH4, OCT-4 and ABC-p, or lacking the following cell surface markers: CD34, CD38, CD45, SSEA3 and SSEA4, as described hereinabove. Such cell surface markers are routinely determined according to methods well known in the art, e.g. by flow cytometry, followed by washing and staining with an anti-cell surface marker antibody. For example, to determine the presence of CD34 or CD38, cells maybe washed in PBS and then double-stained with anti-CD34 phycoerythrin and anti-CD38 fluorescein isothiocyanate (Becton Dickinson, Mountain View, Calif.).

5.1.2. CD34+ and CD133+ Early Progenitor Cells

The present invention also provides methods of modulating human $CD34^+$ or $CD133^+$ cell differentiation. In certain embodiments, the methods of the invention encompass the regulation of stem or progenitor cell differentiation in vitro, comprising incubating the stem cells with the compound in vitro, followed by direct transplantation of the differentiated cells to a subject.

The progenitor cells obtained by the methods of the invention may be induced to differentiate along specific cell lineages, including, but not limited to, for $CD34^+$ progenitor cells, a myeloid or granulocytic, lineage, and for $CD133^+$ cells, an endothelial or neural cell lineage. In certain embodiments, progenitor cells are induced to differentiate for use in transplantation and ex vivo treatment protocols. In certain embodiments, progenitor cells are induced to differentiate into a particular cell type and genetically engineered to provide a therapeutic gene product. In a specific embodiment, progenitor cells are incubated with a compound, such as a small organic molecule, in vitro, that induces it to differentiate, followed by direct transplantation of the differentiated cells to a subject. In a preferred embodiment, the compounds that are used to control or regulate differentiation of stem cells are not polypeptides, peptides, proteins, hormones, cytokines, oligonucleotides or nucleic acids. In another preferred embodiment, the progenitor cell is caused to differentiate into a $CD34^+CD38^-CD33^+$ or $CD34^+CD38^-CD33^-$ progenitor cell.

Preferably, the methods of the invention may be used to suppress specifically the generation of red blood cells or erythropoietic colonies (BFU-E and CFU-E), while augmenting both the generation of leukocyte and platelet forming colonies (CFU-GM) and enhancing total colony forming unit production. The methods of the invention may be used not only to regulate the differentiation of stem cells, but may also be used to stimulate the rate of colony formation, providing significant benefits to hematopoietic stem cell transplantation by improving the speed of bone marrow engraftment and recovery of leukocyte and/or platelet production.

In other embodiments, the methods of the invention may be used to reduce the differentiation of $CD34^+$ progenitor cells into $CD1a^+$ cells, particularly $CD86^+CD1a^+$ cells. In another embodiment, the methods of the invention may be used to reduce or prevent the differentiation of CD34+ progenitor cells into CD14+CD1a− cells. CD14+CD1a− cells are dermal dendritic cell or monocyte/macrophage progenitor cells. In another embodiment, the methods of the invention may be used to reduce the expression on proliferating CD34+ progenitor cells of co-stimulatory molecules CD80 and CD86. In another embodiment, the methods of the invention may be used to reduce the differentiation of proliferating CD34+ progenitor cells into CD54$^{bright}$ cells, and to encourage differentiation into CD54$^{dim}$ cells. In another embodiment, the methods of the invention may be used to increase the number of CD133+ cells, which are endothelial cell progenitor cells. In yet another embodiment, the methods of the invention may be used to decrease the differentiation of proliferating CD34+ cells into CD11c−CD15+ cells, and increase differentiation into CD11c+CD15− cells, thus shifting differentiation from a myeloid dendritic cell lineage to a granulocytic lineage.

Assessment of the differentiation state of stem cells obtained according to the methods of the invention may be identified by the presence of cell surface markers. Progenitor cells of the invention, for example, may be distinguished by the CD34+ or CD133+ cell surface markers. Further, the invention encompasses proliferating progenitor cells possessing, or showing increased expression relative to a control, of one or more of the following markers: CD15, CD34, CD33, CD133, or CD54$^{dim}$, as described hereinabove. The invention further encompasses proliferating progenitor cells lacking, or showing reduced expression relative to a control, of one or more of the following markers: HLA-DR, CD1a, CD11c, CD38, CD80, CD86, CD54$^{bright}$ or CD14. In a preferred embodiment, proliferating progenitor cells of the invention exhibit CD34+CD38−CD33+ or CD34+CD38−CD33−. Such cell surface markers are routinely determined according to methods well known in the art, e.g. by washing and staining with an anti-cell surface marker antibody, followed by flow cytometry. For example, to determine the presence of CD34 or CD38, cells may be washed in PBS and then double-stained with anti-CD34 phycoerythrin and anti-CD38 fluorescein isothiocyanate (Becton Dickinson, Mountain View, Calif.).

In certain embodiment, differentiated cells may be characterized by characterizing the phagocytic capacity of the differentiated cells. The capacity of differentiated, or differentiating, cells to phagocytose may be assessed by, for example, labeling dextran with FITC and determining the amount of uptake by known methods. The capacity of differentiated, or differentiating, cells to ability to stimulate T cells may be assessed in a mixed leukocyte reaction (MLR), in which presumptively antigen-loaded cells are mixed with T cells, and the level of T cell activation is determined.

5.1.3. Identification and Characterization of Cells

In certain embodiments, differentiated cells maybe identified by characterizing differentially expressed genes (for example, characterizing a pool of genes from an undifferentiated progenitor cell(s) of interest versus a pool of genes from a differentiated cell derived from the progenitor cell). For example, nucleic acid amplification methods such as polymerase chain reaction (PCR) or. transcription-based amplification methods (e.g., in vitro transcription (IVT)) may be used to profile gene expression in different populations of cells, e.g., by use of a polynucleotide microarray. Such methods to profile differential gene expression are well known in the art (see; e.g., Wieland et al., Proc. Natl. Acad. Sci. USA 87: 2720-2724 (1990); Lisitsyn et al., Science 259: 946-951 (1993); Lisitsyn et al., Meth. Enzymology 254: 291-304 (1995); U.S. Pat. No. 5,436,142; U.S. Pat. No. 5,501,964; Lisitsyn et al., Nature Genetics 6: 57-63 (1994); Hubank and Schatz, 1994, Nucleic Acids Research 22: 5640-5648; Zeng et al., 1994, Nucleic Acids Research 22: 4381-4385; U.S. Pat. No. 5,525,471; Linsley et al., U.S. Pat. No. 6,271,002, entitled "RNA amplification method," issued Aug. 7, 2001; Van Gelder et al., U.S. Pat. No. 5,716,785, entitled "Processes for genetic manipulations using promoters," issued Feb. 10, 1998; Stoflet et al., 1988, Science 239:491-494, 1988; Sarkar and Sommer, 1989, Science 244: 331-334; Mullis et al., U.S. Pat. No. 4,683,195; Malek et al., U.S. Pat. No. 5,130,238; Kacian and Fultz, U.S. Pat. No. 5,399,491; Burg et al., U.S. Pat. No. 5,437,990; R. N Van Gelder et al. (1990), Proc. Natl. Acad. Sci. USA 87, 1663; D. J. Lockhart et al., 1996, Nature Biotechnol. 14, 1675; Shannon, U.S. Pat. No. 6,132,997; Lindemann et al., U.S. Pat. No. 6,235,503, entitled "Procedure for subtractive hybridization and difference analysis," issued May 22, 2001).

Commercially available kits are available for gene profiling, e.g., the DISPLAYPROFILE™ series of kits (Qbiogene, Carlsbad, Calif., which uses a gel-based approach for profiling gene expression. The kits utilize Restriction Fragment Differential Display-PCR(RFDD-PCR) to compare gene expression patterns in eukaryotic cells. A PCR-Select Subtraction Kit (Clontech) and a PCR-Select Differential Screening Kit (Clontech) may also be used, which permits identification of differentially expressed clones in a subtracted library. After generating pools of differentially expressed genes with the PCR-Select Subtraction kit, the PCR-Select Differential Screening kit is used. The subtracted library is hybridized with probes synthesized directly from tester and driver populations, a probe made from the subtracted cDNA, and a probe made from reverse-subtracted cDNA (a second subtraction performed in reverse). Clones that hybridize to tester but not driver probes are differentially expressed; however, non-subtracted probes are not sensitive enough to detect rare messages. Subtracted probes are greatly enriched for differentially expressed cDNAs, but may give false positive results. Using both subtracted and non-subtracted probes according to the manufacturer's (Clontech) instructions identifies differentially expressed genes.

In another embodiment, differentiated stem or progenitor cells are identified and characterized by a colony forming unit assay, which is commonly known in the art, such as MESENCULT® medium (Stem Cell Technologies, Inc., Vancouver British Columbia).

Determination that a stem cell or progenitor has differentiated into a particular cell type may be accomplished by methods well-known in the art, e.g. measuring changes in morphology and cell surface markers using techniques such as flow cytometry or immunocytochemistry (e.g., staining cells with tissue-specific or cell-marker specific antibodies), by examination of the morphology of cells using light or confocal microscopy, or by measuring changes in gene expression using techniques well known in the alt, such as PCR and gene-expression profiling.

5.2. Stem and Progenitor Cell Populations

The present invention provides methods of modulating human stem cell differentiation. Any mammalian stem cell can be used within the methods of the invention, including, but not limited to, stem cells isolated from cord blood (CB cells), peripheral blood, adult blood, bone marrow, placenta, mesenchymal stem cells and other sources. In a non-preferred embodiment, the stem cells are embryonic stem cells or cells that have been isolated from sources other than placenta.

Sources of mesenchymal stem cells include bone marrow, embryonic yolk sac, placenta, umbilical cord, fetal and adolescent skin, and blood. Bone marrow cells may be obtained, for example, from iliac crest, femora, tibiae, spine, rib or other medullary spaces.

The stem cells to be used in accordance with the methods of the present invention may include pluripotent cells, i.e., cells that have complete differentiation versatility, that are self-renewing, and can remain dormant or quiescent within tissue. The stem cells may also include multipotent cells, committed progenitor cells, and fibroblastoid cells. In one preferred embodiment, the invention utilizes stem cells that are viable, quiescent, pluripotent stem cells isolated from a full-term exsanguinated perfused placenta.

Stem cell populations may consist of placental stem cells obtained through a commercial service, e.g. LifeBank USA (Cedar Knolls, N.J.), ViaCord (Boston Mass.), Cord Blood Registry (San Bruno, Calif.) and Cryocell (Clearwater, Fla.).

Stem cell populations may also consist of placental stem cells collected according to the methods disclosed in U.S. Application Publication No. US 20020123141, published Sep. 5, 2002, entitled "Method of Collecting Placental Stem Cells" and U.S. Application Publication No. US 20030032179, published Feb. 13, 2003, entitled "Post-Partum Mammalian Placenta, Its Use and Placental Stem Cells Therefrom" (both of which are incorporated herein by reference in their entireties).

In one embodiment, stem cells from cord blood may be used. The first collection of blood from the placenta is referred to as cord blood, which contains predominantly $CD34^+$ and $CD38^+$ hematopoietic progenitor cells. Within the first twenty-four hours of postpartum perfusion, high concentrations of $CD34^+CD38^-$ hematopoietic progenitor cells may be isolated from the placenta. After about twenty-four hours of perfusion, high concentrations of $CD34^-CD38^-$ cells can be isolated from the placenta along with the aforementioned cells. The isolated perfused placenta of the invention provides a source of large quantities of stem cells enriched for $CD34^+$ $CD38^-$ stem cells and $CD34^-CD38^+$ stem cells: The isolated placenta that has been perfused for twenty-four hours or more provides a source of large quantities of stem cells enriched for $CD34^-$ and $CD38^-$ stem cells.

Preferred cells to be used in accordance with the present invention are embryonic-like stem cells that originate from an exsanguinated perfused placenta, or cells that derive from embryonic-like placental stem cells. The embryonic-like stem cells off the invention may be characterized by measuring changes in morphology and cell surface markers using techniques such as flow cytometry and immunocytochemistry, and measuring changes in gene expression using techniques, such as PCR. In one embodiment of the invention, such embryonic-like stem cells may be characterized by the presence of the following cell surface markers: CD10, CD29, CD44, CD54, CD90, SH2, SH3, SH4, OCT-4 and ABC-p, or the absence of the following cell surface markers: CD34, CD38, CD45, SSEA3 and SSEA4. In a preferred embodiment, such embryonic-like stem cells may be characterized by the presence of cell surface markers OCT-4 and APC-p. Such cell surface markers are routinely determined according to methods well known in the art, e.g. by flow cytometry, followed by washing and staining with an anti-cell surface marker antibody. For example, to determine the presence of CD34 or CD38, cells may be washed in PBS and then double-stained with anti-CD34 phycoerythrin and anti-CD38 fluorescein isothiocyanate (Becton Dickinson, Mountain View, Calif.).

Embryonic-like stem cells originating from placenta have characteristics of embryonic stem cells but are not derived from the embryo. In other words, the invention encompasses the use of OCT-4+ and ABC-p+ cells that are undifferentiated stem cells that are isolated from a postpartum perfused placenta. Such cells are as versatile (e.g., pluripotent) as human embryonic stem cells. As mentioned above, a number of different pluripotent or multipotent stem cells can be isolated from the perfused placenta at different time points e.g., CD34+CD38+, CD34+CD38−, and CD34−CD38− hematopoietic cells. According to the methods of the invention, human placenta is used post-birth as the source of embryonic-like stem cells.

For example, after expulsion from the womb, the placenta is exsanguinated as quickly as possible to prevent or minimize apoptosis. Subsequently, as soon as possible after exsanguination the placenta is perfused to remove blood, residual cells, proteins, factors and any other materials present in the organ. Materials debris may also be removed from the placenta. Perfusion is normally continued with an appropriate perfusate for at least two to more than twenty-four hours. In several additional embodiments the placenta is perfused for at least 4, 6, 8, 10, 12, 14, 16, 18, 20, and 22 hours. In other words, this invention is based at least in part on the discovery that the cells of a postpartum placenta can be activated by exsanguination and perfusion for a sufficient amount of time. Therefore, the placenta can readily be used as a rich and abundant source of embryonic-like stem cells, which cells can be used for research, including drug discovery, treatment and prevention of diseases, in particular transplantation surgeries or therapies, and the generation of committed cells, tissues and organoids. See co-pending application Ser. No. 10/004,942, filed Dec. 5, 2001 entitled "Method of Collecting Placental Stem Cells" and application Ser. No. 10/076,180, filed Feb. 13, 2002, entitled "Post-Partum Mammalian Placenta, Its Use and Placental Stem Cells Therefrom," both of which are incorporated herein by reference in their entireties.

Embryonic-like stem cells are extracted from a drained placenta by means of a perfusion technique that utilizes either or both of the umbilical artery and umbilical vein. The placenta is preferably drained by exsanguination and collection of residual blood (e.g., residual umbilical cord blood). The drained placenta is then processed in such a manner as to establish an ex vivo, natural. bioreactor environment in which resident embryonic-like stem cells within the parenchyma and extravascular space are recruited. The embryonic-like stem cells migrate into the drained, empty microcirculation where, according to the methods of the invention, they are collected, preferably by washing into a collecting vessel by perfusion.

Specifically contemplated as part of the invention is the modulation of $CD34^+$ and $CD133^+$ progenitor cells into myeloid cells, particularly dendritic or granulocytic cells. Recent reports indicate that such cells are pluripotent; thus, the invention also contemplates the modulation of the development of these progenitor into cells of the brain, kidney, intestinal tract, liver or muscle.

Any mammalian, avian or reptilian $CD34^+$ or $CD133^+$ stem or progenitor cell can be used within the methods of the invention, including, but not limited to, stem cells isolated from cord blood (CB cells), peripheral blood, adult blood, bone marrow, placenta, including perfused placenta (see U.S. Application Publication No. US 20030032179, published Feb. 13, 2003, entitled "Post-Partum Mammalian Placenta, Its Use and Placental Stem Cells Therefrom", which is incorporated herein by reference in its entirety), mesenchymal stem cells and other sources. In a preferred embodiment, the stem cells are hematopoietic stem cells or cells that have been isolated from bone marrow. Such cells may be obtained from other organs or tissues, but such sources are less preferred.

In one embodiment, progenitor cells from cord blood or from postpartum placenta may be used. As noted above, cord blood contains predominantly CD34+ and CD38+ hematopoietic progenitor cells. Within the first twenty-four hours of postpartum perfusion, high concentrations of CD34+CD38− hematopoietic progenitor cells may be isolated from an isolated, perfused placenta. After about twenty-four hours of perfusion, high concentrations of CD34− CD38− cells can be isolated from the placenta along with the aforementioned cells. In another embodiment, progenitor cell populations may be obtained through a commercial service, e.g., Life-Bank USA (Cedar Knolls, N.J.), ViaCord (Boston Mass.), Cord Blood Registry (San Bruno, Calif.) and Cryocell (Clearwater, Fla.).

5.3. The Compounds of the Invention

Compounds used in the invention are referred to herein as "immunomodulatory compounds," and include immunomodulatory compounds that are racemic, stereomerically enriched or stereomerically pure and pharmaceutically acceptable salts, solvates, hydrates, stereoisomers, clathrates, and prodrugs thereof. Preferred compounds used in the invention are small organic molecules having a molecular weight less than about 1000 g/mol, and are not proteins, peptides, oligonucleotides, oligosaccharides or other macromolecules.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. As used herein and unless otherwise indicated, the term "enantiomerically pure" means a stereomerically pure composition of a compound having one chiral center. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein, the term "enantiomerically pure" means a stereomerically pure composition of a compound having one chiral center. Similarly, the term "enantiomerically enriched" means a stereomerically enriched composition of a compound having one chiral center.

As used herein and unless otherwise indicated, the term "immunomodulatory compounds" or "IMIDS®" (Celgene Corporation) used herein encompasses small organic molecules that markedly inhibit TNF-α, LPS induced monocyte IL 1α and IL 12, and partially inhibit IL6 production. Specific immunomodulatory compounds of the invention are discussed below. These compounds can be obtained commercially from, for example, Celgene, or prepared in accordance with the methods described in the patents or publications listed herein.

TNF-α is an inflammatory cytokine produced by macrophages and monocytes during acute inflammation. TNF-α is responsible for a diverse range of signaling events within cells. TNF-α may play a pathological role in cancer. Without being limited by particular theory, one of the biological effects exerted by the immunomodulatory compounds of the invention is the reduction of synthesis of TNF-α. Immunomodulatory compounds of the invention enhance the degradation of TNF-α mRNA.

Further, without being limited by particular theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells.

Specific examples of immunomodulatory compounds of the invention, include, but are not limited to, cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide and EM-12), including, but not limited to, those disclosed in U.S. Pat. No. 5,635,517; and a class of non-polypeptide cyclic amides disclosed in U.S. Pat. Nos. 5,698,579 and 5,877,200. The entirety of each of the patents identified herein are incorporated herein by reference. Immunomodulatory compounds of the invention do not include thalidomide.

Other specific immunomodulatory compounds of the invention include, but are not limited to, 1-oxo- and 1,3 dioxo-2-(2,6-dioxopiperidin-3-yl) isoindolines substituted with amino or substituted amino in the benzo ring as described in U.S. Pat. No. 5,635,517 which is incorporated herein. These compounds have the structure I:

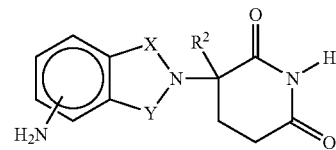

in which one of X and Y is C=O, the other of X and Y is C=O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;

1-oxo-2-(2,6-dioxopiperidin-3-yl)-5-aminoisoindoline;

1-oxo-2-(2,6-dioxopiperidin-3-yl)-6-aminoisoindoline;

1-oxo-2-(2,6-dioxopiperidin-3-yl)-7-aminoisoindoline;

1,3-dioxo-2-(2,6-dioxopiperidin-3-yl)-4-aminoisoindoline;

and 1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein. Compounds representative of this class are of the formulas:

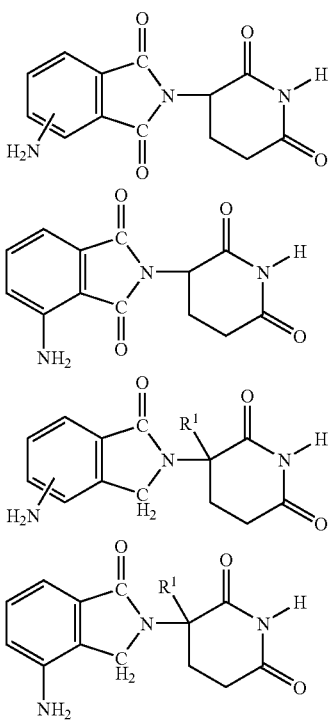

wherein R¹ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. patent application Ser. Nos. 10/032,286 and 09/972,487, and International Application No. PCT/US01/50401 (International Publication No. WO 02/059106), each of which are incorporated herein by reference. Representative compounds are of formula II:

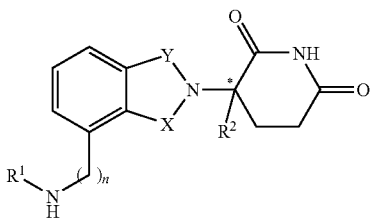

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O—R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl $OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl$(C_1-C_6)$heterocycloalkyl, $(C_0-C_4)$alkyl$(C_2-C_5)$heteroaryl, $(C_5-C_8)$alkyl-$N(R^6)_2$; $(C_0-C_8)$alkyl-NH—C(O)O—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$alkyl or benzyl.

In other specific compounds of formula II, $R^1$ is H, $(C_1-C_8)$alkyl, benzyl, $CH_2OCH_3$, $CH_2CH_2OCH_3$, or

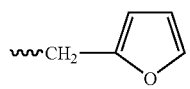

In another embodiment of the compounds of formula II, $R^1$ is

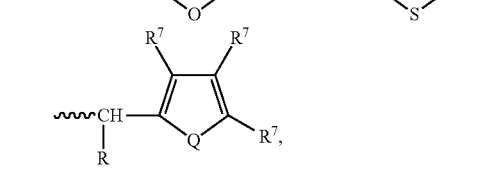

wherein Q is O or S, and each occurrence of $R^7$ is independently H, $(C_1-C_8)$alkyl, benzyl, $CH_2OCH_3$, or $CH_2CH_2OCH_3$.

In other specific compounds of formula II, $R^1$ is $C(O)R^3$.

In other specific compounds of formula II, $R^3$ is $(C_0-C_4)$alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O)NHC(O) can be replaced with $(C_1-C_4)$alkyl, aryl, or benzyl.

Still other specific immunomodulatory compounds of the invention belong to a class of isoindole-imides disclosed in U.S. patent application Ser. No. 09/781,179, International Publication No. WO 98/54170, and U.S. Pat. No. 6,395,754, each of which are incorporated herein by reference. Representative compounds are of formula III:

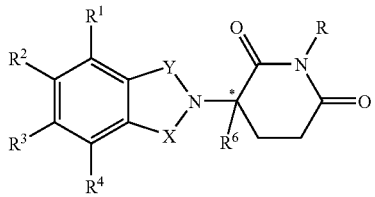

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or CH2OCOR';

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2[X]X_1CH_2CH_2$— in which [X]$X_1$ is —O—, —S—, or —NH—;

$R^{10}$ is hydrogen, alkyl of to 8 carbon atoms, or phenyl; and

\* represents a chiral-carbon center.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione (ACTIMID™) has the following chemical structure:

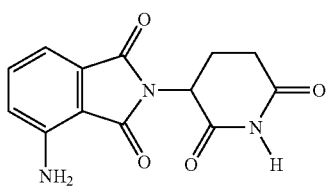 [SMILES: Nc1cccc2c1C(=O)N(C1CCC(=O)NC1=O)C2=O]

3-(4-amino-1-oxo-1,3-dihydro-isoindol-2-yl)-piperidine-2,6-dione (REVIMID™) has the following chemical structure:

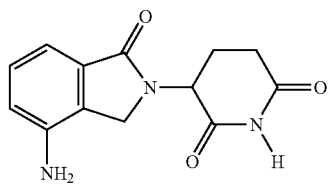 [SMILES: Nc1cccc2c1CN(C1CCC(=O)NC1=O)C2=O]

5.4. Methods of Stem Cell Culture

In certain embodiments of the invention, stem or progenitor cells, including but not limited to embryonic stem cells, embryonic-like stem cells, progenitor cells, pluripotent cells, totipotent cells, multipotent cells, cells endogenous to a postpartum perfused placenta, cord blood cells, stem or progenitor cells derived from peripheral blood or adult blood, or bone marrow cells, are exposed to the compounds of the invention and induced to differentiate. These cells may be propagated in vitro using methods well known in the art, or alternatively, may be propagated in a postpartum perfused placenta.

In certain embodiments, cells endogenous to a postpartum perfused placenta may be collected from the placenta and culture medium and cultured in vitro under conditions appropriate, and for a time sufficient, to induce differentiation to the desired cell type or lineage. See U.S. Application Publication No. US 20030032179, published Feb. 13, 2003, entitled "Post-Partum Mammalian Placenta, Its Use and Placental Stem Cells Therefrom" which is hereby incorporated in its entirety.

In another embodiment of the invention, the stem or progenitor cells are not derived from a postpartum perfused placenta but instead, are isolated from other sources such as cord blood, bone marrow, peripheral blood or adult blood, are exposed to the compounds of the invention and induced to differentiate. In a preferred embodiment, the differentiation is conducted in vitro under conditions appropriate, and for a time sufficient, to induce differentiation into the desired lineage or cell type. The compounds of the invention are used in the differentiation/culture media by addition, in situ generation, or in any other manner that permits contact of the stem or progenitor cells with the compounds of the invention.

In another embodiment, the cultured stem cells, e.g., stem cells cultured in vitro or in a postpartum perfused placenta, are stimulated to proliferate in culture, for example, by administration of erythropoietin, cytokines, lymphokines, interferons, colony stimulating factors (CSFs), interferons, chemokines, interleukins, recombinant human hematopoietic growth factors including ligands, stem cell factors, thrombopoietin (Tpo), interleukins, and granulocyte colony-stimulating factor (G-CSF) or other growth factors.

After collection and/or isolation of the cultured cells, they may be identified and characterized by a colony forming unit assay, which is commonly known in the art, such as MESEN-CULT® medium (Stem Cell Technologies, Inc., Vancouver British Columbia).

Methods for culturing stem or progenitor cells in vitro are well known in the art, e.g., see, Thomson et al., 1998, Science 282:1145-47 (embryonic stem cells); Hirashima et al., 1999, Blood 93(4): 1253-63, and. Hatzopoulos et al., 1998, Development 125:1457-1468 (endothelial cell progenitors); Slager et al., 1993, Dev. Genet. 14(3):212-24 (neuron or muscle progenitors); Genbachev et al., 1995, Reprod. Toxicol. 9(3): 245-55 (cytotrophoblasts, i.e., placental epithelial cell progenitors); Nadkarni et al. 1984, Tumori 70:503-505, Melchner et al., 1985, Blood 66(6): 1469-1472, international PCT publication WO 00/27999 published May 18, 2000, Himori et al., 1984, Intl. J. Cell Cloning 2:254-262, and Douay et al., 1995, Bone Marrow Transplantation 15:769-775 (hematopoietic progenitor cells); Shamblott et al., 1998, Proc. Natl. Acad. Sci. USA 95:13726-31 (primordial germ cells); Yan et al., 2001, Devel. Biol. 235:422-432 (trophoblast stem cells). Such methods may be easily adapted for use in the methods of the invention, provided that the culture of the progenitor cells includes a step or steps of culturing the cells with a compound of the invention, at the times indicated, to produce the desired population(s) of differentiated cells.

5.4.1. Stem Cell Culture In Vitro

The methods of the invention encompass the regulation of stem cell or progenitor cell differentiation in vitro, comprising incubating the cells with a compound, such as a small organic molecule of the present invention, in vitro, that induces them to differentiate into cells of a particular desired cell lineage, followed by direct transplantation of the differentiated cells to a subject. In a preferred embodiment, the cells are induced to differentiate into a hematopoietic cell lineage.

In certain embodiments, the cultured stem cells of interest are exposed in vitro to a 0.1 µg/ml, 0.2 µg/ml, 0.3 µg/ml, 0.4 µg/ml, 0.5 µg/ml, 1 µg/ml, 5 µg or 10 µg/ml concentration of a compound of the invention. Preferably the cells of interest are exposed to a concentration of Thalidomide of about 0.005 µg/ml to about 5 mg/ml, a concentration of ACTIMID™ of about 0.005 µg/ml to about 5 mg/ml, (Celgene Corp., Warren, N.J.), a concentration of REVIMID™ (Celgene Corp., Warren, N.J.) of about 0.005 µg/ml to about 5 mg/ml, a concentration of ACTIMID™ (Celgene Corp., Warren, N.J.) of about 0.005 µg/ml to about 5 mg/ml or a concentration of REVIMID™ (Celgene Corp., Warren, N.J.) of about 0.005 µg/ml to about 5 mg/ml (see also Section 5.7, "Pharmaceutical Compositions").

In certain embodiments, the embryonic-like stem cells are induced to propagate in the placenta bioreactor by introduction of nutrients, hormones, vitamins, growth factors, or any combination thereof, into the perfusion solution. Serum and other growth factors may be added to the propagation perfusion solution or medium. Growth factors are usually proteins and include, but are not limited to: cytokines, lymphokines, interferons, colony stimulating factors (CSFs), interferons, chemokines, and interleukins. Other growth factors that may be used include recombinant human hematopoietic growth factors including ligands, stem cell factors, thrombopoietin (Tpo), granulocyte colony-stimulating factor (G-CSF), leukemia inhibitory factor, basic fibroblast growth factor, placenta derived growth factor and epidermal growth factor.

The growth factors introduced into the perfusion solution can stimulate the propagation of undifferentiated embryonic-like stem cells, committed progenitor cells, or differentiated cells (e.g., differentiated hematopoietic cells). The growth factors can stimulate the production of biological materials and bioactive molecules including, but not limited to, immunoglobulins, hormones, enzymes or growth factors as previously described. The cultured placenta should be "fed" periodically to remove the spent media, depopulate released cells, and add fresh media. The cultured placenta should be stored under sterile conditions to reduce the possibility of contamination, and maintained under intermittent and periodic pressurization to create conditions that maintain an adequate supply of nutrients to the cells of the placenta. It should be recognized that the perfusing and culturing of the placenta can be both automated and computerized for efficiency and increased capacity.

5.4.2. Progenitor Cell Culture In Vitro

The methods of the invention also encompass the regulation and modulation of the development of progenitor cells, particularly $CD34^+$ and $CD133^+$ progenitor cells. In one embodiment of the invention, progenitor cells are induced to differentiate into a hematopoietic cell lineage. In a specific embodiment, the lineage is a granulocytic lineage. In an alternate embodiment, $CD133^+$ cells are induced to differentiate into endothelial cells, brain cells, kidney cells, liver cells or intestinal tract cells.

Progenitor cells may be cultured by standard methods, as noted above. Additionally, the culture of the progenitor cells may comprise contacting the cells at various times or time frames during culture, so as to drive progenitor cell differentiation down different cell lineages.

Thus, in one method of culturing $CD34^+$ or $CD133^+$ progenitor cells, cells are plated at day 0 in medium containing stem cell factor (SCF), Flt-3L, GM-CSF and TNF-α and cultured for six days. On the sixth day, the cells are re-plated in medium containing GM-CSF and TNF-α, and culture is continued for an additional six days. This method results in the generation of dendritic cells. In a variation of this method, the cells are initially plated in medium containing GM-CSF and IL-4, then switched on the sixth day to monocyte-conditioned medium (see Steinman et al., International Publication No. WO 97/29182). To produce a population of $CD34^+CD38^-CD33^+$ or $CD34^+CD38^-CD33^-$ progenitor cells, the progenitor cells are placed in contact with a compound of the invention at day 0, and $CD34^+CD38^-CD33^+$ or $CD34^+CD38^-CD33^-$ progenitor cells are collected at day 6.

The inventors have discovered that the timing of the addition of the compound(s) of the invention, particularly ACTIMID™ or REVIMID™, has a substantial effect upon the path of differentiation of $CD34^+$ cells into cells of particular lineages, and on the differentiation of $CD133^+$ cells. $CD34^+$ progenitor cells, cultured under standard conditions, follow a myeloid developmental pathway or lineage, i.e., become dendritic cells within 12 days after initial plating (i.e., after initial culture). However, the addition of a compound of the invention at one of several particular times during the first six days of culture substantially alters this pathway. For example, if $CD34^+$ cells, particularly $CD34^+$ derived from bone marrow, are exposed to a compound of the invention, particularly ACTIMID™ or REVIMID™ on the first day of culture, differentiation along the myeloid lineage is suppressed, as evidenced by the increase in the number of $CD34^+CD38^-$ cells and decrease in the number of $CD1a^+CD14-$ cells at day 6 of culture, relative to a control not exposed to a compound of the invention (i.e., exposed to DMSO). Moreover, exposure to a compound of the invention leads to suppression of the development of cells expressing surface markers expressed by cells in a dendritic cell lineage, such as CD80 and CD86. Contact at the initial day of culture, or at any point up to three days after the initial day of culture, with a compound of the invention, leads to such modulation of the development of $CD34^+$ progenitor cells. The increase in the number of $CD34^+$ cells is intensified if multiple doses of a compound of the invention are given between day 0 and day 6, for example, doses at day 0 and day 2, day 0 and day 4, doses at day 3 and day 6, or doses at day 2, day 4, and day 6.

In a particularly useful aspect of the invention, the addition of a compound of the invention at the first day of $CD34^+$ progenitor cell culture, and continuing the exposure through day 12, leads to the development of a unique progenitor cell expressing a unique combination of cell surface markers: $CD34^+CD38^-CD33^+$ or $CD34^+CD38^-CD33^-$. The $CD34^+CD38^-CD33^+$ or $CD34^+CD38^-CD33^-$ cell population represents an intermediate stage in differentiation. This population is useful as an expandable population of progenitor cells that may readily be transplanted to a patient in need of a rapidly-developing population of hematopoietic lineage cells, for example, granulocytic cells. In another embodiment, $CD34^+$ cells may be plated and cultured during the proliferative phase (approximately 6 days) in standard medium (i.e., not exposed to ACTIMID™, REVIMID™ or the like), then switched to the same or a similar medium containing ACTIMID™ or the like, and continuing the culture until day 12. In this embodiment, the differentiating cells typically show decreased expression of CD80, CD86 and CD14, but result in an increased persistence of a $CD1a^+$ cell population relative to controls. Such differentiating cells are not blocked from becoming dendritic cells. In another embodiment, $CD34^+$ cells are treated during the proliferative phase (days 1-6 post-plating) for at least three consecutive days with ACTIMID™, REVIMID™, or another compound of the invention. In yet another embodiment, $CD34^+$ or $CD133^+$ progenitor cells are treated two or more times with ACTIMID™, REVIMID™, or another compound of the invention, during the first six days after plating. Such multiple treatments result in an increase in the proliferation of both $CD34^+$ or $CD133^+$ populations. Multiple treatments with ACTIMID™, or another compound of the invention, also causes a shift in the differentiation of $CD34^+$ progenitor cells away from a $CD11c^+CD15^-$ lineage and towards a $CD11c^-CD15^+$ lineage, i.e., away from a myeloid dendritic cell lineage and towards a granulocytic lineage (FIG. 6B).

Treatment of the progenitor cells from day 0 of culture, particularly multiple doses between day 0 and day 6, also results in an increase in the number of $CD133^+$ progenitor cells, particularly an increase in the $CD34^+CD133^+$ progenitor population. $CD133^+$ is a hematopoietic marker that is an alternative to CD34 isolation, as CD133+ cells can be expanded in the same manner as the $CD34^+$ subset and conserve their multilineage capacity (see Kobari et al., *J. Hematother. Stem Cell Res.* 10(2):273-81 (2001)). CD133+ has been reported to be present in $CD34^-$ cells from human fetal brain tissue, and showed potent engraftment, proliferation, migration, and neural differentiation when injected into neonatal mice (see *Proc. Natl. Acad. Sci. USA.* 19:97(26):14720-5 (2000)). $CD133^+$ hematopoietic stem cells have been shown to be enriched for progenitor activity with enlarged clonogenic capacity and higher engraftment in NOD-SCID mice.

The above notwithstanding, if a compound of the invention is placed in contact with proliferating $CD34^+$ progenitor cells after three days of culture (i.e., at any time between 3-6 days after initial culture), the proliferating progenitor cells, which have already begun expressing the cell surface marker CD1a, show a substantially increased persistence of the expression of this marker relative to DMSO-treated controls. It is important to note that no cytotoxicity is associated with this increased persistence. In other words, treatment with ACTIMID™ does not cause other cell populations to apoptose. The net effect is a maintenance of existing immune capability and the development of new immune capability.

Thus, in one embodiment of the method of the invention, differentiation of $CD34^+$ cells into dendritic cells is modulated (i.e., suppressed) by contacting $CD34^+$ progenitor cells with a compound of the invention at day 0 of culture (i.e., the first day of culture). In another embodiment, differentiation of $CD34^+$ cells into granulocytic cells is enhanced by contacting $CD34^+$ progenitor cells with a compound of the invention at day 0 of culture (i.e., the first day of culture). In another embodiment, differentiation of $CD34^+$ cells into a $CD34^+$ $CD38^-CD33^+$ or a $CD34^+CD38^-$-$CD33^-$ progenitor cell population is enhanced by contacting $CD34^+$ progenitor cells with a compound of the invention during the first three days of culture. In another embodiment, a $CD34^+CD133^+$ population is enhanced or increased by contacting progenitor cells with a compound of the invention in multiple doses from day 0 to day 6 of culture. In another embodiment, the persistence of a $CD1a^+$ cell population is enhanced or increased by contacting $CD34^+$ progenitor cells with a compound of the invention at day 6 of culture, wherein said $CD34^+$ cells differentiate into cells exhibiting the CD1a surface marker, and wherein said culture includes no contact with said compound for up to six days.

In the above embodiments, it will be understood that such variations in administration of ACTIMID™, REVIMID™, or a related compound may be made to the progenitor cells in vivo, e.g., such as in a patient into whom such cells have been transplanted or engrafted, as well as to the progenitor cells in vitro.

The methods of the invention encompass the regulation of stem cell or progenitor cell differentiation in vitro, comprising incubating the cells with a compound, such as a small organic molecule of the present invention, in vitro, that induces them to differentiate into cells of a particular desired cell lineage, followed by direct transplantation of the differentiated cells to a subject. In a preferred embodiment, the cells are induced to differentiate into a hematopoietic cell lineage. In an alternate embodiment, $CD133^+$ cells are induced to differentiate into endothelial cells, brain cells, kidney cells, liver cells, or intestinal tract cells.

It should be noted that the methods described herein are contemplated for use with $CD34^+$ or $CD133^+$ progenitor cells derived from mammals, preferably humans, but are also contemplated for use with avian or reptilian progenitor cells. The compounds of the invention, however, are potentially variably potent depending upon the species from which the progenitor cells are derived. Some variation in the culturing methods, particularly with regard to the concentration of the compound(s) administered, is therefore also contemplated. For example, progenitor cells of murine origin are less sensitive to the compounds of the invention, for example ACTIMID™, and would require higher concentrations to achieve the effects obtainable at 1 µM with progenitor cells of human origin. Persons of skill in the art would understand that such optimizations are routine.

5.5. Genetic Engineering of Stem and Progenitor Cells

In another embodiment of the invention, stem or progenitor cells to be differentiated in accordance with the methods of the invention are genetically engineered either prior to, or after exposure to the compounds of the invention, using, for example, a viral vector such as an adenoviral or retroviral vector, or by using mechanical means such as liposomal or chemical mediated uptake of the DNA. In specific embodiments, the $CD34^+$ progenitor cells are genetically engineered, then treated with a compound of the invention; in more specific embodiments, said compound is ACTIMID™, REVIMID™, or an analog of either. In another embodiment, said cells are treated with a compound of the invention, then genetically engineered.

A vector containing a transgene can be introduced into a cell of interest by methods well known in the art, e.g., transfection, transformation, transduction, electroporation, infection, microinjection, cell fusion, DEAE dextran, calcium phosphate precipitation, liposomes, LIPOFECTIN™, lysosome fusion, synthetic cationic lipids, use of a gene gun or a DNA vector transporter, such that the transgene is transmitted to daughter cells, e.g., the daughter embryonic-like stem cells or progenitor cells produced by the division of an embryonic-like stem cell. For various techniques for transformation or transfection of mammalian cells, see Keown et al., 1990, Methods Enzymol. 185: 527-37; Sambrook et al., 2001, Molecular Cloning, A Laboratory Manual, Third Edition, Cold Spring Harbor Laboratory Press, N.Y.

Preferably, the transgene is introduced using any technique, so long as it is not destructive to the cell's nuclear membrane or other existing cellular or genetic structures. In certain embodiments, the transgene is inserted into the nucleic genetic material by microinjection. Microinjection of cells and cellular structures is commonly known and practiced in the art.

For stable transfection of cultured mammalian cells, such as cells culture in a placenta, only a small fraction of cells may integrate the foreign DNA into their genome. The efficiency of integration depends upon the vector and transfection technique used. In order to identify and select integrants, a gene that encodes a selectable marker (e.g., for resistance to antibiotics) is generally introduced into the host embryonic-like stem cell along with the gene sequence of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die). Such methods are particularly useful in methods involving homologous recombination in mammalian cells (e.g., in embryonic-like stem cells) prior to introduction or transplantation of the recombinant cells into a subject or patient.

A number of selection systems may be used to select transformed host stem cells, such as embryonic-like cells, or progenitor cells, such as $CD34^+$ or $CD133^+$ progenitor cells. In particular, the vector may contain certain detectable or selectable markers. Other methods of selection include but are not limited to selecting for another marker such as: the herpes simplex virus thymidine kinase (Wigler et al., 1977, Cell 11: 223), hypoxanthine-guanine phosphoribosyltransferase (Szybalska and Szybalski, 1962, Proc. Natl. Acad. Sci. USA 48: 2026), and adenine phosphoribosyltransferase (Lowy et al., 1980, Cell 22: 817) genes can be employed in tk-, hgprt- or aprt-cells, respectively. Also, antimetabolite resistance can be used as the basis of selection for the following genes: dhfr, which confers resistance to methotrexate (Wigler et al., 1980, Proc. Natl. Acad. Sci. USA 77: 3567; O'Hare et al., 1981, Proc. Natl. Acad. Sci. USA 78: 1527); gpt, which confers resistance to mycophenolic acid (Mulligan and Berg, 1981, Proc. Natl. Acad. Sci. USA 78: 2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30: 147).

The transgene may integrate into the genome of the cell of interest, preferably by random integration. In other embodiments the transgene may integrate by a directed method, e.g., by directed homologous recombination (i.e., "knock-in" or "knock-out" of a gene of interest in the genome of cell of interest), Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al. issued, May 6, 1997; U.S. Pat. No. 5,487,992, Capecchi et al., issued Jan. 30, 1996).

Methods for generating cells having targeted gene modifications through homologous recombination are known in the art. The construct will comprise at least a portion of a gene of interest with a desired genetic modification, and will include regions of homology to the target locus, i.e., the endogenous copy of the targeted gene in the host's genome. DNA constructs for random integration, in contrast to those used for homologous recombination, need not include regions of homology to mediate recombination. Markers can be included in the targeting construct or random construct for performing positive and negative selection for insertion of the transgene.

To create a homologous recombinant cell, e.g., a homologous recombinant embryonic like stem cell, endogenous placental cell or exogenous cell cultured in the placenta, a homologous recombination vector is prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecchi, 1987, Cell 51: 503; Bradley, 1991, Curr. Opin. Bio/Technol. 2: 823-29; and PCT Publication Nos. WO 90/11354, WO 91/01140, and WO 93/04169.

In a specific embodiment, the methods of Bonadio et al. (U.S. Pat. No. 5,942,496, entitled Methods and compositions for multiple gene transfer into bone cells, issued Aug. 24, 1999; and PCT WO95/22611, entitled Methods and compositions for stimulating bone cells, published Aug. 24, 1995) are used to introduce nucleic acids into a cell of interest, such as a stem cell, progenitor cell or exogenous cell cultured in the placenta, e.g., bone progenitor cells.

5.6. Uses of Stem Cells and Progenitor Cells Conditioned for Differentiation 5.6.1. General Uses The stem cells and $CD34^+$ and $CD133^+$ progenitor of the invention may be induced to differentiate for use in transplantation and ex vivo treatment protocols. In one embodiment, the stem cell populations are differentiated to a particular cell type and genetically engineered to provide a therapeutic gene product. In another embodiment, the progenitor cell populations are expanded into early progenitor cells and genetically engineered to provide a therapeutic gene product. In another embodiment, the progenitor cell populations are differentiated to a particular cell type, such as a granulocyte, and genetically engineered to provide a therapeutic gene product.

The compounds of the invention also have utility in clinical settings in which transplantation has the principle objective of restoring bone marrow white blood cell production, such as the reversal of neutropenia and leukopenia, which result from disease and/or clinical myeloablation. The compounds also have utility in the restoration of production of early progenitor cells or granulocytes, which result from disease, various known therapeutic side effects, or myeloablation. The compounds of the invention also have utility in cases in which the suppression of red blood cell generation is preferred, without bone marrow suppression.

In certain embodiments, stem cells that have been treated with the compounds of the invention are administered along with untreated cells, such as stem cells from cord blood or peripheral blood, to a patient in need thereof. In other embodiments, $CD34^+$ or $CD133^+$ cells that have been treated with the compounds of the invention are administered along with untreated cells, such as stem cells from cord blood or peripheral blood, to a patient in need thereof. In one embodiment, CD34+ progenitor cells, treated from the first day of culture with a compound of the invention, are administered with untreated cells to a patient in need thereof. In a more specific embodiment, the progenitor cell transferred is a CD34$^+$CD38$^-$CD33$^+$ or a CD34$^+$CD38$^-$CD33$^-$ progenitor cell.

Stem cells, e.g., embryonic-like or hematopoietic stem cells, or progenitor cells, the differentiation of which has been modulated according to the methods of the invention, may be formulated as an injectable (see PCT WO 96/39101, incorporated herein by reference in its entirety). In an alternative embodiment, cells and tissues, the differentiation of which has been modulated according to the methods of the invention, may be formulated using polymerizable or cross linking hydrogels as described in U.S. Pat. Nos. 5,709,854; 5,516,532; or 5,654,381, each of which is incorporated by reference in its entirety.

Embryonic-like stem cells may be used instead of specific classes of progenitor cells (e.g., chondrocytes, hepatocytes, hematopoietic cells, pancreatic parenchymal cells, neuroblasts, muscle progenitor cells, etc.) in therapeutic or research protocols in which progenitor cells would typically be used.

5.6.2. Tissue Replacement or Augmentation

The stem cells, particularly embryonic-like stem cells, and progenitor cells, of the invention, the differentiation of which has been modulated according to the methods of the invention, can be used for a wide variety of therapeutic protocols directed to the transplantation or infusion of a desired cell population, such as a stem cell or progenitor cell population. The stem or progenitor cells can be used to replace or augment existing tissues, to introduce new or altered tissues, or to join together biological tissues or structures.

In a preferred embodiment of the invention, stem cells, such as embryonic-like stem cells from the placenta, or progenitor cells such as hematopoietic progenitor cells, the differentiation of which has been modulated according to the methods of the invention, may be used as autologous and allogenic, including matched and mismatched HLA type, hematopoietic transplants. In accordance with the use of embryonic-like stem cells as allogenic hematopoietic transplants, it may be preferable to treat the host to reduce immunological rejection of the donor cells, such as those described in U.S. Pat. No. 5,800,539, issued Sep. 1, 1998; and U.S. Pat. No. 5,806,529, issued Sep. 15, 1998, both of which are incorporated herein by reference.

For example, embryonic-like stem cells, the differentiation of which has been modulated according to the methods of the invention can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair. Likewise, hematopoietic progenitor cells, the differentiation of which has been modulated according to the methods of the invention, may be used instead of bone marrow or endothelial progenitor cells.

Stem cells, for example embryonic-like stem cells, the differentiation of which has been modulated according to the methods of the invention, can be used for augmentation, repair or replacement of cartilage, tendon, or ligaments. For example, in certain embodiments, prostheses (e.g., hip prostheses) are coated with replacement cartilage tissue constructs grown from embryonic-like stem cells of the invention. In other embodiments, joints (e.g. knee) are reconstructed with cartilage tissue constructs grown from embryonic-like stem cells. Cartilage tissue constructs can also be employed in major reconstructive surgery for different types of joints (for protocols, see e.g., Resnick, D., and Niwayama, G., eels., 1988, Diagnosis of Bone and Joint Disorders, 2d ed., W.B. Saunders Co.).

The stem cells and progenitor cells treated according to the methods of the invention can be used to repair damage of tissues and organs resulting from disease. In such an embodiment, a patient can be administered embryonic-like stem cells to regenerate or restore tissues or organs which have been damaged as a consequence of disease, e.g., enhance immune system following chemotherapy or radiation, repair heart tissue following myocardial infarction. Stem and/or progenitor cells treated according to the methods, and with the immunomodulatory compounds, of the invention, or administered in conjunction with the immunomodulatory compounds of the invention, may be transplanted into an individual in need thereof to repair and/or replace hepatic, pancreatic or cardiac tissue.

The stem cells and progenitor cells treated according to the methods of the invention can also be used to augment or replace bone marrow cells in bone marrow transplantation. Human autologous and allogenic bone marrow transplantation is currently used as a therapy for diseases such as leukemia, lymphoma and other life-threatening disorders. The drawback of these procedures, however, is that a large amount of donor bone marrow must be removed to insure that there is enough cells for engraftment.

The embryonic-like stem cells collected according to the methods of the invention can provide stem cells and progenitor cells that would reduce the need for large bone marrow donation. It would also be, according to the methods of the invention, to obtain a small marrow donation and then expand the number of stem cells and progenitor cells culturing and expanding in the placenta before infusion or transplantation into a recipient.

The large numbers of embryonic-like stem cells and/or progenitor obtained using the methods of the invention would, in certain embodiments, reduce the need for large bone marrow donations. Approximately $1\times10^8$ to $2\times10^8$ bone marrow mononuclear cells per kilogram of patient weight must be infused for engraftment in a bone marrow transplantation (i.e., about 70 ml of marrow for a 70 kg donor). To obtain 70 ml requires an intensive donation and significant loss of blood in the donation process. In a specific embodiment, cells from a small bone marrow donation (e.g., 7-10 ml) could be expanded by propagation, for example in a placental bioreactor, before infusion into a recipient. The stem cells, and progenitor cells, particularly CD34+ or CD133+ progenitor cells, the differentiation of which has been modulated according to the methods of the invention, can thus provide stem and/or progenitor cells that would reduce or eliminate the need for a large bond marrow donation.

The embryonic-like stem cells isolated from the placenta may be used, in specific embodiments, in autologous or heterologous enzyme replacement therapy to treat specific diseases or conditions, including, but not limited. to lysosomal storage diseases, such as Tay-Sachs, Niemarm-Pick, Fabry's, Gaucher's, Hunter's, Hurler's syndromes, as well as other gangliosidoses, mucopolysaccharidoses, and glycogenoses.

In other embodiments, the cells may be used as autologous or heterologous transgene carriers in gene therapy to correct inborn errors of metabolism such as adrenoleukodystrophy, cystic fibrosis, glycogen storage disease, hypothyroidism, sickle cell anemia, Pearson syndrome, Pompe's disease, phenylketonuria (PKU), and Tay-Sachs disease, porphyrias, maple syrup urine disease, homocystinuria, mucopolysaccharidenosis, chronic granulomatous disease, and tyrosinemia. or to treat cancer, tumors or other pathological conditions.

In other embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, scalp (hair) transplantation, or for reconstruction of other damaged or diseased organs or tissues.

Furthermore, a small number of stem cells and progenitor cells normally circulate in the blood stream. In another embodiment, such exogenous stem cells or exogenous progenitor cells are collected by apheresis, a procedure in which blood is withdrawn, one or more components are selectively removed, and the remainder of the blood is reinfused into the donor. The exogenous cells recovered by apheresis are expanded by the methods of the invention, thus eliminating the need for bone marrow donation entirely.

In another embodiment, expansion of hematopoietic progenitor cells in accordance with the methods of the invention is used as a supplemental treatment in addition to chemotherapy. Most chemotherapy agents used to target and destroy cancer cells act by killing all proliferating cells, i.e., cells going through cell division. Since bone marrow is one of the most actively proliferating tissues in the body, hematopoietic stem cells are frequently damaged or destroyed by chemotherapy agents and in consequence, blood cell production is diminishes or ceases. Chemotherapy must be terminated at intervals to allow the patient's hematopoietic system to replenish the blood cell supply before resuming chemotherapy. It may take a month or more for the formerly quiescent stem cells to proliferate and increase the white blood cell count to acceptable levels so that chemotherapy may resume (when again, the bone marrow stem cells are destroyed).

While the blood cells regenerate between chemotherapy treatments, however, the cancer has time to grow and possibly become more resistant to the chemotherapy drugs due to natural selection. Therefore, the longer chemotherapy is given and the shorter the duration between treatments, the greater the odds of successfully killing the cancer. To shorten the time between chemotherapy treatments, embryonic-like stem cells or progenitor cells differentiated in accordance with the methods of the invention could be introduced into the patient. Such treatment would reduce the time the patient would exhibit a low blood cell count, and would therefore permit earlier resumption of the chemotherapy treatment.

In another embodiment, the human placental stem cells can be used to treat or prevent genetic diseases such as chronic granulomatous disease.

5.6.3. Amelioration of Inflammation

The stem and progenitor cells, the differentiation of which has been modulated according to the methods of the invention, may be used as general anti-inflammatory agents. The inventors have discovered that stem and progenitor cells from, for example, cord blood, when transplanted into a patient, reduce or substantially eliminate the inflammatory response. Thus, in one embodiment, the methods of the invention comprise administering to a patient having an inflammatory response, or who is likely to develop an inflammatory response, stem cells or progenitor cells whose differentiation has been modulated by one or more of the compounds of the invention. In specific embodiments, the stem cells are embryonic-like stem cells, and the progenitor cells are hematopoietic stem cells, particularly $CD34^+$ or $CD133^+$ progenitor cells.

The inventors have also discovered that treatment of an individual with the compounds of the inventions, i.e., IMiDs, stimulates the development and differentiation of cells that modulate, ameliorate or reduce the inflammatory response. Thus, another embodiment of the invention comprises a method of treating an individual having an inflammatory response, or who is likely to develop an inflammatory response, comprising administering an effective dose of one or more of the compounds of the invention to said individual. In another embodiment, the method comprises contacting stem or progenitor cells with the compounds of the invention prior to administration to said individual, then administering a therapeutically effective dose of said cells to said individual. In yet another embodiment, cell so treated may be co-administered with one or more of the compounds of the invention to said individual in therapeutically-effective doses.

In other embodiments, inflammation may be reduced by administration of other compounds in combination with the compounds and/or cells of the invention. For example, such additional compounds may comprise steroids, such as prednisone, or any of the non-steroidal anti-inflammatory agents, such as the cox-1/cox-2 inhibitors acetylsalicylic acid (aspirin), ibuprofen, acetaminophen, cox-1-specific inhibitors, or derivatives of any of these compounds. Such additional anti-inflammatory agents may be delivered by any standard route, such as intravenously, topically, intradermally, or by inhalation, and may be delivered contemporaneously with the compounds and/or cell of the invention, or at different times.

The above methods may be used to treat any disease or condition associated with, caused by, or resulting in inflammation. For example, the methods may be used to treat inflammation caused by trauma such as accidental injury. The methods may also be used to treat inflammation caused by or injury that is associated with surgical procedures, in particular vessel-related surgical procedures such as grafts of natural tissue, synthetic vascular grafts, heart valves or angioplasties. The methods may also be used to prevent stenosis or restenosis. The methods above may also be used to treat inflammation resulting from any disease or condition, including but not limited to diseases or conditions such as heart disease, atherosclerosis, allergy or hypersensitivity, immune disorder, autoimmune disorder such as arthritis, or inflammations due to infections. In addition to treating a inflammatory condition that already exists, the cells and/or compounds of the invention may be administered to an individual prophylactically, so as to reduce the occurrence of inflammation. This is particularly useful as a form of pre-operative therapy, whereby reduction of the post-operative inflammatory response improves an individual's chances for a successful outcome and reduces hospital stay time and periods of disability.

Monitoring of the effectiveness of the anti-inflammatory effect of the above treatments may be accomplished by any known methods, such as visual inspection, MRI or CAT scans, determination of systemic or local temperature, etc. Because a protein known as C-reactive protein is a marker for inflammation, the effectiveness of the above treatment methods may be monitored by assaying for a reduction in the amount of C-reactive protein in an individual, particularly in the area formerly experiencing inflammation.

5.6.4. Production of Dendritic Cell and Granulocyte Cell Populations

The compounds of the invention may be administered specifically to modulate the differentiation of stem and/or progenitor cells along a granulocytic developmental pathway versus a dendritic cell developmental pathway. In a like manner, the cell of the invention may be modulated in vivo or ex vivo to produce expanded populations of dendritic cells or granulocytes.

Dendritic cells can be used as reagents for immune-based therapies. For example, dendritic cells can be co-cultured with T lymphocytes and protein antigen in vitro, thus driving the ex vivo antigen-specific activation of T cells. The activated T cells are then administered autologously to effect an antigen-specific immune response in vivo (WO 97/24438). In another example, T cells can be activated in vitro by contacting the T lymphocytes with dendritic cells that directly express an antigenic protein from a recombinant construct. The activated T cells can be used for autologous infusion (WO 97/29183).

T cells activated with specific peptides or protein fragments become immunizing agents against the proteins, cells or organisms from which the peptides or fragments were derived. For example, dendritic cells may be loaded with tumor-specific peptides. Specific application of DC-driven ex vivo T cell activation to the treatment of prostate cancer is described and claimed in U.S. Pat. No. 5,788,963. Mayordomo et al. demonstrated bone marrow-derived dendritic cells pulsed with synthetic tumor peptides elicit protective and therapeutic anti-tumor immunity (*Nature Medicine* 1:1297-1302 (1995); *J. Exp. Med.*, 183:1357-1365 (1996)). The U.S. Pat. No. 5,698,679 describes immunoglobulin fusion proteins that deliver antigenic peptides to targeted antigen presenting cells (APCs), including dendritic cells, in vivo. This same approach may be used with peptides or antigens derived from viruses, bacteria, or parasites to create viral, bacterial, or parasitic vaccines.

Dendritic cells are also targets for therapeutic intervention in the treatment of various immune-mediated disorders. For example, dendritic cells have been implicated as an important player in the pathogenesis and pathophysiology of AIDS (e.g., serve as reservoirs for the HIV virus). See Zoeteweij et al., *J. Biomed. Sci.* 5(4):253-259 (1998); Grouard et al., *Curr. Opin. Immunol.* 9(4):563-567 (1997); Weissman et al., *Clin. Microbiol. Rev.* 10(2):358-367 (1997). In vitro methods for screening pharmaceutical candidates for agents that abrogate HIV infection of DC are described in U.S. Pat. No. 5,627,025. In another example, dendritic cells can be manipulated to induce T cell unresponsiveness to donor tissue or organ in a recipient (see U.S. Pat. No. 6,375,950).

Granulocytes can be used in granulocyte transfusions in the treatment or prevention of infections, e.g., bacterial neonatal sepsis, neutropenia-associated infections in cancer patients, and potential infections in patients receiving bone-marrow transplants. Granulocytes can also be used in prevention or treatment of allergy. For example, granulocytes involved in IgE-mediated inflammation (i.e., granulocytes coated with IgE antibodies some of which having specificity for the allergen) can be inactivated and used to alleviate the symptoms of an already established immune response against the allergen (see U.S. Pat. No. 6,383,489).

Thus, in one embodiment of the invention, a population of granulocytes in an individual is expanded from the progenitor cells of the invention by a method comprising administering to said individual a therapeutically-effective amount of a compound of the invention, wherein said amount is sufficient to induce the production of a plurality of granulocytes from $CD34^+$ cells endogenous to said individual. In another embodiment, a population of granulocytes is expanded within an individual by a method comprising administering to said individual a population of $CD34^+$ or $CD133^+$ progenitor cells, wherein said cells have been contacted with a compound of the invention for at least three days, and administering said population of cells to said individual. In another embodiment, population of granulocytes is expanded within an individual by a method comprising administering to said individual a population of $CD34^+$ or $CD133^+$ progenitor cells and a compound of the invention, wherein the dose of said compound of the invention is sufficient to cause differentiation of a plurality of said population of cell into granulocytes. In a specific embodiment of the above embodiments, said $CD34^+$ progenitor cells are $CD34^+CD38^-CD33^+$ cells.

5.6.5. Treatment of Other Diseases and Conditions

The differentiated stem and progenitor cells of the invention, or the compounds of the invention, may also be used, alone or in combination, to treat or prevent a variety of other diseases or conditions. In certain embodiments, for example, the disease or disorder includes, but is not limited to, but not limited to a vascular or cardiovascular disease, atherosclerosis, diabetes, aplastic anemia, myelodysplasia, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis (ALS), ischemic renal disease, brain or spinal cord trauma, heart-lung bypass, glaucoma, retinal ischemia, retinal trauma, lysosomal storage diseases, such as Tay-Sachs, Niemann-Pick, Fabry's, Gaucher's, Hunter's, and Hurler's syndromes, as well as other gangliosidoses, mucopolysaccharidoses, glycogenoses, inborn errors of metabolism, adrenoleukodystrophy, cystic fibrosis, glycogen storage disease, hypothyroidism, sickle cell anemia, Pearson syndrome, Pompe's disease, phenylketonuria (PKU), porphyrias, maple syrup urine disease, homocystinuria, mucopolysaccharidosis, chronic granulomatous disease and tyrosinemia, Tay-Sachs disease, cancer, tumors or other pathological or neoplastic conditions.

In other embodiments, the cells of the invention (e.g., which have been exposed to the compounds of the invention) may be used in the treatment of any kind of injury due to trauma, particularly trauma involving inflammation. Examples of such trauma-related conditions include central nervous system (CNS) injuries, including injuries to the brain, spinal cord, or tissue surrounding the CNS injuries to the peripheral nervous system (PNS); or injuries to any other part of the body. Such trauma may be caused by accident, or may be a normal or abnormal outcome of a medical procedure such as surgery or angioplasty. The trauma may be related to a rupture or occlusion of a blood vessel, for example, in stroke or phlebitis. In specific embodiments, the cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

In a specific embodiment, the disease or disorder is aplastic anemia, myelodysplasia, leukemia, a bone marrow disorder or a hematopoietic disease or disorder. In another specific embodiment, the subject is a human.

5.7. Pharmaceutical Compositions

The present invention encompasses pharmaceutical compositions comprising a dose and/or doses of one or more of the compounds of the invention, wherein said dose or doses are effective upon single or multiple administration, prior to or following transplantation of conditioned or unconditioned human $CD34^+$ or $CD133^+$ progenitor or stem cells to an individual, exerting effect sufficient to inhibit, modulate and/or regulate the differentiation of these stem and/or progenitor cells into specific cell types, e.g., hematopoietic lineage cells, particularly myeloid lineage cells. In this context, as elsewhere in the context of this invention, "individual" means any individual to which the compounds or cells are administered, e.g., a mammal, bird or reptile.

Thus, in a specific embodiment, said dose or doses of the compounds of the invention, administered to an individual, modulate the differentiation of endogenous $CD34^+$ progenitor cells into dendritic cells. In a more specific embodiment, the dose or doses increase the number of granulocytic cells in said individual to which said dose or doses have been administered. In another more specific embodiment, the dose or doses increase the number of $CD34^+CD38^-CD33^+$ or $CD34^+CD38^-CD33^-$ progenitor cells in a mammal to which said dose or doses have been administered.

In other embodiments, $CD34^+$ or $CD133^+$ progenitor or stem cells of interest are transplanted into human subject or patient in need thereof. Subsequent to transplantation, a compound of the invention is administered to the human subject or patient, to modulate the differentiation of the transplanted cells of interest in vivo. In a specific embodiment, such cells are differentiated in vivo into granulocytes. In yet other embodiments, the differentiation of progenitor or stem cells of interest in a human subject or patient is modulated in situ by administration of a compound of the invention.

In yet another embodiment, the invention provides pharmaceutical compositions comprising isolated cord blood stem or progenitor cell populations that have been augmented with hematopoietic progenitor cells that have been differentiated by exposure to compounds that inhibit TNF-α activity, in accordance with the methods of the invention. In another embodiment, the invention provides pharmaceutical compositions comprising cord blood that is supplemented with stem or progenitor cells contacted with the compounds of the invention; in a specific embodiment, said stem or progenitor cells have been differentiated by said compounds.

In yet another embodiment, the invention provides for pharmaceutical compositions comprising both one or more of the immunomodulatory compounds of the invention, and the stem and/or progenitor cells of the invention. Such compositions may be prepared 1, 2, 3, 4, 5, 6, 7, 8, 9, 10, 11 or 12 days in advance of administration so as to modulate the differentiation of the stem and/or progenitor cells along different developmental/differentiation pathways.

In yet another embodiment, the pharmaceutical compositions of the present invention may comprise the stem or progenitor cells themselves, wherein said cells have been differentiated according to the methods disclosed herein. Thus, the present invention provides a pharmaceutical composition comprising a plurality of stem cells and/or progenitor cells, wherein said plurality of stem and/or progenitor cells has been contacted with one or more of the immunomodulatory compounds of the invention in a concentration and for a duration sufficient for said compound(s) to modulate differentiation of said cells.

Thus, the pharmaceutical compositions of the invention comprise the compounds of the invention, administered to an individual; the cells of the invention, administered to an individual, in combination with the compounds of the invention, separately administered; and the cells of the invention, contacted with the compounds of the invention, administered to said individual.

The invention provides methods of treatment and prevention of a disease or disorder by administration of a therapeutically effective amount of a compound or a composition of the invention to a mammalian, preferably human, subject, in order to effect modulation of the proliferation and/or differentiation of $CD34^+$ or $CD133^+$ progenitor cells or stem cells transplanted to, or residing within the subject. In one embodiment, the invention provides a method of modulating the differentiation of $CD34^+$ and $CD133^+$ progenitor or stem cells so as to increase within a mammal the number of granulocytic cells. In another embodiment, any cell lineage that may be derived from a $CD34^+$ and/or $CD133^+$ progenitor or stem cell may be modulated by administration of the compounds of the invention to a mammal, preferably to a human. The term "mammal" as used herein, encompasses any mammal. Preferably a mammal is in need of such treatment or prevention. Examples of mammals include, but are not limited to, cows, horses, sheep, pigs, cats, dogs, mice, rats, rabbits, guinea pigs, monkeys, etc., more preferably, a human.

Administration of compounds of the invention can be systemic or local. In most instances, administration to a mammal will result in systemic release of the compounds of the invention (i.e., into the bloodstream). Methods of administration include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, intraocular and intracameral injection and non-injection routes, such as intravaginal rectal., or nasal administration. Preferably, the compounds and compositions of the invention are administered orally. In specific embodiments, it may be desirable to administer one or more compounds of the invention locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds of the invention can be administered via typical as well as non-standard delivery systems, e.g., encapsulation in liposomes, microparticles, microcapsules, capsules, etc. For example, the compounds and compositions of the invention can be delivered in a vesicle, in particular a liposome (see Langer, 1990, Science 249:1527-1533; Treat et al., in Liposomes in *Therapy of Infectious Disease and Cancer*, Lopez-Berestein and Fidler (eds.), Liss, New York, pp. 353-365 (1989); Lopez-Berestein, ibid., pp. 317-327; see generally ibid.). In another example, the compounds and compositions of the invention can be delivered in a controlled release system. In one embodiment, a pump may be used (see Langer, supra; Sefton, 1987, *CRC Crit. Ref Biomed. Eng.* 14:201; Buchwald et al., 1980, *Surgery* 88:507 Saudek et al., 1989, *N. Engl. J. Med.* 3:574). In another example, polymeric materials can be used (see Medical Applications of Controlled Release, Langer and Wise (eds.), CRC Press., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, Ann. Neurol. 25:351; Howard et al., 1989, *J. Neurosurg.* 71:105). In still another example, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) can be used. When administered as a composition, a compound of the invention will be formulated with a suitable amount of a pharmaceutically acceptable vehicle or carrier so as to provide the form for proper administration to the mammal. The term "pharmaceutically acceptable" means approved by a regulatory agency of the Federal or a state government or listed in the U.S. Pharmacopeia or other generally recognized pharmacopeia for use in mammals, and more particularly in humans. The term "vehicle" refers to a diluent, adjuvant, excipient, or carrier with which a compound of the invention is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. Preferably, when administered to a mammal, the compounds and compositions of the invention and pharmaceutically acceptable vehicles, excipients, or diluents are sterile. An aqueous medium is a preferred vehicle when the compound of the invention is administered intravenously, such as water, saline solutions, and aqueous dextrose and glycerol solutions.

The present compounds and compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In a preferred embodiment, the compounds and compositions of the invention are formulated for administration in accordance with routine procedures as a pharmaceutical composition adapted for oral or intravenous administration to humans. In one embodiment, the pharmaceutically acceptable vehicle is a hard gelatin capsule. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference.

Compounds and compositions of the invention formulated for oral delivery, are preferably in the form of capsules, tablets, pills, or any compressed pharmaceutical form. Moreover, where in tablet or pill form, the compounds and compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound that swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles, excipients, and diluents, such as magnesium stearate, sodium saccharine, cellulose, magnesium carbonate, lactose, dextrose, sucrose, sorbitol, mannitol, starch, gum acacia, calcium silicate, microcrystalline cellulose, polyvinylpyrrolidone, water, syrup, and methyl cellulose, the formulations can additionally include lubricating agents, such as talc, magnesium stearate, mineral oil, wetting agents, emulsifying and suspending agents, preserving agents such as methyl- and propylhydroxybenzoates. Such vehicles are preferably of pharmaceutical grade. Orally administered compounds and compositions of the invention can optionally include one or more sweetening agents, such as fructose, aspartame or saccharin; one or more flavoring agents such as peppermint, oil of wintergreen, or cherry; or one or more coloring agents to provide a pharmaceutically palatable preparation.

A therapeutically effective dosage regimen for the treatment of a particular disorder or condition will depend on its nature and severity, and can be determined by standard clinical techniques according to the judgment of a medical practitioner. In addition, in vitro or in vivo assays can be used to help identify optimal dosages. Of course, the amount of a compound of the invention that constitutes a therapeutically effective dose also depends on the administration route. In general, suitable dosage ranges for oral administration are about 0.001 milligrams to about 20 milligrams of a compound of the invention per kilogram body weight per day, preferably, about 0.7 milligrams to about 6 milligrams, more preferably, about 1.5 milligrams to about 4.5 milligrams. In a preferred embodiment, a mammal, preferably, a human is orally administered about 0.01 mg to about 1000 mg of a compound of the invention per day, more preferably, about 0.1 mg to about 300 mg per day, or about 1 mg to about 250 mg in single or divided doses. The dosage amounts described herein refer to total amounts administered; that is, if more than one compound of the invention is administered, the preferred dosages correspond to the total amount of the compounds of the invention administered. Oral compositions preferably contain 10% to 95% of a compound of the invention by weight. Preferred unit oral-dosage forms include pills, tablets, and capsules, more preferably capsules. Typically such unit-dosage forms will contain about 0.01 mg, 0.1 mg, 1 mg, 5 mg, 10 mg, 15 mg, 20 mg, 50 mg, 100 mg, 250 mg, or 500 mg of a compound of the invention, preferably, from about 5 mg to about 200 mg of compound per unit dosage.

In another embodiment, the compounds and compositions of the invention can be administered parenterally (e.g., by intramuscular, intrathecal, intravenous, and intraarterial routes), preferably, intravenously. Typically, compounds and compositions of the invention for intravenous administration are solutions in sterile isotonic aqueous vehicles, such as water, saline, Ringer's solution, or dextrose solution. Where necessary, the compositions may also include a solubilizing agent. Compositions for intravenous administration may optionally include a local anesthetic such as lignocaine to ease pain at the site of the injection. For intravenous administration, the compounds and compositions of the invention can be supplied as a sterile, dry lyophilized powder or water-free concentrate in a hermetically sealed container, such as an ampule or sachette, the container indicating the quantity of active agent. Such a powder or concentrate is then diluted with an appropriate aqueous medium prior to intravenous administration. An ampule of sterile water, saline solution, or other appropriate aqueous medium can be provided with the powder or concentrate for dilution prior to administration. Or the compositions can be supplied in pre-mixed form, ready for administration. Where a compound or composition of the invention is to be administered by intravenous infusion, it can be dispensed, for example, with an infusion bottle containing sterile pharmaceutical-grade water, saline, or other suitable medium.

Rectal administration can be effected through the use of suppositories formulated from conventional carriers such as cocoa butter, modified vegetable oils, and other fatty bases. Suppositories can be formulated by well-known methods using well-known formulations, for example see *Remington: The Science and Practice of Pharmacy*, Alfonso R. Gennaro ed., Mack Publishing Co. Easton, Pa., 19th ed., 1995, pp. 1591-1597, incorporated herein by reference To formulate and administer topical dosage forms, well-known transdermal and intradermal delivery mediums such as lotions, creams, and ointments and transdermal delivery devices such as patches can be used (Ghosh, T. K.; Pfister, W. R.; Yum, S. I. *Transdermal and Topical Drug Delivery Systems*, Interpharm Press, Inc. p. 249-297, incorporated herein by reference). For example, a reservoir type patch design can comprise a backing film coated with an adhesive, and a reservoir compartment comprising a compound or composition of the invention, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the skin.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In one embodiment, the kit contains more than one compound of the invention. In another embodiment, the kit comprises a compound of the invention and another biologically active agent.

The compounds of the invention are preferably assayed in vitro and in viva, for the desired therapeutic or prophylactic activity, prior to use in humans. For example, in vitro assays can be used to determine whether administration of a specific compound of the invention or a combination of compounds of the invention is preferred. The compounds and compositions of the invention may also be demonstrated to be effective and safe using animal model systems. Other methods will be known to the skilled artisan and are within the scope of the invention.

5.8. Assays Using the Methods of the Invention

The methodology described above, i.e., the examination of the effect of IMiDs such as ACTIMID™ on the differentiation on early progenitor cells, such as CD34+ cells, can be applied to any compound of interest, the effect of which on differentiation is desired to be known. This may be accomplished in several ways.

In one embodiment, the compound may simply substitute for ACTIMID™ or any of the other compounds of the invention. Here, CD34+ progenitor cells and/or CD133+ progenitor cells may be contacted with the compound of interest, at varying concentrations, under conditions that allow for the proliferation and/or differentiation of the progenitor cells into committed and/or fully-differentiated cells. The culture methods disclosed herein, particularly the culture methods disclosed in Section 5.4, may be used. The effect, if any, of the compound of interest is determined by assessing the change, if any, in the cell populations that differentiate from the progenitor cells, where the change may be monitored by any phenotypic change, but is preferably assessed by determining cell surface markers that are present or absent. Like the methods of the invention, the compound of interest may be administered in a single dose at any time from initial culture to achievement of the finally-differentiated cell(s). Alternatively, the compound of interest may be administered in multiple doses during the proliferative stage, the differentiation stage, or both. The change in phenotypic characteristics of the proliferating/differentiating progenitor cells is preferably compared to a control culture of cells, such as DMSO-treated cells. Of particular interest would be any effects on proliferation or differentiation such as, but not limited to: modulation of the rate of proliferation; modulation of the rate of differentiation; modulation of differentiation of the progenitor cells into specific committed precursor cells; blocking the differentiation into particular cell types; and enhancing the differentiation into particular cell types.

In another embodiment, culturing, proliferation and differentiation takes place as above, but the compound of interest is contacted with the progenitor cell(s) along with ACTIMID™. In this manner, the effects, possibly synergistic, of multiple compounds may be determined. Of particular interest would be any compounds that have no, or a slight, effect on proliferation or differentiation alone, but have a significant effect in combination with ACTIMID™. In another embodiment, any two compounds of interest may be contacted with the progenitor cells under culture conditions, as above, that normally allow for the proliferation and differentiation of the progenitor cells. Here, preferably an experiment in which precursor cells are contacted with two compounds of interest contains a control in which the progenitor cells are contacted with only one of each of said compounds; a control in which the cells are contacted with ACTIMID™; and a control in which cells are not contacted with a compound, or are contacted with DMSO. Again, the variations in the dosages, and timing of dosing, are as described above and in Section 5.4.

6. WORKING EXAMPLES

6.1. Example 1

Effects of Thalidomide, ACTIMID™ and REVIMID™ on Differentiation of CD34+ Progenitor Cells In the following example, the effects of Thalidomide (Thal), ACTIMID™ ("ACTIMID™") and REVIMID™ on the differentiation of CD34+(hematopoietic progenitor) cells and the generation of colony forming units (CFU) were studied. Significantly, the results demonstrate that ACTIMID™ and REVIMID™ can be used to suppress specifically the generation of erythropoietic colonies (BFU-E and CFU-E), while augmenting both the generation of leukocyte and platelet forming colonies (CFU-GM) and enhancing total colony forming unit (CFU-Total) production.

The methods of the invention can therefore be used to regulate the differentiation of stem cells, and can also be used to stimulate the rate of colony formation, providing significant benefits to hematopoietic stem cell transplantation by improving the speed of bone marrow engraftment and recovery of leukocyte and/or platelet production.

Cord blood CD34+ hematopoietic progenitor cells were plated in 96 well cultivation dishes at a density of 1000 cells per well in IMDM supplemented with 20% fetal calf serum and cytokines (IL-3, G-CSF and kit-ligand (R&D Systems, Inc.) The cells were exposed to Thalidomide (Thal), ACTIMID™ and REVIMID™, or DMSO (a control compound), and allowed to culture for 6 days. Cord blood CD34+ cells were plated in 96 well cultivation dishes at a density of 1000 cells per well in IMDM supplemented with 20% fetal calf serum and cytokines (IL-3, GCSF and kit-ligand (KL) (R&D Systems, Inc.)) After culturing, cells were stained and sorted with a fluorescence activated. cell sorter (FACS). 400 µL of stained cells were harvested and diluted to 1.0 ml with 1% fetal calf serum in phosphate buffered saline (PBS). Cells were counted to determine the effect of modulation of stem cell differentiation. The cell counts obtained are shown in FIG. 1.

These results demonstrate that the compounds of the invention are effective in the modulation of the lineage commitment of hematopoietic progenitor stem cells. Thus, ACTIMID™ and REVIMID™ can be used to suppress specifically the generation of red blood cells or erythropoietic colonies (BFU-E and CFU-E), while augmenting both the generation of leukocyte and platelet forming colonies (CFU-GM) and enhancing total colony forming unit production. The methods of the invention can therefore be used to regulate the differentiation of stem cells, and can also be used to stimulate the rate of specific colony formation, providing significant benefits to hematopoietic stem cell transplantation by improving the speed of bone marrow engraftment and recovery of leukocyte and/or platelet production by origin stem cell commitment toward desired engraftable lineages. Inhibition of erythropoiesis and expansion of CD34+CD38− progenitor populations by ACTIMID™ and REVIMID™ are further represented in FIG. 2.

6.2. Example 2

Effects of Thalidomide, ACTIMID™ and REVIMID™ on Proliferation and Differentiation of Human Cord Blood CD34+ Cells In the following example, the effects of Thalidomide, ACTIMID™ and REVIMID™ on the proliferation and differentiation of cord blood (CB) mononuclear cells into CD34+ (hematopoietic progenitor) cells were studied. Cord blood mononuclear cells are a mixed population of cells including a small population of hematopoietic progenitor (CD34+) cells. A subset of this small CD34+ cell population includes a population (approximately 1% of total CB mononuclear cells) of CD34+CD38+ cells and an even smaller population (less than 1% of total CB mononuclear cells) of CD34+CD38− cells. Significantly, the results demonstrate that ACTIMID™ causes an up-regulation (increased differentiation) of CD34+ cells, and that ACTIMID™ and REVIMID™ can apparently inhibit or slow down the differentiation of hematopoietic stem cells or progenitor cells compared with the positive and negative controls (FIGS. 3-7).

6.2.1. Materials and Methods

CB CD34+ cells were initiated at $4 \times 10^4$ cells/ml in a 24-well plate in 20% FCS IMDM (fetal calf serum/Iscove's Modified Dulbecco's Medium) supplemented with cytokines (1 L3, GCSF and Kit-ligand) (R&D Systems, Inc.). Thalidomide (Thal), ACTIMID™ or REVIMID™ were included in the culture at three different concentrations: 5 µg/ml, 1 µg/ml and 0.3 µg/ml. The same volumes of DMSO were used as controls. A negative control without, any compound was also used (indicated by "none" in FIGS. 3-7). Cells were cultured at 37° C. and 5% $CO_2$ in a humidified incubator for 7 days. Cells were then harvested from each well.

The total cell number from each well was determined by counting in a CELL-DYN® 1700 (Abbott Diagnostics) and the expression of CXCR4, CD45, CD34, CD38, CD 1 lb and Gly-A expression was analyzed by FACS (fluorescence-activated cell sorting) staining (FIGS. 3-7).

CB cells from two different donors (CB2276 and CB2417) were cultured, assayed and analyzed separately (Table 1).

6.2.2. Results and Discussion

The effects of Thalidomide, ACTIMID™ or REVIMID™ on cytokine-stimulated expansion of CD34+ cells was tested. As shown in FIG. 4, Thalidomide, ACTIMID™ and REVIMID™ do not have a significant effect on the proliferation of CD34+ cells that are cultured in the presence of IL-3, Kit-ligand (KL) and G-CSF when compared with the negative control ("none"). However, Thalidomide, ACTIMID™ and REVIMID™ appear to induce a yield of a slightly higher number of cells, when compared with the DMSO control. Considering that DMSO generally has a negative effect on cell proliferation in these experiments, these results suggest that Thalidomide, ACTIMID™ and REVIMID™ compounds may have a stimulatory effect on the proliferation of CD34+ cells that are cultured in the presence of IL-3, KL and G-CSF, since the same amount of DMSO is used as a carrier. In this respect, ACTIMID™ and REVIMID™ have a greater effect than does Thalidomide.

The effects of Thalidomide, ACTIMID™ and REVIMID™ on expression of cell differentiation were analyzed by FACS analysis of surface proteins CXCR4 and CD34 (FIGS. 3 and 4). ACTIMID™ and REVIMID™, but not Thalidomide, showed an inhibitory effect upon the expression of CXCR4. ACTIMID™ had a more potent effect than REVIMID™.

With respect to surface protein CD34+, ACTIMID™ caused up-regulation (increased proliferation) of CD34+ cells in both the CB2276 and CB2417 cultures. Thalidomide and REVIMID™, however, exhibited a similar effect in one donor but not in the other donor. Interestingly, in both ACTIMID™ and REVIMID™ treated cells, the majority of CD34+ and CD34− cells are CD38−, while cells in the control, DMSO-treated, and Thalidomide-treated populations are mainly CD38+. This indicates that ACTIMID™ and REVIMID™ can be used to suppress specifically the generation of red blood cells or erythropoietic colonies (BFU-E and CFU-E), while augmenting both the generation of leukocyte and platelet forming colonies (CFU-GM) and enhancing total colony forming unit production. The methods of the invention can therefore be used to regulate the differentiation of stem cells, and can also be used to stimulate the rate of colony formation, providing significant benefits to hematopoietic stem cell transplantation by improving the speed of bone marrow engraftment and recovery of leukocyte; and/or platelet production. See Table 4 below.

The effects of Thalidomide, ACTIMID™ and REVIMID™ on expression of cell differentiation was analyzed by FACS analysis of surface proteins of cells that were CD34+CD38− versus CD34+CD38+ or that were CD11b+. Results are set forth in Table 1.

TABLE 1

Examples of Effects on Cell Differentiation and Cell Surface Marker Expression of CD34, CD38 and CD11b in Cord Blood-Derived Hematopoietic Progenitor Cells

| CD34+CD38−/CD34+CD38+ Cell Population | | | | | |
|---|---|---|---|---|---|
| CB2276 | None. | DMSO | Thal | ACTIMID ™ | REVIMID ™ |
| 5 µg/ml | 1.2/6.3 | 2.7/3.7 | 3.5/6.5 | 17.3/0.2 | 4.0/0.3 |
| 1 µg/ml | 1.5/8.5 | 2.6/5.3 | 1.0/3.8 | 15.0/0.2 | 10.3/1 |
| 0.3 µg/ml | ND | 1.5/5.7 | 3.2/15.1 | 5.9/0.2 | 9.8/1.7 |
| CB2417 | None | DMSO | Thal | ACTIMID ™ | REVIMID ™ |
| 5 µg/ml | 0.5/5.7 | 0.8/5.2 | 1.1/3.0 | 14.7/0.1 | 4.2/0.3 |
| 1 µg/ml | 0.5/4.9 | 0.7/3.9 | 1.0/3.8 | 12.0/0.8 | 3.8/0.6 |
| 0.3 µg/ml | ND | 0.5/4.4 | 0.8/5.0 | 5.9/0.2 | 3.4/0.9 |
| CD11b+ Cell Population | | | | | |
|  | None | DMSO | Thal | ACTIMID ™ | REVIMID ™ |
| CB2276 | | | | | |
| 5 µg/ml | 11.7% | 5.0% | 8.1% | 1.6% | 4.8% |
| 1 µg/ml | 9.1% | 7.3% | 6.2% | 3.8% | 8.6% |
| 0.3 µg/ml | ND | 7.0% | 7.6% | 6.9% | 13.3% |
| CB2417 | | | | | |
| 5 µg/ml | 12.0% | 7.2% | 6.5% | 2.5% | 5.5% |
| 1 µg/ml | 7.2% | 5.3% | 5.2% | 3.9% | 8.2% |
| 0.3 µg/ml | ND | 5.1% | 7.8% | 8.4% | 11.2% |

There was no significant change in the size of the CD11b+ cell population, and in the case of REVIMID™, a larger CD11b+ cell population was observed at lower concentrations.

However, the level of CD 11b expression was decreased in both ACTIMID™- and REVIMID™-treated cells, as determined by mean immunofluorescence (MIF), indicating CD 11 b expression was repressed. This suggests that the CD11b+ cells are at a less differentiated state when cultured in the presence of ACTIMID™ and REVIMID™.

6.3. Example 3

Effects of ACTIMID™ and REVIMID™ on Human Cord Blood MNC Cells

In the previous examples, ACTIMID™ and REVIMID™ were shown to significantly down-regulate the expression of CXCR4 in cord blood CD34+ cells and to increase the CD34+ CD38− cell population. In this example, ACTIMID™ and REVIMID™ are shown to have similar activities on cord blood mononucleated cells (MNC).

6.3.1. Materials and Methods

Cord blood MNCs that had been cryopreserved and thawed using standard methods were isolated by standard Ficoll separation method and cultured in 24 well-plate at $0.5 \times 10^6$ cells/ml in 20% FCS-IMDM with cytokines (1L6, KL and G-CSF 10 ng/ml each) in triplicates. The experimental groups were None (cytokines only), DMSO (1.7 µl), ACTIMID™ (5.0 µg in 1.7 µl DMSO), REVIMID™ (5 µg in 1.7 µl DMSO). The cultured cells were harvested and analyzed by FACS staining after 1 week of culture. The results are summarized in Table 2 and in FIGS. 8-12. The data are expressed as an average +/− SD from three independent wells.

TABLE 2

|  | None | DMSO | ACTIMID ™ | REVIMID ™ |
|---|---|---|---|---|
| Total cells (1 × 10⁶) | 0.50 +/− 0.10 | 0.30 +/− 0.17 | 0.223 +/− 0.06 | 0.30 +/− 0 |
| CD34(%) | 2.50 +/− 0.33 | 2.73 +/− 0.07 | 3.31 +/− 0.64 | 2.34 +/− 0.22 |
| Total CD34+ cells | 7933 +/− 7310 | 8133 +/− 4623 | 7800 +/− 2600 | 7166 +/− 802 |
| CD34+CD38−(%) | 0.05 +1− 0.01 | 0.06 +/− 0.04 | 1.70 +/− 0.22 | 0.80 +/− 0.29 |
| CXCR4+CD45+(%) | 8.7 +/− 0.54 | 12.1 +/− 1.30 | 2.9 +/− 0.5 | 3.6 +/− 0.9 |
| CXCR4+CD45−(%) | 0.48 +/− 0.15 | 0.66 +/− 0.04 | 4.27 +/− 0.23 | 3.28 +/− 0.89 |

6.3.2. Results and Discussion

As shown in Table 2 and in FIGS. 8-12, the total cell numbers of MNCs cultured with DMSO, ACTIMID™ or REVIMID™ were lower than in the control group ("None," cytokines only). This may have resulted from the effects of DMSO. Cell cultures that were cultured with MID 1 exhibited a higher percentage of CD34+ cells than all the other groups, while the total numbers of CD34+ cells were similar in all groups. Numbers of CD34+CD38− cells were significantly higher in IMJD1 and REVIMID™ treated cells, which is consistent with the results of treating purified CD34+ cells with the compounds. It is well accepted that CD34+CD38− cells are a less differentiated hematopoietic progenitor cell which engrafts and proliferates after transplantation at a higher efficiency than CD34+CD38+ cells (Dao et al. 1998, Blood 91 (4): 1243-55; Huang et al., 1994, Blood 83(6): 1515-26).

DMSO appears to stimulate CXCR4 expression in cord blood MNCs. ACTIMID™ and REVIMID™ significantly inhibited the expression of CXCR4 expression on CD45+ cells when compared with both control groups.

A majority of CXCR4+ cells in the cultures of ACTIMID™- and REVIMID™-treated cells were CD45 negative. This cell population was significantly higher in the ACTIMID™- and REVIMID™-treated cells.

The results indicate that ACTIMID™ and REVIMID™ are useful in conditioning stem cells to counteract the deleterious effects of cryopreservation, thawing and/or exposure to cryopreservatives on stem cells. The results further indicate that the suppression by DMSO of CD34+ and CD 14+ cell production can counteracted by treating with ACTIMID™ or REVIMID™, which enhances that proliferative capacity of CD34+ and CD14+ cells.

6.4. Example 4

Effects of Thalidomide, ACTIMID™ and REVIMID™ on Monocyte Production 6.4.1. Materials and Methods Purified human cord blood CD34+ cells (greater than 90% CD34+) were cultured in 20% FCS IMDM medium supplemented with cytokines (IL3, IL6, G-CSF, KL and Epo) at $4\times10^4$ cells/ml for 14 days at 37° C. in a humidified 5% $CO_2$ incubator. The experimental groups consisted of a group in which (i) no DMSO or chemical compounds were added ("None"), (ii) DMSO only, (iii) Thalidomide dissolved in DMSO, (iv) ACTIMID™ dissolved in DMSO, and (v) REVIMID™ dissolved in DMSO. Aliquots of cells were harvested and stained with CD34-PE conjugated monoclonal antibody and CD14-FITC conjugated monoclonal antibody.

6.4.2. Results and Discussion

The results showed that in the "None" group, only 0.95% of the total cells were CD34+. In DMSO-treated group, only 0.17% of cells were CD34+, suggesting that DMSO has a negative effect on CD34+ expansion and preservation. In the Thalidomide-treated group, 0.24% of cells were CD34+, which is not significantly different from DMSO-treated cells. In the ACTIMID™- and REVIMID™-treated groups, however, there was a significantly higher percentage of CD34+ cells (18.7% and 7.1%, respectively). (See also experimental results depicted in FIG. 13 and accompanying figure legend).

CD14 is a marker for monocytes. In the "None" group, 11.5% of cells were CD14+, while in the DMSO-treated group, 3.7% were $CD14^+$, indicating that the production of monocytes decreased. As was the case for CD34 expression above, the results for the Thalidomide-treated group and the DMSO-treated group were similar. Since the ACTIMID™- and REVIMID™-treated groups were exposed to DMSO as well, it can be deduced that the monocyte production that is inhibited-by DMSO is overcome by treatment with ACTIMID™ or REVIMID™.

6.5. Example 5

Effects of ACTIMID™ Pretreatment on Transplanted Nucleated Cells from Umbilical Cord Blood and Placenta This experiment demonstrates that ACTIMID™ pre-treatment increases the survival of transplanted placental nucleated cells (PLNC), umbilical cord blood nucleated cells (UCBNC) and bone marrow cells (BMNC).

6.5.1. Materials and Methods

Placental nucleated cells (PLNC), umbilical cord blood nucleated cells (UCBNC) and bone marrow cells (BMNC) were obtained from human donors. PLNC and UCBNC were obtained from placenta and umbilical cord using methods described in Section 5.4 above.

The cells were pretreated by incubation in DMEM supplemented with 2% human CB serum with 10 g/ml ACTIMID™ for 24 hours. Cells were then washed, resuspended in autologous plasma, and administered intravenously to recipient adult SJL/L mice (Jackson Laboratories) that had bone marrow ablation produced by lethal irradiation (900cGy) according to standard methods. Such irradiation is better than 90% lethal by 50 days post-irradiation (Ende et al., 2001, Life Sciences 69(13):1531-1539; Chen and Ende, 2000, J. Med. 31: 21-30; Ende et al., 2000, Life Sci. 67(1):53-9; Ende and Chen, 2000, Am. J. Clin. Pathol. 114: 89).

6.5.2. Results and Discussion

The effects of ACTIMID™ pretreatment on the transplanted PLNC, UCBNC and BMNC are shown in Table 3 below. As can be seen in Table 3, ACTIMID™ pre-treatment increases the survival of transplanted placental nucleated cells (PLNC), umbilical cord blood nucleated cells (UCBNC) and bone marrow cells (BMNC).

TABLE 3

| Experimental Group | Treatment | # of Animals Irradiated | # of Animals Dead at 50 days | % Starting Body Weight at 50 days |
|---|---|---|---|---|
| 1 | PLNC $5 \times 10^6$ intravenous | 3 | 1 | 84 |
| 2 | PLNC $50 \times 10^6$ intravenous | 3 | 0 | 89 |
| 3 | PLNC $5 \times 10^6$ + ACTIMID ™ pre-treatment intravenous | 4 | 0 | 102 |
| 4 | UCBNC $100 \times 10^6$ intravenous | 3 | 0 | 81 |
| 5 | UCBNC $10 \times 10^6$ + ACTIMID ™ pre-treatment intravenous | 3 | 0 | 84 |
| 6 | UCBNC $10 \times 10^6$ intravenous |  | 1 | 78 |
| 7 | BMNC $0.5 \times 10^6$ | 3 | 3 | 79 |
| 8 | BMNC $5 \times 10^6$ | 3 | 3 | 74 |
| 9 | BMNC $50 \times 10^6$ | 3 | 2 | 83 |
| 10 | Control | 12 | 11 | N/A |

Abbreviations:
PLNC: placental nucleated cells
UCBNC: umbilical cord blood nucleated cells
BMNC: bone marrow cells
N/A: not applicable

6.6. Example 6

Modulation of Differentiation of CD34$^+$ Progenitor Cells

6.6.1. Materials and Methods

Bone marrow and cord blood CD34$^+$ progenitor cells were obtained from Clonetics and cultured in Iscove's MDM with BIT 95000 (StemCell Technologies) in the presence of SCF, Flt-3L, GM-CSF and TNF-α for 6 days, and then in the presence of GM-CSF and TNF-α for 6 additional days.

Analysis of cell surface phenotype: Cells were processed for double staining (30 min at 4° C.) at day 6 and day 12 using FITC and PE conjugated mAbs. Antibodies used were from BD Pharmingen: CD34 (PE), CD38 (FITC), CD33 (FITC), CD1a (FITC), CD86 (PE), CD14 (PE), CD83 (PE), CD54 (PE), CD11b (PE), CD11c (PE), HLA-DR (PE), CD15 (FITC), and CD133 (PE) from Miltenyi. Fluorescence analysis was performed on a FACScan flow cytometer after acquisition of 10,000 events (Coulter). Results presented are representative of four independent experiments.

Detection of apoptosis: Phosphatidyl serine exposure was determined using Annexin V-FITC staining in combination with propidium iodide (BD Pharmingen apoptosis detection kit I) following manufacturer instruction.

Phagocytosis: The endocytic activity of the cells was analyzed by measuring FITC-dextran uptake. Cells were incubated with 1 mg/ml dextran-FITC (Sigma) in complete medium at 37° C. for 1 hour and 4° C. for 1 hour as a negative control. Results presented are representative of two independent experiments.

T cell proliferation assay: After 13 days of culture, CD34$^+$-derived DC cells were collected, and after treatment with mitomycin C (50 μg/ml, Sigma), used as stimulators cells for allogenic adult CD3$^+$ T cells purified from peripheral blood mononuclear cells (PBMCs) from healthy volunteers. CD3$^+$ T responder cells were used at a concentration of $5 \times 10^4$ cells/well. Stimulators cells were added in graded doses to the T cells in black 96-well flat bottom, clear bottom tissue culture plates for chemiluminescence detection. Cultures were performed in RPMI 1640 medium supplemented with 10% heat-inactivated FBS, glutamine and Penicillin-streptomycin. After 6 days of culture, cell proliferation was measured with the BrdU chemiluminescence assay (Roche, Nutley N.J.), following manufacturer instructions. Results are presented as the mean±SD obtained from triplicate cultures.

6.6.2. Results and Discussion

ACTIMID™ was found to significantly alter the development of DC from CD34$^+$ progenitors. To study the effect of ACTIMID™ on the generation of DC, CD34$^+$ progenitors cells were cultured with or without ACTIMID™ (1 μM) for a period of 12 days during the expansion and maturation phase (day 1 to day 12), or a period of 6 days during the maturation phase (day 6 to day 12) (FIG. 14). The addition of ACTIMID™ from day 1 to day 12 inhibited the acquisition of the DC phenotype (FIG. 15) and more importantly increased the CD34$^+$ CD38$^-$ population, altering the normal differentiation of CD34$^+$ CD38$^-$ cells into CD34$^+$CD38$^+$ cells (FIG. 16). However, ACTIMID™ treated CD34$^+$ cells did acquire the CD33 myeloid marker, and these cells presented a CD34$^+$ CD38$^-$CD33$^+$ phenotype at day 6. ACTIMID™ almost completely prevented the generation of CD1a$^+$ cells at day 6, and particularly the generation of double positive CD86$^+$CD1a$^+$ cells. This double positive population is thought to be the precursor of epidermal Langerhans DC. ACTIMID™ also decreased the generation of CD14$^+$CD1a$^-$ cells that can give rise both to dermal DC and monocyte/macrophages. The increase in the early progenitor population (CD34$^+$CD38$^-$ cells) and the block in the myeloid DC progenitors (CD1a$^+$CD14$^-$ and CD1a$^-$CD14$^+$ cells) were dose dependant and reached a maximum at 1 μM of ACTIMID™ (FIG. 17). This effect was reversible and interference with the CD34 differentiation pathway was only observed if CD34$^+$ progenitors were cultured for at least 3 days with ACTIMID™ (FIG. 18).

Multiple doses of ACTIMID™ between days 0 and 6 intensified the increase in the CD34$^+$ population (FIG. 19A).

CD34$^+$ progenitor cells cultured in the presence of ACTIMID™ also displayed at day 12 a decreased expression of co-stimulatory molecules (CD86, CD80) (FIG. 20). The CD54 adhesion molecule was altered with decreased expression of the CD54$^{bright}$ and increased expression of the CD54$^{dim}$ populations (FIG. 21). The expression of HLA-DR molecules was reduced in ACTIMID™ treated CD34$^+$ progenitors.

When ACTIMID™ was added at day 6, after culture from days 0-6 without treatment, and when the CD1a$^+$ population had already been generated, ACTIMID™ increased the persistence of the CD1a$^+$ population (Table 1). The ACTIMID™-treated culture contained relatively more CD1a$^+$ precursors at day 12 than the DMSO control. The addition of ACTIMID™ to day 6 CD34$^+$ differentiated cells also decreased considerably the generation of CD14$^+$ precursors and the expression of the co-stimulatory molecules (CD86, CD80).

TABLE 1

Phenotypic characterization at day 12 of DC generated from CD34+ progenitor cells in the presence of ACTIMID ™ from day 6 to day 12

| Day 12 | DMSO day 6 to day 12 | ACTIMID ™ day 6 to day 12 |
|---|---|---|
| CD1a+ | 8.5% | 11.5% |
| CD14+ | 19.0% | 8.0% |
| CD86+ | 28.8% | 18.5% |
| CD80+ | 19.6% | 13.8% |

ACTIMID™ promotes granulocytic differentiation: To determine if the block in DC generation was associated with a change to a different myeloid differentiation pathway, we monitored the expression of the CD15 granulocytic marker. Expression of the CD15 surface molecule was increased in CD34$^+$ progenitor cells cultured in the presence of ACTIMID™ (FIG. 22). In the presence of a cytokine cocktail that drives DC differentiation, the addition of ACTIMID™ diverted the expansion/maturation of progenitor cells into a more granulocyte-like phenotype. We also studied the skew in myeloid differentiation by monitoring the expression of 2 markers: CD11c, expressed by myeloid DC progenitors for Langerhans cells and interstitial DC, and CD15 expressed by granulocyte progenitors. A decrease in the CD11c+CD15− population was associated with a concomitant increase in the CD11c−CD15$^+$ granulocytic population (FIG. 19B). Interestingly, multiples doses of ACTIMID™ enhanced the shift towards the granulocytic lineage.

Block in DC generation is not mediated by specific killing of the DC progenitors: To determine if the decrease in DC progenitors was mediated by specific killing, CD34$^+$ progenitor cells were cultured for a period of 6 days in the presence of SCF, Flt-3L, GM-CSF and TNF-α. At day 6, CD1a$^+$CD14$^-$ and CD1a$^-$CD14$^-$ cells (DC progenitors) were isolated by magnetic cell sorting (Miltenyi). Purified populations were cultured for an additional 2 days in the presence of GM-CSF and TNF-α with or without ACTIMID™ (1 μM). There was no significant increase in the level of annexin $V^+$-$PI^-$ (early apoptosis) and annexin $V^+$-$PI^+$ (late apoptosis) populations upon V™ treatment (FIG. 23).

Functional activity of DC generated from $CD34^+$ progenitors is altered: The phagocytic capacity of cells derived from $CD34^+$ progenitors cells cultured with cytokines with or without ACTIMID™ was assayed by the mannose receptor-mediated endocytosis of dextran-FITC at day 12. When ACTIMID™ was added from day 1 to day 12, there was a strong decrease in the phagocytic capacity compared to DMSO control (FIG. 24). When ACTIMID™ was added from day 6 to day 12 the phagocytic capacity was comparable to the DMSO-control cells (FIG. 25).

The antigen presentation capacity (APC) of $CD34^+$ cells cultured with cytokine with or without ACTIMID™ was evaluated by measuring their capacity to induce the proliferation of $CD3^+$ allogenic T cells in a Mixed Leucocyte Reaction (MLR) assay at day 12. When ACTIMID™ was added from day 1 to day 12, the $CD34^+$ cells showed a reduced capacity to stimulate the proliferation of T-cells as compared to DMSO control (FIG. 26). In contrast, when ACTIMID™ was added from day 6 to day 12, the capacity to stimulate the proliferation of T-cells was comparable to the DMSO-control cells (FIG. 27). The normal differentiation pathway followed by $CD34^+$ cells is depicted in FIG. 28.

These results indicate that ACTIMID™ dramatically attenuated the differentiation of $CD34^+$ progenitor cells into dendritic cells. As a consequence, ACTIMID™ treated cells presented a low phagocytic capacity and a reduced APC capacity. More importantly, ACTIMID™ increased early hematopoietic progenitors, the $CD34^+CD38^-$ cells. Those early hematopoietic progenitors have been shown to give better engraftment and repopulation in the NOD-SCID mouse model (Tamaki et al., J. Neurosci. Res. 69(6):976-86 (2002)). Moreover, ACTIMID™ skewed $CD34^+$ cells differentiation by switching myeloid differentiation toward the granulocytic lineage, even when the cytokine pressure is in favor of dendritic cell differentiation. In addition, ACTIMID™ was found to have no toxic effects on $CD34^+$ cells, and not to impair the cells' ability to proliferate. This modulation of DC function and promotion of granulocytic differentiation can have significant therapeutic utility for the treatment of various cancers, immunological disorders, and infectious diseases, and in organ transplants, and regenerative medicine.

See FIG. 29 for a graphical summary of the above.

6.7. Example 7

ACTIMID™ Modulates Differentiation of $CD133^+$ Progenitor Cells

Multiple doses of ACTIMID™, in addition to intensifying the increase in the $CD34^+$ population, also increases the expression of CD133, which is usually expressed by $CD34^{bright}$ hematopoietic progenitor cells and some primitive $CD34^-$ subpopulations (FIGS. 19A, 19B). ACTIMID™, by enriching for the $CD34^+$ $CD133^+$ primitive hematopoietic cells, should have clinical implication for hematopoietic recovery after stem cell transplantation. In addition, $CD133^+$ stem cells can also give rise to the endothelial lineage and contribute in term to wound healing. Multiple doses of ACTIMID™ did not exacerbate the block in the generation of Langerhans DC precursors.

6.8. Example 8

Generation of Murine Dendritic cells from Bone Marrow (BM) $Sca^+$ Hematopoietic Progenitor Cells

6.8.1. Materials and Methods

Mouse bone marrow from inbred C57BL/6 mice was obtained from Clonetics. Hematopoietic Sca+Lin− progenitors were enriched using SpinSep murine progenitor enrichment cocktail (StemCell Technologies) and cultured in Iscove's MDM with BIT 95000 (StemCell Technologies) in the presence of murine growth factors SCF, Flt3L, GM-CSF and M-CSF for 9 days, to promote expansion of Sca+ cells and a DC precursor phenotype and then in the presence of GM-CSF and TNF-α for 3 additional days to drive the cells to an immature DC phenotype. See FIG. 30. Enriched Sca+Lin− cells were cultured in the presence of DMSO (0.1%), ACTIMID™ at 10 μM or all-trans retinoic acid (ATRA) (ICN Biomedicals) at 10 μM from day 0. Compounds were added to cells at day 0 and day 9.

Analysis of Murine cell surface phenotype: Murine cells were processed for double staining (14 min at RT) at day 9 and day 12; using FITC and PE conjugated mAbs. Antibodies used were from BD Pharmingen: Sca (PE), CD11b (FITC), Gr-1 (FITC), CD86 (PE), CD14 (PE), CD80 (PE), I-$A^b$ (PE), CD40 (PE) and CD32.1/16.1 (FITC) from Miltenyi. Fluorescence analysis was performed on a FACScan flow cytometer (Coulter) after acquisition of 10,000 events.

6.8.2. Results and Discussion

ACTIMID™ was found to alter the development of Murine DC from $Sca^+$ progenitors. At day 9 cells presented a DC precursor phenotype with high surface expression of dendritic/myeloid markers CD32/16 (Fc receptors), CD11b, CD80, low expression of I-$A^b$ and CD86, and lack of expression of lineage markers as CD14 and Gr-1 (FIG. 31). ACTIMID™ showed no significant effect on cell surface marker expression by day 9 while ATRA showed marked downregulation of CD80, I-$A^b$ and Sca+ expression (data not shown). However by day 12, ACTIMID™ showed downregulation of CD86 and bright I-$A^b$ expression and upregulation of CD11b expression (FIG. 32). ATRA showed similar but more pronounced effects than ACTIMID™. In addition, ACTIMID™ showed no effects on the expression of CD40 and CD80 while ATRA showed marked downregulation of these molecules (not shown).

These results suggest that ACTIMID™ inhibits the differentiation of DC precursors into immature DC by downregulating CD86 and MHC II expression. The compound's effects are not as dramatic as those observed in human hematopoietic progenitors and this parallels the low activity of ACTIMID™ in mouse in vitro and in vivo in other models. The effect of ACTIMID™ is much less pronounced than that of ATRA, which is a teratogen in mice.

6.9. Example 9

Application of Differentiation Assay to Compounds Other than IMiDs

The methodology described above, i.e., the examination of the effect of IMiDs such as ACTIMID™ on the differentiation on early progenitor cells, such as $CD34^+$ cells, can be applied to any compound of interest, the effect of which on differentiation is desired to be known. As an example of the extension of this assay method to other compounds, we compared the effect of retinoic acid (ATRA) and aspirin to that of ACTIMID™ on the differentiation of $CD34^+$ cells toward the DC lineage versus the control (DMSO-treated) cells. Retinoic acid was studied because of its known effect on cellular proliferation and differentiation, its therapeutic use in some cancer, and its known teratogenic effect. Conversely, we studied the effect of aspirin because it is a commonly-used anti-inflammatory drug with no immunomodulatory properties. The results at day 6 of CD34+ progenitors cells cultured in the presence of SCF, Flt-3L, GM-CSF and TNF-α, with or without compound for a period of 6 days, are presented below in Table 2 (up arrow indicates an increase in the cell population; down arrow indicates a decrease).

TABLE 2

Comparison of effect of ACTIMID ™, retinoic acid, and aspirin on CD34+ progenitor cell differentiation.

| Cell Population | ACTIMID ™ | All-trans RA | Aspirin |
|---|---|---|---|
| CD34+ CD38− | ↑ | ↓ | No change |
| CD34− CD38+ | ↓ | ↑ | No change |
| CD1a+ CD14− | ↓ | ↓ | No change |
| CD1a− CD14+ | ↓ | ↓ | No change |
| CD15+ | ↑ | ↑ | No change |

In the literature other drugs have been shown to modulate cellular differentiation, for example, a recent paper reports the modulation by corticosteroids of DC generation from CD34+ progenitors cells. The profile differs from ACTIMID™ with an increase in the CD1a+ population and a decrease in the CD14+ population.

6.10. Example 10

Induction of Differentiation into Particular Cell Types

Cord blood cells and/or embryonic-like stem cells are induced to differentiate into a particular cell type by exposure to a growth factor. Growth factors that are used to induce induction include, but are not limited to: GM-CSF, IL-4, Flt3L, CD40L, IFN-alpha, TNF-alpha, IFN-gamma, IL-2, IL-6, retinoic acid, basic fibroblast growth factor, TGF-beta-1, TGF-beta-3, hepatocyte growth factor, epidermal growth factor, cardiotropin-1, angiotensinogen, angiotensin I (AI), angiotensin II (AII), AII $AT_2$ type 2 receptor agonists, or analogs or fragments thereof.

6.10.1. Induction of Differentiation into Neurons

This example describes the induction of cord blood cells and/or embryonic-like stem cells to differentiate into neurons. The following protocol is employed to induce neuronal differentiation:
1. Placental stem cells are grown for 24 hr in preinduction media consisting of DMEM/20% FBS and 1 mM beta-mercaptoethanol.
2. Preinduction media is removed and cells are washed with PBS.
3. Neuronal induction media consisting of DMEM and 1-10 mM betamercaptoethanol is added. Alternatively, induction media consisting of DMEM/2% DMSO/200 µM butylated hydroxyanisole may be used to enhance neuronal differentiation efficiency.
4. In certain embodiments, morphologic and molecular changes may occur as early as 60 minutes after exposure to serum-free media and betamercaptoethanol (Woodbury et al., J. Neurosci. Res., 61:364-370). RT/PCR may be used to assess the expression of e.g. nerve growth factor receptor and neurofilament heavy chain genes.

6.10.2. Induction of Differentiation into Adipocytes

This example describes the induction of cord blood cells and/or embryonic-like stem cells to differentiate into adipocytes. The following protocol is employed to induce adipogenic differentiation:
1. Placental stem cells are grown in MSCGM (Bio Whittaker) or DMEM supplemented with 15% cord blood serum.
2. Three cycles of induction/maintenance are used. Each cycle consists of feeding the placental stem cells with Adipogenesis Induction Medium (Bio Whittaker) and culturing the cells for 3 days (at 37° C., 5% $CO_2$), followed by 1-3 days of culture in Adipogenesis Maintenance Medium (Bio Whittaker). An induction medium is used that contains 1 µM dexamethasone, 0.2 mM indomethacin, 0.01 mg/ml insulin, 0.5 mM IBMX, DMEM-high glucose, FBS, and antibiotics.
3. After 3 complete cycles of induction/maintenance, the cells are cultured for an additional 7 days in adipogenesis maintenance medium, replacing the medium every 2-3 days.
4. Adipogenesis may be assessed by the development of multiple Intracytoplasmic lipid vesicles that can be easily observed using the lipophilic stain oil red O. RT/PCR assays are employed to examine the expression of lipase and fatty acid binding protein genes.

6.10.3. Induction Of Differentiation Into Chondrocytes

This example describes the induction of cord blood cells and/or embryonic-like stem cells to differentiate into chondrocytes. The following protocol is employed to induce chondrogenic differentiation:
1. Placental stem cells are maintained in MSCGM (Bio Whittaker) or DMEM supplemented with 15% cord blood serum.
2. Placental stem cells are aliquoted into a sterile polypropylene tube. The cells are centrifuged (150×g for 5 minutes), and washed twice in Incomplete Chondrogenesis Medium (Bio Whittaker).
3. After the last wash, the cells are resuspended in Complete Chondrogenesis Medium (Bio Whittaker) containing 0.01 µg/ml TGF-beta-3 at a concentration of 5×10 (5) cells/ml.
4. 0.5 ml of cells is aliquoted into a 15 ml polypropylene culture tube. The cells are pelleted at 150×g for 5 minutes. The pellet is left intact in the medium.
5. Loosely capped tubes are incubated at 37° C., 5% $CO_2$ for 24 hours.
6. The cell pellets are fed every 2-3 days with freshly prepared complete chondrogenesis medium.
7. Pellets are maintained suspended in medium by daily agitation using a low speed vortex.
8. Chondrogenic cell pellets are harvested after 14-28 days in culture.
9. Chondrogenesis may be characterized by e.g. observation of production of eosinophilic ground substance, assessing cell morphology, an/or RT/PCR for examining collagen 2 and collagen 9 gene expression.

6.10.4. Induction of Differentiation into Osteocytes

This example describes the induction of cord blood cells and/or embryonic-like stem cells to differentiate into osteocytes. The following protocol is employed to induce osteogenic differentiation:
1. Adherent cultures of placental stem cells are cultured in MSCGM (Bio Whittaker) or DMEM supplemented with 15% cord blood serum.
2. Cultures are rested for 24 hours in tissue culture flasks.
3. Osteogenic differentiation is induced by replacing MSCGM with Osteogenic Induction Medium (Bio Whittaker) containing 0.1 µM dexamethasone, 0.05 mM ascorbic acid-2-phosphate, 10 mM beta glycerophosphate.

4. Cells are fed every 3-4 days for 2-3 weeks with Osteogenic Induction Medium.
5. Differentiation is assayed using a calcium-specific stain and RT/PCR for alkaline phosphatase and osteopontin gene expression.

6.10.5. Induction Of Differentiation Into Hepatocytes

This example describes the induction of cord blood cells and/or embryonic-like stem cells to differentiate into hepatocytes. The following protocol is employed to induce hepatogenic differentiation:
1. Placental stem cells are cultured in DMEM/20% CBS supplemented with hepatocyte growth factor, 20 ng/ml; and epidermal growth factor, 100 ng/ml. KnockOut Serum Replacement may be used in lieu of FBS.
2. IL-6 50 ng/ml is added to induction flasks.

6.10.6. Induction Of Differentiation Into Pancreatic Cells

This example describes the induction of cord blood cells and/or embryonic-like stem cells to differentiate into pancreatic cells. The following protocol is employed to induce pancreatic differentiation:
1. Placental stem cells are cultured in DMEM/20% CBS, supplemented with basic fibroblast growth factor, 10 ng/ml; and transforming growth factor beta-1, 2 ng/ml. KnockOut Serum Replacement may be used in lieu of CBS.
2. Conditioned media from nestin-positive neuronal cell cultures is added to media at a 50/50 concentration.
3. Cells are cultured for 14-28 days, refeeding every 3-4 days.
4. Differentiation is characterized by assaying for insulin protein or insulin gene expression by RT/PCR.

6.10.7. Induction Of Differentiation Into Cardiac Cells

This example describes the induction of cord blood cells and/or embryonic-like stem cells to differentiate into cardiac cells. The following protocol is employed to induce myogenic differentiation:
1. Placental stem cells are cultured in DMEM/20% CBS, supplemented with retinoic acid, 1 µM; basic fibroblast growth factor, 10 ng/ml; and transforming growth factor beta-1, 2 ng/ml; and epidermal growth factor, 100 ng/ml. KnockOut Serum Replacement may be used in lieu of CBS.
2. Alternatively, placental stem cells are cultured in DMEM/20% CBS supplemented with 50 ng/ml Cardiotropin-1 for 24 hours.
3. Alternatively, placental stem cells are maintained in protein-free media for 5-7 days, then stimulated with human myocardium extract (escalating dose analysis). Myocardium extract is produced by homogenizing 1 gm human myocardium in 1% HEPES buffer supplemented with 1% cord blood serum. The suspension is incubated for 60 minutes, then centrifuged and the supernatant collected.
4. Cells are cultured for 10-14 days, refeeding every 3-4 days.
5. Differentiation is assessed using cardiac actin RT/PCR gene expression assays.

6.10.8. Characterization of Cord Blood Cells and/or Embryonic-Like Stem Cells Prior to and/or After Differentiation The embryonic-like stem cells, the cord blood cells and/or the populations of cord blood cells spiked with embryonic-like stem cells are characterized prior to and/or after differentiation by measuring changes in morphology and cell surface markers using techniques such as flow cytometry and immunocytochemistry, and measuring changes in gene expression using techniques, such as PCR. Cells that have been exposed to growth factors and/or that have differentiated are characterized by the presence or absence of the following cell surface markers: CD10+, CD29+, CD34−, CD38−, CD44+, CD45−, CD54+, CD90+, SH2+, SH3+, SH4+, SSEA3−, SSEA4−, OCT-4+, and ABC-p+. Preferably, the embryonic-like stem cell are characterized, prior to differentiation, by the presence of cell surface markers OCT-4+, APC-p+, CD34− and CD38−. Stem cells bearing these markers are as versatile (e.g., pluripotent) as human embryonic stem cells. Cord blood cells are characterized, prior to differentiation, by the presence of cell surface markers CD34+ and CD38+. Differentiated cells derived from embryonic-like stem cells, cord blood cells and/or a populations of cord blood cells spiked with embryonic-like stem cells preferably do not express these markers.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

7. LITERATURE

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention

What is claimed:

1. A method of treating an individual in need of granulocytes comprising:
   contacting mammalian $CD34^+$ or $CD133^+$ hematopoietic stem cells with 4-(amino)-2-(2,6-dioxo(3-piperidyl))-isoindoline-1,3-dione or 3-(4-amino-1-oxo-1,3-dihydro-isoindol-2-yl)-piperidine-2,6-dione, under conditions under which said hematopoietic stem cells differentiate, wherein said contacting increases the number of CFU-GM and decreases the number of BFU-E differentiated from said stem cells relative to the numbers of CFU-GM and BFU-E differentiated from said hematopoietic stem cells not contacted with said compound; and
   administering said differentiated cells to said individual.

2. The method of claim 1, wherein said individual is human.

3. The method of claim 1, wherein said individual has neutropenia.

4. The method of claim 1, wherein said individual has chronic granulomatous disease.

5. The method of claim 1, wherein said administering causes an increase in the number of $CD15^+$ granulocyte progenitors in said individual.

6. The method of claim 1, wherein said individual has an infection.

7. The method of claim 6, wherein said individual has a chronic infection.

8. The method of claim 6, wherein said infection is bacterial neonatal sepsis.

9. The method of claim 6, wherein said infection is neutropenia-associated infection.

10. The method of claim 9, wherein said individual is a cancer patient suffering a neutropenia-associated infection.

11. The method of claim 6, wherein said individual is a bone marrow transplant recipient.

* * * * *